(12) United States Patent
Fernando et al.

(10) Patent No.: US 9,750,434 B2
(45) Date of Patent: Sep. 5, 2017

(54) PERSONAL AUTHENTICATION APPARATUS, PERSONAL AUTHENTICATION METHOD, AND RECORDING MEDIUM

(71) Applicant: Panasonic Intellectual Property Management Co., Ltd., Osaka (JP)

(72) Inventors: Jeffry Bonar Fernando, Osaka (JP); Koji Morikawa, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/053,916

(22) Filed: Feb. 25, 2016

(65) Prior Publication Data

US 2016/0270699 A1     Sep. 22, 2016

(30) Foreign Application Priority Data

Mar. 17, 2015   (JP) .................................. 2015-054030

(51) Int. Cl.
*A61B 5/0456* (2006.01)
*A61B 5/0452* (2006.01)
(Continued)

(52) U.S. Cl.
CPC .......... *A61B 5/117* (2013.01); *A61B 5/04012* (2013.01); *A61B 5/0452* (2013.01); *A61B 5/0456* (2013.01); *A61B 5/7246* (2013.01)

(58) Field of Classification Search
CPC ..... A61B 5/117; A61B 5/0452; A61B 5/0456; G06K 9/0055; G06K 9/6255; G06K 2009/00939
See application file for complete search history.

(56) References Cited

U.S. PATENT DOCUMENTS

| | | | | |
|---|---|---|---|---|
| 2006/0136744 A1* | 6/2006 | Lange | ................ | G06K 9/00536 713/186 |
| 2010/0090798 A1* | 4/2010 | Garcia Molina | .... | G06K 9/0055 340/5.53 |

(Continued)

FOREIGN PATENT DOCUMENTS

| | | |
|---|---|---|
| JP | 2008-518708 | 6/2008 |
| JP | 2008-518709 | 6/2008 |

(Continued)

*Primary Examiner* — William Levicky
(74) *Attorney, Agent, or Firm* — Wenderoth, Lind & Ponack, L.L.P.

(57) ABSTRACT

A personal authentication apparatus includes a measuring circuit that measures a user electrocardiographic waveform using electrodes, a peak detector that detects peaks of first and second R waves and at least one of peaks of P and Q waves, and an acquirer. The acquirer expands/contracts a time interval between the peaks of the first and second R waves to a first time period and further (i) expands/contracts a time interval between the peaks of the first R wave and P wave to a second time period, (ii) expands/contracts a time interval between the peaks of the first R wave and Q wave to a third time period, or (iii) expands/contracts the time interval between the peaks of the first R wave and P wave to the second time period and expands/contracts the time interval between the peaks of the first R wave and Q wave to the third time period.

4 Claims, 53 Drawing Sheets

(51) Int. Cl.
    *G06K 9/00*           (2006.01)
    *A61B 5/117*         (2016.01)
    *A61B 5/04*           (2006.01)
    *A61B 5/00*           (2006.01)

(56) References Cited

U.S. PATENT DOCUMENTS

2012/0302903 A1* 11/2012 Zhang .................. A61B 5/7264
                                                                       600/508
2015/0373019 A1* 12/2015 El Saddik ............ A61B 5/0452
                                                                       340/5.52

FOREIGN PATENT DOCUMENTS

| JP | 2010-504793 | 2/2010 |
| JP | 2012-176106 | 9/2012 |
| JP | 2012-212362 | 11/2012 |
| WO | 2006/048701 | 5/2006 |
| WO | 2006/059190 | 6/2006 |

* cited by examiner

FIG. 5

|  | IDENTIFIED AS EXAMINEE 1 | IDENTIFIED AS EXAMINEE 2 | IDENTIFIED AS EXAMINEE 3 | IDENTIFIED AS EXAMINEE 4 | IDENTIFIED AS EXAMINEE 5 | IDENTIFIED AS EXAMINEE 6 |
|---|---|---|---|---|---|---|
| EXAMINEE 1 | 2 | 0 | 0 | 0 | 0 | 1 |
| EXAMINEE 2 | 0 | 1 | 0 | 1 | 0 | 1 |
| EXAMINEE 3 | 0 | 0 | 3 | 0 | 0 | 0 |
| EXAMINEE 4 | 0 | 0 | 0 | 1 | 0 | 2 |
| EXAMINEE 5 | 0 | 0 | 0 | 0 | 3 | 0 |
| EXAMINEE 6 | 0 | 0 | 0 | 0 | 0 | 3 |

(UNIT: NUMBER OF TIMES)

ACCURACY RATE = 72%

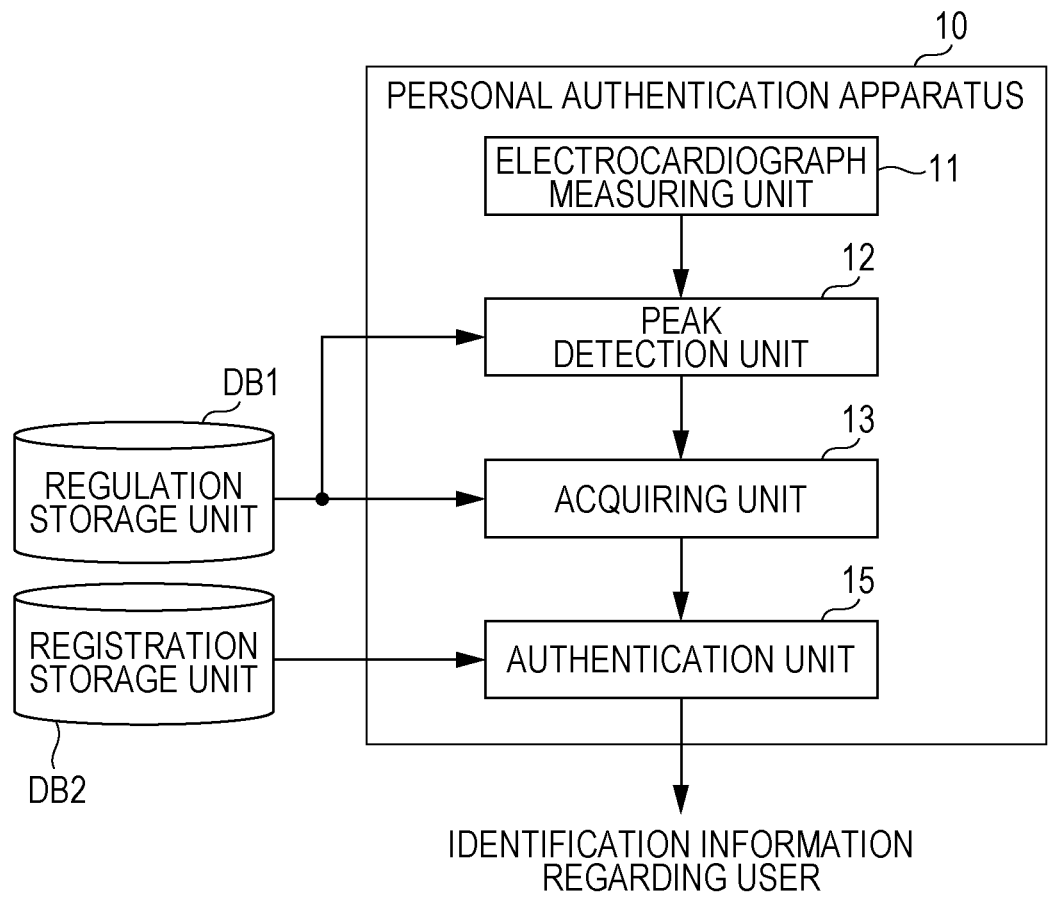

FIG. 9

| IDENTIFICATION INFORMATION REGARDING USER | REGISTERED ELECTROCARDIOGRAPHIC WAVEFORM | NUMBER OF R-R DURATIONS |
|---|---|---|
| ID001 | (TIME, MAGNITUDE OF CARDIAC POTENTIAL) = (0, 0.01), (1, 0.01), (2, 0.01), (3, 0.03)··· | RRNum1 |
| ID002 | (TIME, MAGNITUDE OF CARDIAC POTENTIAL) = (0, 0.01), (1, 0.02), (2, 0.03), (3, 0.01)··· | RRNum2 |
| ID003 | (TIME, MAGNITUDE OF CARDIAC POTENTIAL) = (0, 0.01), (1, 0.00), (2, 0.01), (3, 0.02)··· | RRNum3 |
| ID004 | (TIME, MAGNITUDE OF CARDIAC POTENTIAL) = (0, 0.02), (1, 0.02), (2, 0.01), (3, 0.02)··· | RRNum4 |
| ID005 | (TIME, MAGNITUDE OF CARDIAC POTENTIAL) = (0, 0.02), (1, 0.01), (2, 0.02), (3, 0.05)··· | RRNum5 |

REGISTRATION INFORMATION

REGISTRATION INFORMATION

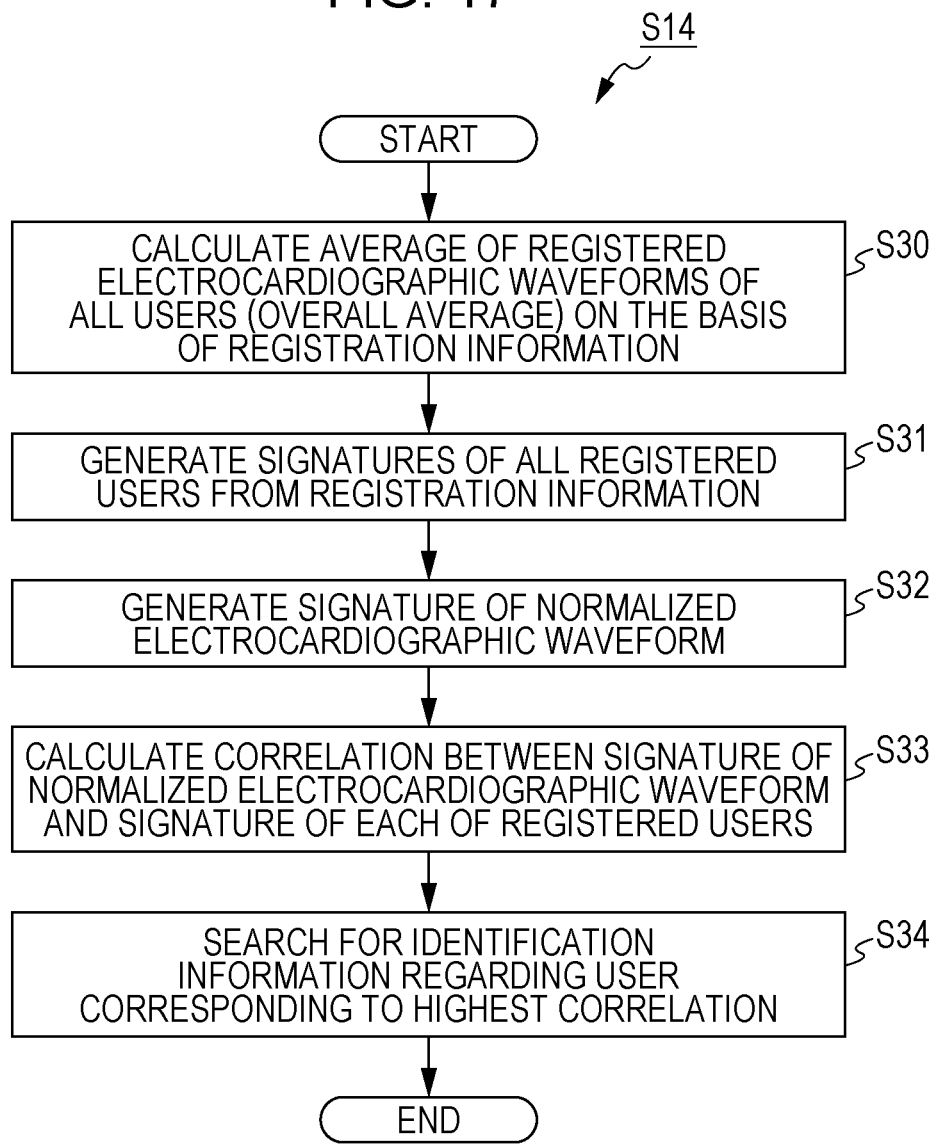

FIG. 18A

REGULATION INFORMATION

| PEAK TO BE ADJUSTED | PREDETERMINED TIME PERIOD |
|---|---|
| PEAK OF P WAVE | 0.85×RRnorm (SECOND PREDETERMINED TIME PERIOD) |
| PEAK OF Q WAVE | 0.95×RRnorm (THIRD PREDETERMINED TIME PERIOD) |
| PEAK OF S WAVE | 0.05×RRnorm (FOURTH PREDETERMINED TIME PERIOD) |
| PEAK OF T WAVE | 0.35×RRnorm (FIFTH PREDETERMINED TIME PERIOD) |

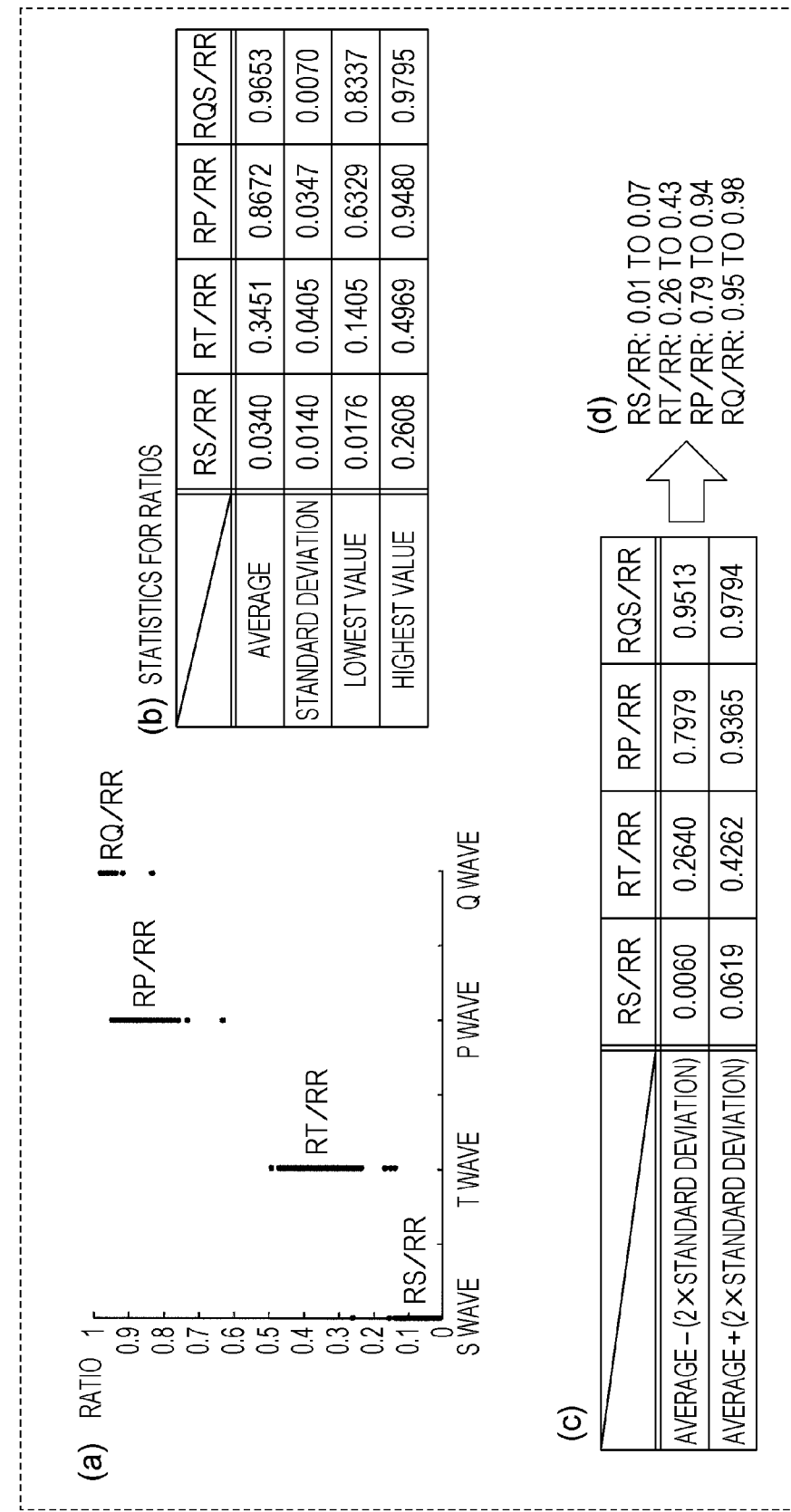

FIG. 21

| PEAK TO BE ADJUSTED | ACCURACY RATE (%) |
|---|---|
| P WAVE | 94 |
| Q WAVE | 83 |
| S WAVE | 72 |
| T WAVE | 67 |
| P WAVE, Q WAVE | 83 |
| P WAVE, S WAVE | 94 |
| P WAVE, T WAVE | 89 |
| Q WAVE, S WAVE | 83 |
| Q WAVE, T WAVE | 83 |
| S WAVE, T WAVE | 72 |
| P WAVE, Q WAVE, S WAVE | 83 |
| P WAVE, Q WAVE, T WAVE | 89 |
| P WAVE, S WAVE, T WAVE | 94 |
| Q WAVE, S WAVE, T WAVE | 83 |
| P WAVE, Q WAVE, S WAVE, T WAVE | 89 |

FIG. 24

| PEAK TO BE ADJUSTED | ACCURACY RATE (%) |
|---|---|
| NONE | 61 |
| P WAVE | 94 |
| Q WAVE | 83 |
| S WAVE | 72 |
| T WAVE | 56 |
| P WAVE, Q WAVE | 94 |
| P WAVE, S WAVE | 100 |
| P WAVE, T WAVE | 94 |
| Q WAVE, S WAVE | 94 |
| Q WAVE, T WAVE | 94 |
| S WAVE, T WAVE | 61 |
| P WAVE, Q WAVE, S WAVE | 94 |
| P WAVE, Q WAVE, T WAVE | 94 |
| P WAVE, S WAVE, T WAVE | 94 |
| Q WAVE, S WAVE, T WAVE | 94 |
| P WAVE, Q WAVE, S WAVE, T WAVE | 94 |

FIG. 26　REGISTRATION INFORMATION

| IDENTIFICATION INFORMATION REGARDING USER | REGISTERED CHARACTERISTIC VECTOR |
|---|---|
| ID001 | $\begin{pmatrix} A11 \\ B11 \end{pmatrix} \begin{pmatrix} A12 \\ B12 \end{pmatrix} \begin{pmatrix} A13 \\ B13 \end{pmatrix} \cdots$ |
| ID002 | $\begin{pmatrix} A21 \\ B21 \end{pmatrix} \begin{pmatrix} A22 \\ B22 \end{pmatrix} \begin{pmatrix} A23 \\ B23 \end{pmatrix} \cdots$ |
| ID003 | $\begin{pmatrix} A31 \\ B31 \end{pmatrix} \begin{pmatrix} A32 \\ B32 \end{pmatrix} \begin{pmatrix} A33 \\ B33 \end{pmatrix} \cdots$ |
| ID004 | $\begin{pmatrix} A41 \\ B41 \end{pmatrix} \begin{pmatrix} A42 \\ B42 \end{pmatrix} \begin{pmatrix} A43 \\ B43 \end{pmatrix} \cdots$ |
| ID005 | $\begin{pmatrix} A51 \\ B51 \end{pmatrix} \begin{pmatrix} A52 \\ B52 \end{pmatrix} \begin{pmatrix} A53 \\ B53 \end{pmatrix} \cdots$ |
|  |  |

FIG. 29

| NUMBER OF SELECTED ELEMENTS | PEAK TO BE ADJUSTED | HIGHEST ACCURACY RATE (%) |
|---|---|---|
| 2 | P WAVE | 100 |
| | Q WAVE | 100 |
| | P WAVE, Q WAVE | 100 |
| | P WAVE, S WAVE | 100 |
| | P WAVE, T WAVE | 100 |
| | Q WAVE, S WAVE | 100 |
| | Q WAVE, T WAVE | 100 |
| | P WAVE, Q WAVE, S WAVE | 100 |
| | P WAVE, Q WAVE, T WAVE | 100 |
| | P WAVE, S WAVE, T WAVE | 100 |
| | Q WAVE, S WAVE, T WAVE | 100 |
| | P WAVE, Q WAVE, S WAVE, T WAVE | 100 |
| 3 | P WAVE | 100 |
| | Q WAVE | 100 |
| | P WAVE, Q WAVE | 100 |
| | P WAVE, S WAVE | 100 |
| | P WAVE, T WAVE | 100 |
| | Q WAVE, S WAVE | 100 |
| | Q WAVE, T WAVE | 100 |
| | P WAVE, Q WAVE, S WAVE | 100 |
| | P WAVE, Q WAVE, T WAVE | 100 |
| | P WAVE, S WAVE, T WAVE | 100 |
| | Q WAVE, S WAVE, T WAVE | 100 |
| | P WAVE, Q WAVE, S WAVE, T WAVE | 100 |

FIG. 30

| NUMBER OF SELECTED ELEMENTS | PEAK TO BE ADJUSTED | NUMBER OF COMBINATIONS HAVING ACCURACY RATE OF 100% |
|---|---|---|
| 2 | P WAVE | 3 |
| | Q WAVE | 1 |
| | P WAVE, Q WAVE | 8 |
| | P WAVE, S WAVE | 15 |
| | P WAVE, T WAVE | 7 |
| | Q WAVE, S WAVE | 11 |
| | Q WAVE, T WAVE | 3 |
| | P WAVE, Q WAVE, S WAVE | 27 |
| | P WAVE, Q WAVE, T WAVE | 14 |
| | P WAVE, S WAVE, T WAVE | 36 |
| | Q WAVE, S WAVE, T WAVE | 13 |
| | P WAVE, Q WAVE, S WAVE, T WAVE | 33 |
| 3 | P WAVE | 1706 |
| | Q WAVE | 1010 |
| | P WAVE, Q WAVE | 2219 |
| | P WAVE, S WAVE | 4562 |
| | P WAVE, T WAVE | 634 |
| | Q WAVE, S WAVE | 2556 |
| | Q WAVE, T WAVE | 263 |
| | P WAVE, Q WAVE, S WAVE | 4482 |
| | P WAVE, Q WAVE, T WAVE | 761 |
| | P WAVE, S WAVE, T WAVE | 3717 |
| | Q WAVE, S WAVE, T WAVE | 726 |
| | P WAVE, Q WAVE, S WAVE, T WAVE | 4204 |

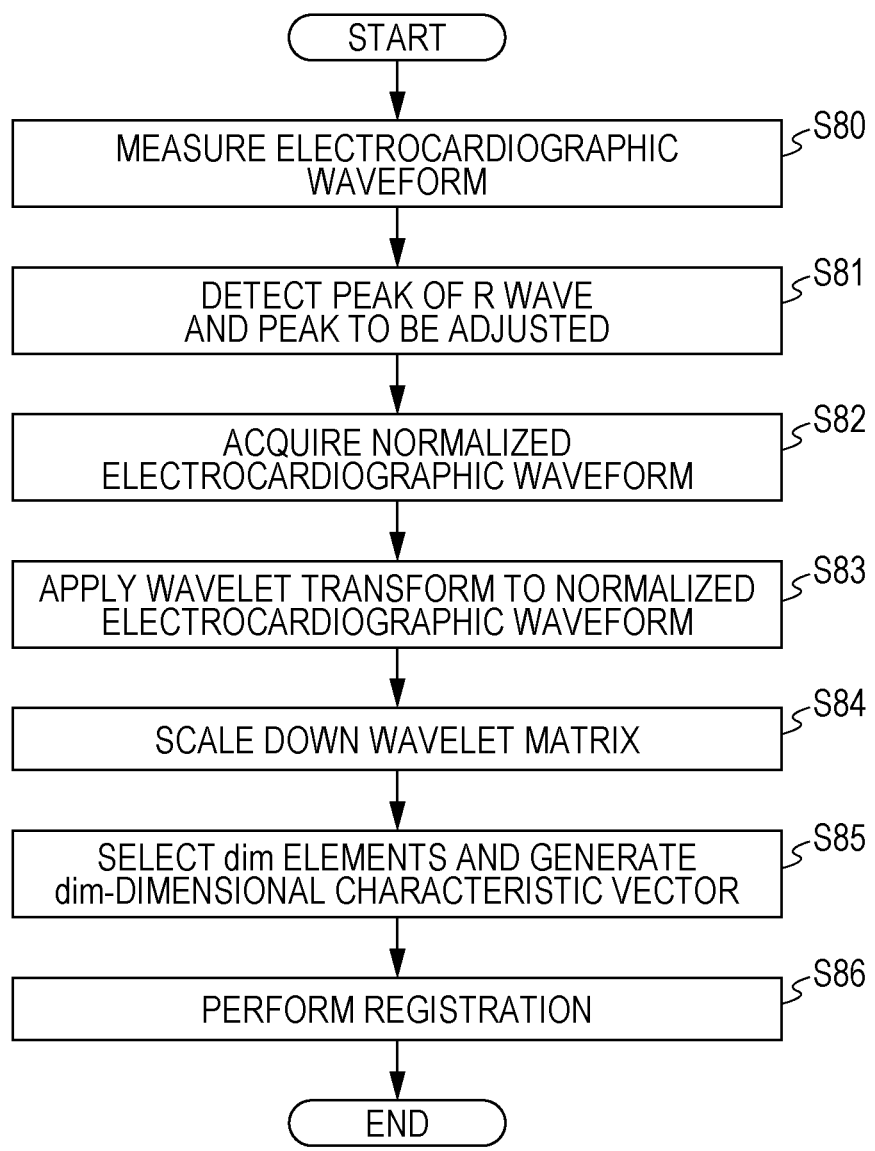

FIG. 37

| | | ACCURACY RATE (%) | |
|---|---|---|---|
| | | >20s | 3s |
| FIRST EMBODIMENT | PEAK TO BE ADJUSTED: NONE | 72 | 61 |
| | PEAK TO BE ADJUSTED: P WAVE | 94 | 56 |
| | PEAK TO BE ADJUSTED: Q WAVE | 83 | 67 |
| | PEAK TO BE ADJUSTED: P WAVE, Q WAVE | 83 | 67 |
| | PEAK TO BE ADJUSTED: P WAVE, S WAVE | 94 | 56 |
| | PEAK TO BE ADJUSTED: P WAVE, T WAVE | 89 | 67 |
| | PEAK TO BE ADJUSTED: Q WAVE, S WAVE | 83 | 67 |
| | PEAK TO BE ADJUSTED: Q WAVE, T WAVE | 83 | 61 |
| | PEAK TO BE ADJUSTED: P WAVE, Q WAVE, S WAVE | 83 | 67 |
| | PEAK TO BE ADJUSTED: P WAVE, Q WAVE, T WAVE | 89 | 67 |
| | PEAK TO BE ADJUSTED: P WAVE, S WAVE, T WAVE | 94 | 67 |
| | PEAK TO BE ADJUSTED: Q WAVE, S WAVE, T WAVE | 83 | 61 |
| | PEAK TO BE ADJUSTED: P WAVE, Q WAVE, S WAVE, T WAVE | 89 | 72 |

FIG. 38

| | | | HIGHEST ACCURACY RATE (%) | |
|---|---|---|---|---|
| | | | > 20s | 3s |
| SECOND EMBODIMENT | NUMBER OF SELECTED ELEMENTS = 2 | PEAK TO BE ADJUSTED: P WAVE | 100 | 83 |
| | | PEAK TO BE ADJUSTED: Q WAVE | 100 | 89 |
| | | PEAK TO BE ADJUSTED: P WAVE, Q WAVE | 100 | 83 |
| | | PEAK TO BE ADJUSTED: P WAVE, S WAVE | 100 | 89 |
| | | PEAK TO BE ADJUSTED: P WAVE, T WAVE | 100 | 89 |
| | | PEAK TO BE ADJUSTED: Q WAVE, S WAVE | 100 | 94 |
| | | PEAK TO BE ADJUSTED: Q WAVE, T WAVE | 100 | 89 |
| | | PEAK TO BE ADJUSTED: P WAVE, Q WAVE, S WAVE | 100 | 89 |
| | | PEAK TO BE ADJUSTED: P WAVE, Q WAVE, T WAVE | 100 | 89 |
| | | PEAK TO BE ADJUSTED: P WAVE, S WAVE, T WAVE | 100 | 89 |
| | | PEAK TO BE ADJUSTED: Q WAVE, S WAVE, T WAVE | 100 | 94 |
| | | PEAK TO BE ADJUSTED: P WAVE, Q WAVE, S WAVE, T WAVE | 100 | 89 |
| | NUMBER OF SELECTED ELEMENTS = 3 | PEAK TO BE ADJUSTED: P WAVE | 100 | 100 |
| | | PEAK TO BE ADJUSTED: Q WAVE | 100 | 100 |
| | | PEAK TO BE ADJUSTED: P WAVE, Q WAVE | 100 | 94 |
| | | PEAK TO BE ADJUSTED: P WAVE, S WAVE | 100 | 94 |
| | | PEAK TO BE ADJUSTED: P WAVE, T WAVE | 100 | 94 |
| | | PEAK TO BE ADJUSTED: Q WAVE, S WAVE | 100 | 100 |
| | | PEAK TO BE ADJUSTED: Q WAVE, T WAVE | 100 | 94 |
| | | PEAK TO BE ADJUSTED: P WAVE, Q WAVE, S WAVE | 100 | 100 |
| | | PEAK TO BE ADJUSTED: P WAVE, Q WAVE, T WAVE | 100 | 94 |
| | | PEAK TO BE ADJUSTED: P WAVE, S WAVE, T WAVE | 100 | 94 |
| | | PEAK TO BE ADJUSTED: Q WAVE, S WAVE, T WAVE | 100 | 100 |
| | | PEAK TO BE ADJUSTED: P WAVE, Q WAVE, S WAVE, T WAVE | 100 | 94 |

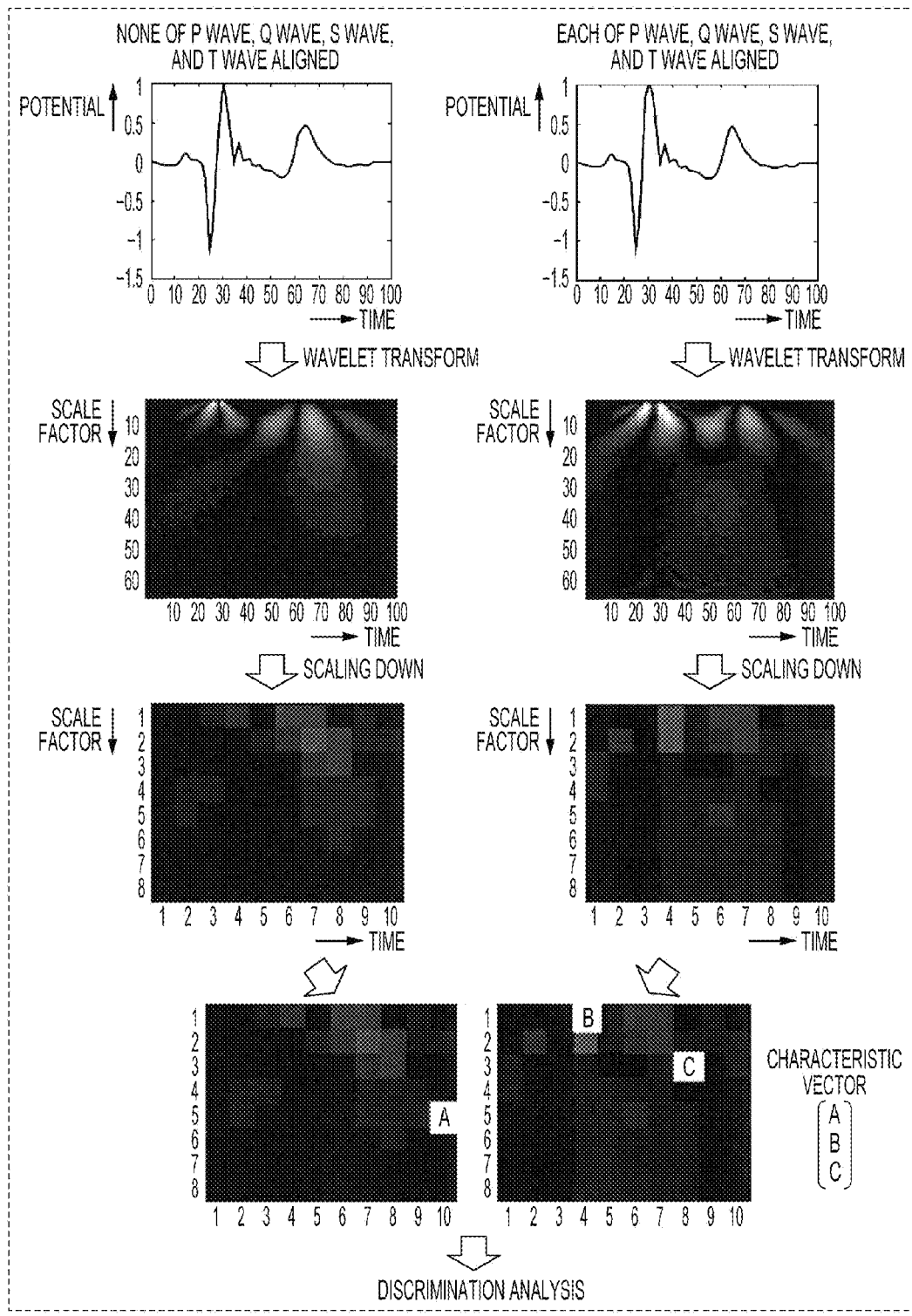

FIG. 40

| | | HIGHEST ACCURACY RATE (%) | |
|---|---|---|---|
| | | > 20s | 3s |
| NUMBER OF SELECTED ELEMENTS = 2 | PEAK TO BE ADJUSTED: P WAVE | 100 | 83 |
| | PEAK TO BE ADJUSTED: Q WAVE | 89 | 83 |
| | PEAK TO BE ADJUSTED: P WAVE, Q WAVE | 100 | 83 |
| | PEAK TO BE ADJUSTED: P WAVE, S WAVE | 100 | 83 |
| | PEAK TO BE ADJUSTED: P WAVE, T WAVE | 100 | 83 |
| | PEAK TO BE ADJUSTED: Q WAVE, S WAVE | 94 | 89 |
| | PEAK TO BE ADJUSTED: Q WAVE, T WAVE | 94 | 83 |
| | PEAK TO BE ADJUSTED: P WAVE, Q WAVE, S WAVE | 100 | 83 |
| | PEAK TO BE ADJUSTED: P WAVE, Q WAVE, T WAVE | 100 | 83 |
| | PEAK TO BE ADJUSTED: P WAVE, S WAVE, T WAVE | 100 | 89 |
| | PEAK TO BE ADJUSTED: Q WAVE, S WAVE, T WAVE | 100 | 94 |
| | PEAK TO BE ADJUSTED: P WAVE, Q WAVE, S WAVE, T WAVE | 100 | 89 |

FIG. 41

| | | HIGHEST ACCURACY RATE (%) | |
|---|---|---|---|
| | | >20s | 3s |
| NUMBER OF SELECTED ELEMENTS =3 | PEAK TO BE ADJUSTED: P WAVE | 100 | 100 |
| | PEAK TO BE ADJUSTED: Q WAVE | 100 | 94 |
| | PEAK TO BE ADJUSTED: P WAVE, Q WAVE | 100 | 100 |
| | PEAK TO BE ADJUSTED: P WAVE, S WAVE | 100 | 100 |
| | PEAK TO BE ADJUSTED: P WAVE, T WAVE | 100 | 100 |
| | PEAK TO BE ADJUSTED: Q WAVE, S WAVE | 100 | 94 |
| | PEAK TO BE ADJUSTED: Q WAVE, T WAVE | 100 | 89 |
| | PEAK TO BE ADJUSTED: P WAVE, Q WAVE, S WAVE | 100 | 94 |
| | PEAK TO BE ADJUSTED: P WAVE, Q WAVE, T WAVE | 100 | 94 |
| | PEAK TO BE ADJUSTED: P WAVE, S WAVE, T WAVE | 100 | 100 |
| | PEAK TO BE ADJUSTED: Q WAVE, S WAVE, T WAVE | 100 | 94 |
| | PEAK TO BE ADJUSTED: P WAVE, Q WAVE, S WAVE, T WAVE | 100 | 100 |

FIG. 42

| | | NUMBER OF COMBINATIONS HAVING ACCURACY RATE OF 100% | |
|---|---|---|---|
| | | >20s | 3s |
| NUMBER OF SELECTED ELEMENTS =2 | PEAK TO BE ADJUSTED: P WAVE | 1 | 0 |
| | PEAK TO BE ADJUSTED: Q WAVE | 0 | 0 |
| | PEAK TO BE ADJUSTED: P WAVE, Q WAVE | 2 | 0 |
| | PEAK TO BE ADJUSTED: P WAVE, S WAVE | 2 | 0 |
| | PEAK TO BE ADJUSTED: P WAVE, T WAVE | 1 | 0 |
| | PEAK TO BE ADJUSTED: Q WAVE, S WAVE | 0 | 0 |
| | PEAK TO BE ADJUSTED: Q WAVE, T WAVE | 0 | 0 |
| | PEAK TO BE ADJUSTED: P WAVE, Q WAVE, S WAVE | 5 | 0 |
| | PEAK TO BE ADJUSTED: P WAVE, Q WAVE, T WAVE | 5 | 0 |
| | PEAK TO BE ADJUSTED: P WAVE, S WAVE, T WAVE | 4 | 0 |
| | PEAK TO BE ADJUSTED: Q WAVE, S WAVE, T WAVE | 1 | 0 |
| | PEAK TO BE ADJUSTED: P WAVE, Q WAVE, S WAVE, T WAVE | 12 | 0 |

FIG. 43

| | | NUMBER OF COMBINATIONS HAVING ACCURACY RATE OF 100% | |
|---|---|---|---|
| | | > 20s | 3s |
| NUMBER OF SELECTED ELEMENTS = 3 | PEAK TO BE ADJUSTED: P WAVE | 1189 | 1 |
| | PEAK TO BE ADJUSTED: Q WAVE | 22 | 0 |
| | PEAK TO BE ADJUSTED: P WAVE, Q WAVE | 436 | 1 |
| | PEAK TO BE ADJUSTED: P WAVE, S WAVE | 2134 | 1 |
| | PEAK TO BE ADJUSTED: P WAVE, T WAVE | 1239 | 1 |
| | PEAK TO BE ADJUSTED: Q WAVE, S WAVE | 69 | 0 |
| | PEAK TO BE ADJUSTED: Q WAVE, T WAVE | 117 | 0 |
| | PEAK TO BE ADJUSTED: P WAVE, Q WAVE, S WAVE | 1457 | 0 |
| | PEAK TO BE ADJUSTED: P WAVE, Q WAVE, T WAVE | 814 | 0 |
| | PEAK TO BE ADJUSTED: P WAVE, S WAVE, T WAVE | 4826 | 1 |
| | PEAK TO BE ADJUSTED: Q WAVE, S WAVE, T WAVE | 210 | 0 |
| | PEAK TO BE ADJUSTED: P WAVE, Q WAVE, S WAVE, T WAVE | 12619 | 2 |

PERSONAL AUTHENTICATION APPARATUS, PERSONAL AUTHENTICATION METHOD, AND RECORDING MEDIUM

BACKGROUND

1. Technical Field

The present disclosure relates to an apparatus, a method, and a recording medium for authenticating a person using electrocardiographic waveform of the person.

2. Description of the Related Art

An apparatus and a method for measuring the electrocardiographic waveform of a user (a person) and authenticating the user using the electrocardiographic waveform have been developed (refer to, for example, Japanese Patent No. 4782141).

SUMMARY

The apparatus and the method described in Japanese Patent No. 4782141 has a problem of low accuracy of the authentication.

One non-limiting and exemplary embodiment provides a personal authentication apparatus capable of authenticating persons with high accuracy.

In one general aspect, the techniques disclosed here feature a personal authentication apparatus including an electrocardiograph measuring circuit that measures an electrocardiographic waveform of a user using a plurality of electrodes in contact with the user, a peak detection unit that detects at least one of a peak of a P wave and a peak of a Q wave, a peak of the first R wave, and a peak of the second R wave in the electrocardiographic waveform, an acquiring unit that acquires a first normalized electrocardiographic waveform by expanding or contracting the electrocardiographic waveform in a time axis direction and an amplitude direction on the basis of the peaks of the waves, and an authentication unit that refers to identification information regarding a plurality of users and registration information including characteristic information indicating characteristics of the electrocardiographic waveform corresponding to the identification information regarding each of the users and outputs the identification information regarding a user corresponding to the characteristic information indicating the characteristics similar to the first normalized electrocardiographic waveform. The acquiring unit expands or contracts a time interval between the peak of the first R wave and the peak of the second R wave to a first predetermined time period. The acquiring unit (i) expands or contracts a time interval between the peak of the first R wave and a peak of the P wave to a second predetermined time period, (ii) expands or contracts a time interval between the peak of the first R wave and a peak of the Q wave to a third predetermined time period, or (iii) expands or contracts the time interval between the peak of the first R wave and the peak of the P wave to the second predetermined time period and expands or contracts the time interval between the peak of the first R wave and the peak of the Q wave to the third predetermined time period.

According to the present disclosure, a person can be authenticated with high accuracy.

It should be noted that general or specific embodiments may be implemented as a system, a method, an integrated circuit, a computer program, a computer-readable storage medium or any selective combination thereof. The computer-readable storage medium includes a nonvolatile storage medium, such as a compact disc-read only memory (CD-ROM).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 5 illustrates the result of authentication carried out for six examinees using a method based on Japanese Patent No. 4782141;

FIG. 7 is a block diagram of the configuration of a personal authentication apparatus according to a first exemplary embodiment;

FIG. 8 illustrates an example of regulation information according to the first exemplary embodiment;

FIG. 9 illustrates an example of registration information according to the first exemplary embodiment;

FIG. 17 is a flowchart of the processing operation performed by an authentication unit according to the first exemplary embodiment;

FIG. 18A illustrates another example of the regulation information according to the first exemplary embodiment;

FIG. 18B illustrates how predetermined time periods in the regulation information are determined according to the first exemplary embodiment;

FIG. 21 illustrates combinations of the peaks (the peaks to be adjusted) each aligned through normalization and the accuracy rate of each of the combinations according to the first exemplary embodiment;

FIG. 24 illustrates combinations of the peaks each aligned through normalization (the peaks to be adjusted) and the accuracy rate of each of the combinations when authentication is performed without using the signature according to the first exemplary embodiment and the modification;

FIG. 26 illustrates an example of registration information according to the second exemplary embodiment;

FIG. 29 illustrates combinations of the peaks to be adjusted for each of the numbers of selected elements and the highest accuracy rate of each of the combinations according to the second exemplary embodiment;

FIG. 30 illustrates peak-to-be-adjusted combinations for each of the numbers of selected elements and the number of element combinations each having an accuracy rate of 100% for the peak-to-be-adjusted combination according to the second exemplary embodiment;

FIG. 36 is a flowchart of the processing operation performed by the personal authentication apparatus in a registration phase according to the modification of the second exemplary embodiment;

FIG. 37 illustrates the accuracy rate when the electrocardiographic waveform is measured for 20 seconds or longer and the accuracy rate when the electrocardiographic waveform is measured for 3 seconds in the first exemplary embodiment;

FIG. 38 illustrates the accuracy rate when the electrocardiographic waveform is measured for 20 seconds or longer and the accuracy rate when the electrocardiographic waveform is measured for 3 seconds in the second exemplary embodiment;

FIG. 39 illustrates an example of a method for generating a characteristic vector according to a third exemplary embodiment;

FIG. 40 illustrates the highest accuracy rate when the number of selected elements is 2 according to the third exemplary embodiment;

FIG. 41 illustrates the highest accuracy rate when the number of selected elements is 3 according to the third exemplary embodiment;

FIG. 42 illustrates the number of element combinations having an accuracy rate of 100% when the number of selected elements is 2 according to the third exemplary embodiment;

FIG. 43 illustrates the number of element combinations having an accuracy rate of 100% when the number of selected elements is 3 according to the third exemplary embodiment;

DETAILED DESCRIPTION

Underlying Knowledge Forming Basis of the Present Disclosure

The present inventors found that the following problem arose in the apparatus and method based on Japanese Patent No. 4782141 cited in the above section "Description of the Related Art". The apparatus and method based on Japanese Patent No. 4782141 are described first.

An electrocardiographic waveform represents a time variation of the cardiac potential, which is the potential periodically appearing due to the polarization process of the atrium and ventricle of the heart.

Figure 1:
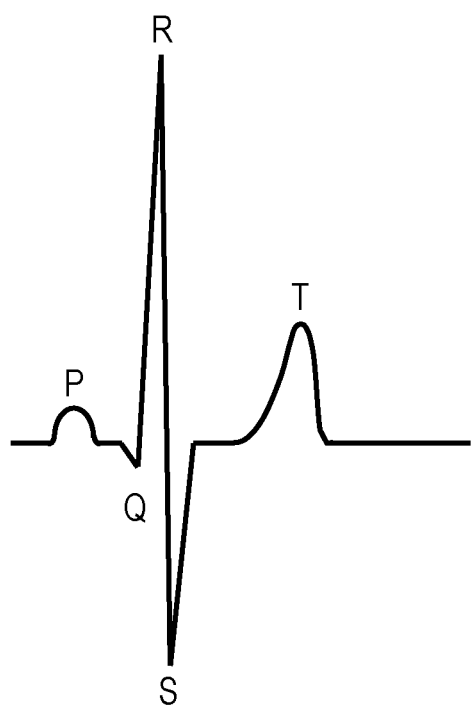
FIG. 1 illustrates an electrocardiographic waveform for one period.

FIG. 1 illustrates the electrocardiographic waveform for 1 period.

The electrocardiographic waveform includes a P wave, a Q wave, an R wave, an S wave, and a T wave. The P wave is a wave caused by depolarization of the atrium. The Q wave, R wave, and S wave are waves caused by the depolarization of the ventricle. The T wave is a wave caused by repolarization of the ventricle.

The characteristics of the electrocardiographic waveform vary person to person. Accordingly, by using the electrocardiographic waveform, a person can be authenticated. Hereinafter, the person is referred to as a "user". Note that even in the electrocardiographic waveform of the same user, the amplitude and period of the waveform vary. Accordingly, the difference among the electrocardiographic waveforms of a plurality of users need to be distinguished without being influenced by a variation of the cardiac potential of the same user.

To use the biological information including the electrocardiographic waveform for personal authentication, a registration phase and an authentication phase are required. In the registration phase, the biological information regarding a plurality of users used for personal authentication is registered. In the authentication phase, among the plurality of users in the biological information, a user having the biological information that matches measured user biological information is searched for.

Figure 2:
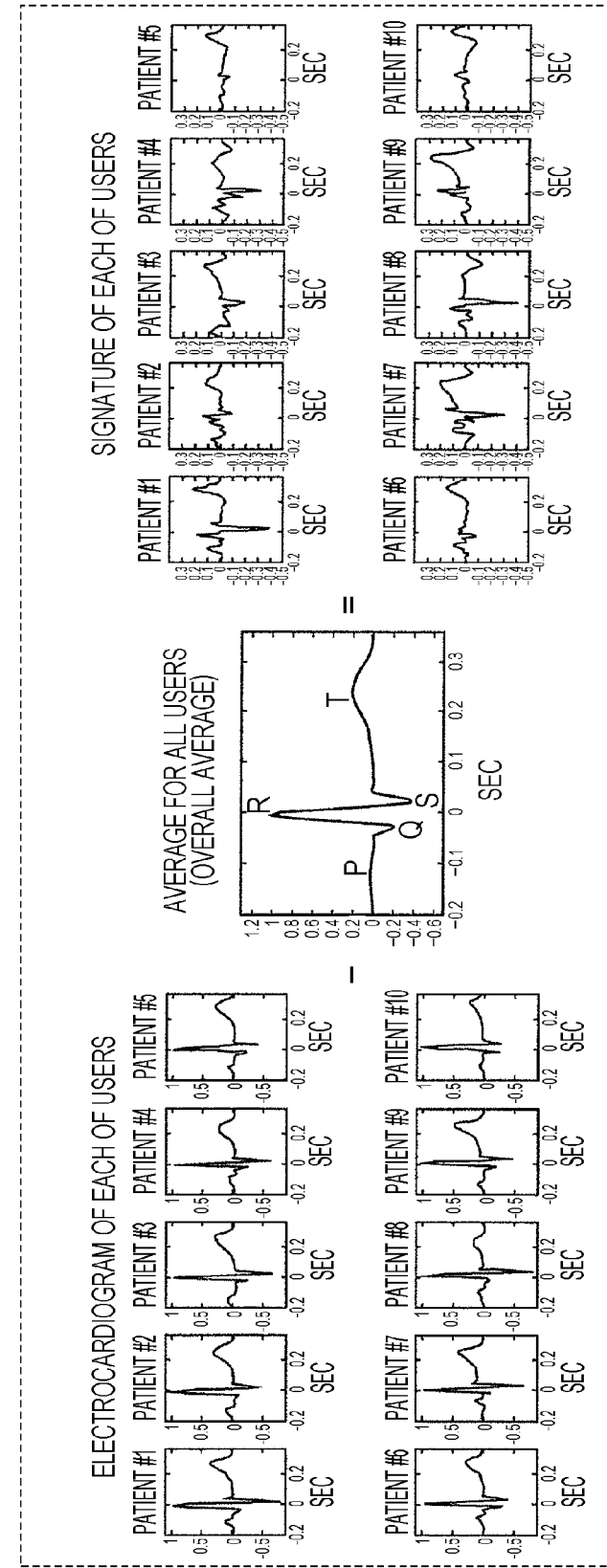
FIG. 2 is a schematic illustration of personal authentication using an electrocardiographic waveform based on Japanese Patent No. 4782141.

FIG. 2 is a schematic illustration of personal authentication using the electrocardiographic waveform based on Japanese Patent No. 4782141.

In the registration phase, the electrocardiographic waveform of each of users for one period is normalized on the basis of an R-R duration and the peak value of the R wave. The R-R duration is defined as a duration from the peak of an R wave to the peak of the next R wave in an electrocardiographic waveform. Subsequently, the average value (the overall average) of the electrocardiographic waveforms of all the users is calculated. The electrocardiographic waveform of the overall average is subtracted from the normalized electrocardiographic waveform of each of the users. The differences obtained through the subtraction are stored as the signatures of the users.

In the authentication phase, the electrocardiographic waveform of a user selected as an examinee for one period is normalized on the basis of the R-R duration and the peak value of the R wave. The overall average is subtracted from the normalized electrocardiographic waveform. Subsequently, from among the signatures of all the registered users, the signature having the highest correlation with the difference obtained by the subtraction is searched for. Thereafter, the identification information (ID) of a user corresponding to the found signature is output.

The present inventors studied the issue of the personal authentication method using the electrocardiographic waveform based on Japanese Patent No. 4782141. More specifically, the personal authentication was performed in the manner described below in accordance with the personal authentication method based on Japanese Patent No. 4782141.

The electrocardiographic waveforms of six examinees were measured using a wireless biopotential sensor. Each of the examinees held an Ag electrode by one hand and held an AgCl electrode by the other hand, and the electrocardiographic waveform of the examinee was measured. In the measurement, a sampling frequency of 1024 Hz was used. Twelve measurements of the electrocardiographic waveform were conducted for each of the examinees at different timings in three days. In each of the measurements, the electrocardiographic waveform was measured for longer than 20 seconds (21 to 39 seconds). Among 12 measured electrocardiographic waveforms, 9 electrocardiographic waveforms were used for registration, and 3 electrocardiographic waveforms were used for authentication.

Since the measured electrocardiographic waveform contained low-frequency noise, a 5-Hz highpass filter was applied to the electrocardiographic waveform as pre-processing. After the pre-processing was completed, the peak of each of the P wave, Q wave, R wave, S wave, and T wave was detected from the electrocardiographic waveform. Since the amplitude and the period of the electrocardiographic waveform varied each time, the electrocardiographic waveform was normalized for each period on the basis of the cycle time (the R-R duration) and the amplitude (the R-wave peak value). In the normalization based on the R-R duration, the electrocardiographic waveform between two R waves was expanded or contracted in the time axis direction so that the R-R duration was set to a predetermined duration.

Figure 3:
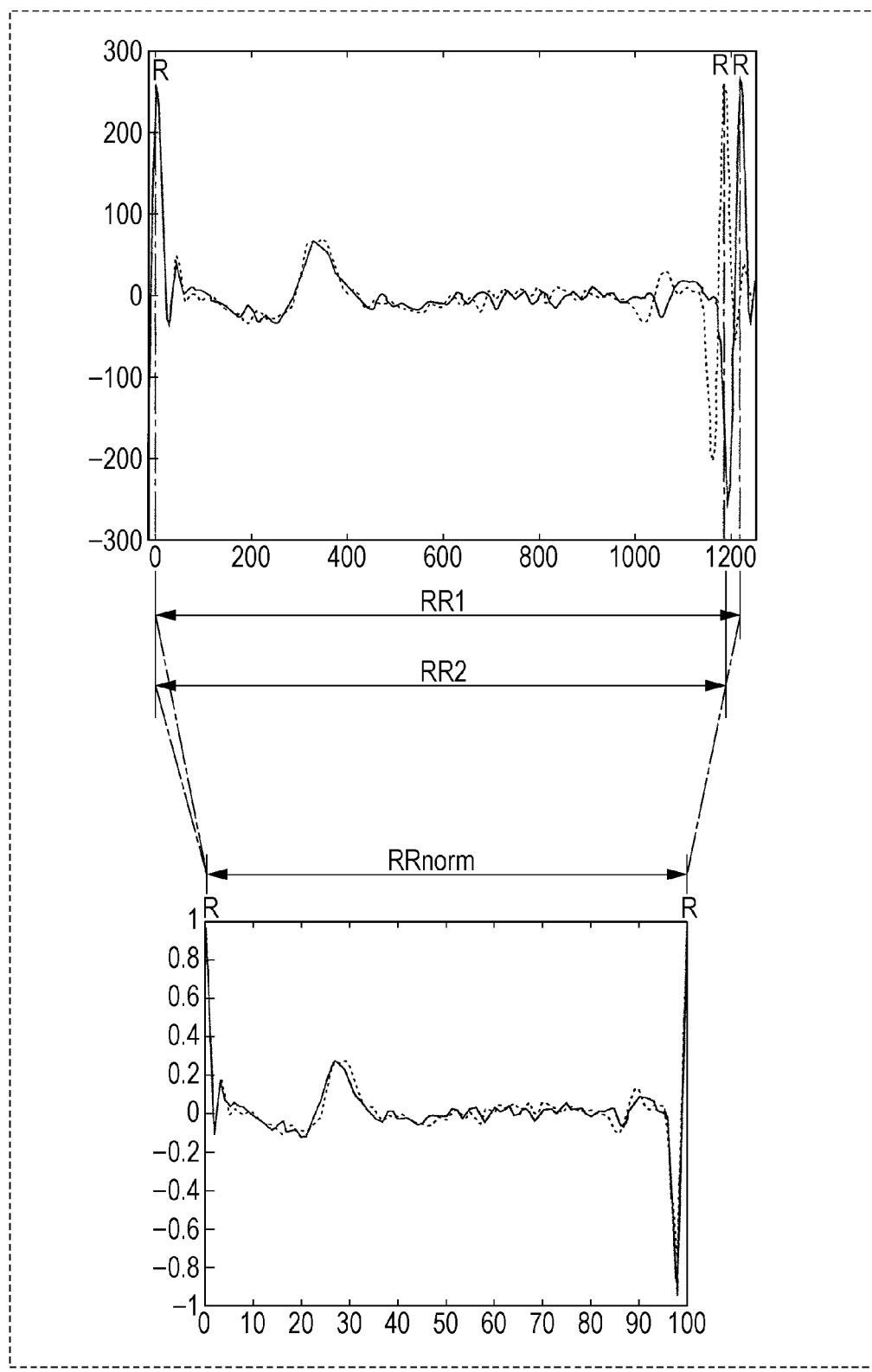
FIG. 3 illustrates an example of expansion or contraction of an electrocardiographic waveform between two R waves in the time axis direction.

FIG. 3 illustrates an example of expansion or contraction of an electrocardiographic waveform between two R waves in the time axis direction.

The electrocardiographic waveform was expanded or contracted so that two different R-R durations RR1 and RR2 were set to a predetermined time RRnorm. Through such expansion or contraction, the electrocardiographic waveform was normalized in the time axis direction. Note that the ordinate of the graph illustrated in FIG. 3 represents the potential, and the abscissa represents a sample number or the number of samples. Since the sampling frequency is 1024 Hz, the sample number or the number of samples in the abscissa indicated the point in time or the period of time in accordance with the sampling frequency. In this example, RRnorm is 100 samples. Linear interpolation is used as the expansion and contraction method of the electrocardiographic waveform in the time axis direction.

Figure 4A:
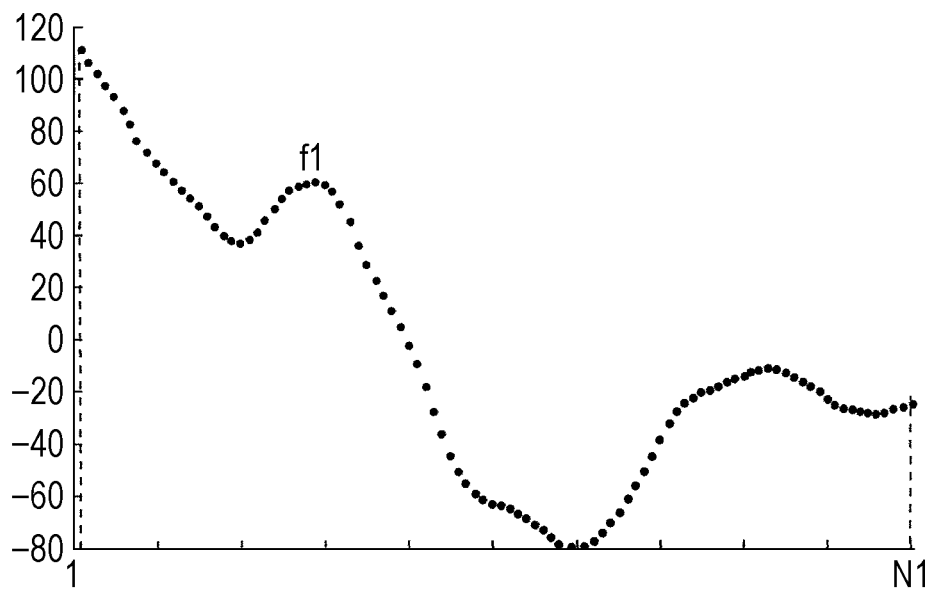
FIG. 4A illustrates an example of linear interpolation.
Figure 4B:
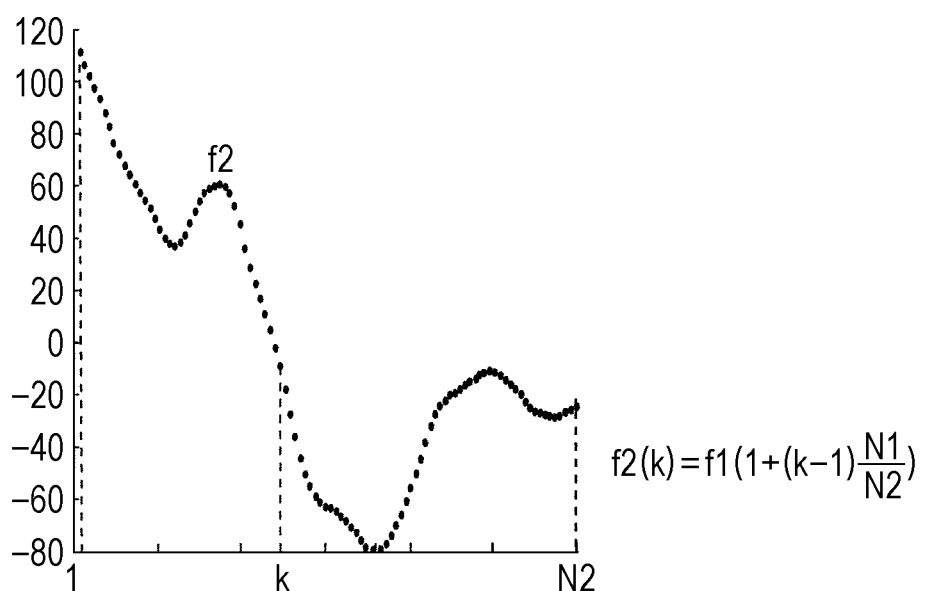
FIG. 4B illustrates an example of linear interpolation.

FIGS. 4A and 4B illustrate an example of the linear interpolation.

As illustrated in FIG. 4B, a waveform f1 formed from samples 1 to N1 illustrated in FIG. 4A is normalized into a waveform f2 formed from samples 1 to N2. The sample number k in the waveform f2 is given using the sample number in the waveform f1 as follows:

$$f2(k) = f1\left(1 + (k-1)\frac{N1}{N2}\right) \quad (1)$$

If (1+(k−1)N1/N2) is not an integer, f2(k) is calculated as follows:

$$f2(k) = \text{ratio } 1 \times f1\left(\left\lceil 1 + (k-1)\frac{N1}{N2}\right\rceil\right) + \text{ratio } 2 \times f1\left(\left\lfloor 1 + (k-1)\frac{N1}{N2}\right\rfloor\right) \quad (2)$$

$$\text{ratio } 1 = 1 - \text{ratio } 2$$

$$\text{ratio } 2 = \left(1 + (k-1)\frac{N1}{N2}\right) - \left\lfloor 1 + (k-1)\frac{N1}{N2}\right\rfloor$$

where

⌊ ⌋ and ⌈ ⌉ represent rounding in the negative and positive infinite directions, respectively.

Subsequently, in the normalization based on the peak value of the R wave, the electrocardiographic waveform in each of the R-R durations was divided into two durations on the basis of a predetermined ratio ratio3. Let RR denote the time length of the R-R duration. Then, the potential of the electrocardiographic waveform in the time range from 0 to ratio3×RR was divided by the peak value of a first R wave. In addition, the potential of the electrocardiographic waveform in the time range from ratio3×RR to the terminal end was divided by the peak value of a second R wave. By using such division, that is, expansion or contraction, the electrocardiographic waveform was normalized in the amplitude direction. Through such expansion or contraction, the peak value of the R wave was set to 1 at all times. In this example, ratio3 was 0.7.

If there were a plurality of waveforms in the R-R duration in the electrocardiographic waveform measured for one user, a plurality of the normalized electrocardiographic waveforms for one period were averaged on the basis of the R-R duration and the peak value of the R wave. In the averaged electrocardiographic waveform, the waveform in the time range from ratio3×RR to the terminal end was shifted to the top end of the waveform in the time range from 0 to ratio3×RR. In this manner, the P wave, Q wave, R wave, S wave, and T wave are arranged in this order. Note that the shift operation is optional.

The data registered for a user i includes an averaged electrocardiographic waveform ECGMean$_i$ for the time RRnorm and the number of the R-R durations RRNum$_i$. Let N denote the number of registered users. Then, the average ECGMeanAll for all the users (the overall average) is calculated as follows:

$$ECGMeanAll(k) = \frac{\sum_{i=1}^{N} ECGMean_i(k) \times RRNum_i}{\sum_{i=1}^{N} RRNum_i} \quad (3)$$

where k represents the sample number and is any one of 1 to RRnorm.

Authentication was carried out for each of the electrocardiographic waveforms measured for authentication. Three electrocardiographic waveforms are used for each of the six examinees. Accordingly, evaluation was performed for 18 electrocardiographic waveforms in total. To perform the evaluation, the percentage of the number of the electrocardiographic waveforms correctly authenticated (the accuracy rate) was calculated.

FIG. 5 illustrates the result of authentication carried out for the electrocardiographic waveforms of six examinees using the method based on Japanese Patent No. 4782141.

In tables illustrated in FIG. 5, the numbers arranged along the vertical direction at the left end are actual user numbers, and the numbers arranged along the horizontal direction at the upper end are the user numbers output through the authentication. The numbers of correct authentications for each of the users are indicated by the numbers arranged along the diagonal line in the tables illustrated in FIG. 5. The accuracy rate is 72%. As can be seen from FIG. 5, the accuracy of authentication is low in the method based on Japanese Patent No. 4782141.

Figure 6:
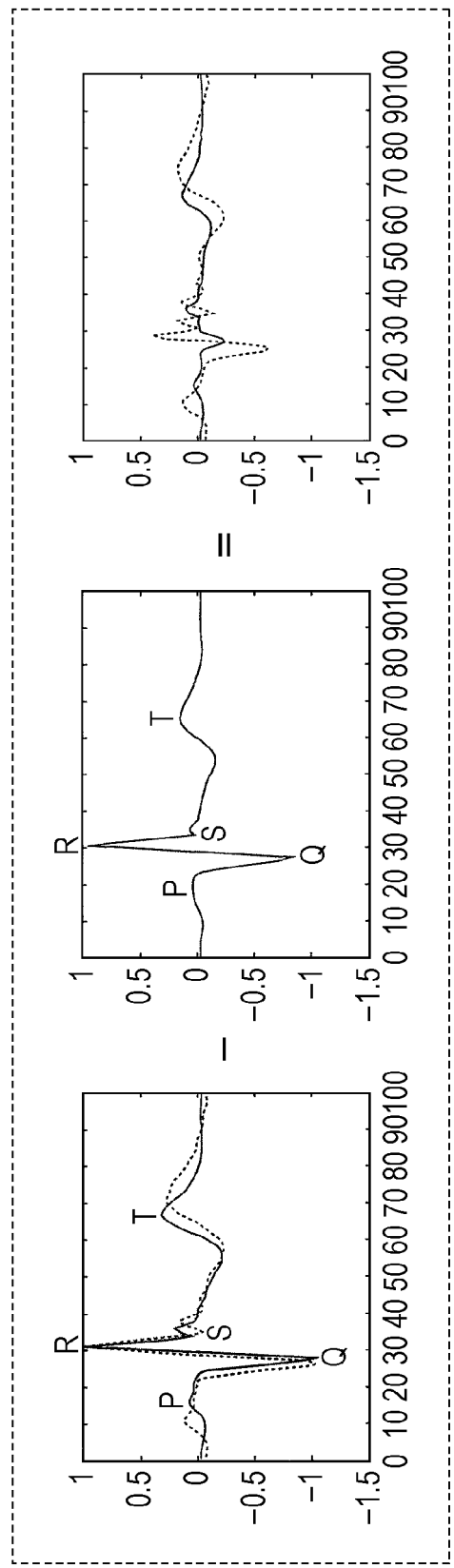
FIG. 6 illustrates an example of wrong authentication in the method based on Japanese Patent No. 4782141.

FIG. 6 illustrates an example of wrong authentication in the method based on Japanese Patent No. 4782141.

A graph on the left illustrated in FIG. 6 indicates the authentication data (a solid line) and the registered data (a broken line) of the examinee 1. The authentication data is an averaged or normalized electrocardiographic waveform generated for one period on the basis of one electrocardiographic waveform measured for authentication. The registered data is an averaged and normalized electrocardiographic waveform generated for one period on the basis of the nine electrocardiographic waveforms measured in advance. A graph in the middle in FIG. 6 indicates the average of the electrocardiographic waveforms of all the users (the overall average). A graph on the right illustrated in FIG. 6 indicates the difference obtained by subtracting the overall average from the authentication data (a solid line) and the difference obtained by subtracting the overall average from the registered data (a broken line).

The correlation between the two differences is 0.23, which is low. The reason is that although the two waveforms are similar to each other as indicated by the graph on the left, the position of the peak of one of the P waves is shifted from the position of the peak of the other P wave, the position of the peak of one of the Q waves is shifted from the position of the peak of the other Q wave, the position of the peak of one of the S waves is shifted from the position of the peak of the other S wave, and the position of the peak of one of the T waves is shifted from the position of the peak of the other T wave.

Since the time period between the peak of a wave other than the R wave and the peak of the R wave is non-linear with respect to the R-R duration, such shift occurs during normalization.

To solve such a problem, a personal authentication apparatus according to an aspect of the present disclosure includes an electrocardiograph measuring circuit that measures the electrocardiographic waveform of a user using a plurality of electrodes in contact with the user, a peak detection unit that detects at least one of a P wave and a Q wave in the electrocardiographic waveform, a peak of a first R wave, and a peak of the second R wave, an acquiring unit that acquires a first normalized electrocardiographic waveform by expanding and contracting the electrocardiographic waveform in the time axis direction and the amplitude direction, and an authentication unit that outputs authentication information regarding a user corresponding to characteristic information that is similar to the characteristic of the first normalized electrocardiographic waveform by referring to identification information regarding a plurality of users and registration information including characteristic information regarding the characteristic of the electrocardiographic waveform corresponding to the identification information regarding each of the users. The acquiring unit expands or contracts the time interval between the peak of the first R wave and the peak of the second R wave to a first predetermined time period, and the acquiring unit (i) expands or contracts the time interval between the peak of the first R wave and the peak of the P wave to a second predetermined time period, (ii) expands or contracts the time interval between the peak of the first R wave and the peak of the Q wave to a third predetermined time period, or (iii) expands or contracts the time interval between the peak of the first R wave and the peak of the P wave to the second predetermined time period and expands or contracts the time interval between the peak of the first R wave and the peak of the Q wave to the third predetermined time period. For example, the characteristic information regarding each of the users contained in the registration information indicates an electrocardiographic waveform.

In this manner, in the first normalized electrocardiographic waveform, the time period between the peak of the first R wave and the peak of the P wave is set to the second predetermined time period, or the time period between the peak of the first R wave and the peak of the Q wave is set to the third predetermined time period. Accordingly, authentication of the electrocardiographic waveform of a user can be carried out without being influenced by the time period between the peak of the first R wave and the peak of the P wave or the time period between the peak of the first R wave and the peak of the Q wave. As a result, for example, an accuracy rate of 94% or 83% can be obtained and, thus, a user (a person) can be authenticated with high accuracy.

Furthermore, authentication of the electrocardiographic waveform of a user can be carried out without being influenced by the time period between the peak of the first R wave and the peak of the Q wave in addition to the time period between the peak of the first R wave and the peak of the P wave. As a result, for example, an accuracy rate of 83% can be obtained and, thus, a user (a person) can be authenticated with high accuracy.

In addition, the peak detection unit may further detect a peak of an S wave in the electrocardiographic waveform, and the acquiring unit further expands or contracts the time interval between the peak of the first R wave and the peak of the S wave to a fourth predetermined time period.

In this manner, the electrocardiographic waveform of the user can be authenticated without being influenced by a period of time between the peak of the first R wave and the peak of the S wave. As a result, for example, an accuracy rate of 94% or 83% can be obtained and, thus, a user (a person) can be authenticated with high accuracy.

In addition, the peak detection unit may further detect a peak of a T wave in the electrocardiographic waveform, and the acquiring unit may further expand or contracts the time interval between the peak of the first R wave and the peak of the T wave to a fifth predetermined time period.

Thus, authentication of the electrocardiographic waveform of a user can be performed without being influenced by the time period between the peak of the first R wave and the peak of the T wave. As a result, for example, an accuracy rate of 89% or 83% can be obtained and, thus, a user (a person) can be authenticated with high accuracy.

In addition, the peak detection unit may further detect a peak of an S wave and a peak of a T wave in the electrocardiographic waveform, and the acquiring unit may expand or contract a time interval between the peak of the first R wave and the peak of the S wave to a fourth predetermined time period in the time axis direction and expand or contract a time interval between the peak of the first R wave and the peak of the T wave to a fifth predetermined time period in the time axis direction.

Thus, authentication of the electrocardiographic waveform of a user can be performed without being influenced by the time period between the peak of the first R wave and the peak of the S wave and the time period between the peak of the first R wave and the peak of the T wave. As a result, for example, an accuracy rate of 94% or 83% can be obtained and, thus, a user (a person) can be authenticated with high accuracy.

In addition, the personal authentication apparatus may further include an input unit that receives input identification information regarding each of a plurality of users to be registered and a registration unit that generates the registration information by associating the identification information regarding the user to be registered received by the input unit with characteristic information indicating the characteristics of the first normalized electrocardiographic waveform acquired by the acquiring unit for the user to be registered.

In this manner, the registration information can be generated using the first normalized electrocardiographic waveform acquired by the acquiring unit. Accordingly, correct registration information can be easily generated.

In addition, the personal authentication apparatus may further include a wavelet transform unit that applies wavelet transform to the first normalized electrocardiographic waveform acquired by the acquiring unit and generates a first matrix and a selection unit that selects at least two elements from the generated first matrix and generates a characteristic vector having the selected at least two elements. The authentication unit may refer to the registration information including a vector as the characteristic information regarding each of the users and output the identification information regarding a user associated with a vector similar to the generated characteristic vector.

In this manner, since the characteristic information included in the registration information is a vector, the amount of data of the registration information can be reduced more than the amount of data of the characteristic information in the form of an electrocardiographic waveform. Accordingly, the capacity of a memory that stores the registration information can be reduced. In addition, for example, an accuracy rate of 100% can be obtained for an electrocardiographic waveform measured for 20 seconds or longer.

In addition, the acquiring unit may further acquire a second normalized electrocardiographic waveform by expanding or contracting the electrocardiographic waveform in the time axis direction and the amplitude direction. In the second normalized electrocardiographic waveform, among the time intervals between the peaks included in the electrocardiographic waveform, only the time interval between the peak of the first R wave and the peak of the second R wave may be expanded or contracted to the first predetermined time period. The personal authentication apparatus may further include a wavelet transform unit that applies wavelet transform to the first normalized electrocardiographic waveform acquired by the acquiring unit to generate a first matrix and applies wavelet transform to the second normalized electrocardiographic waveform acquired by the acquiring unit to generate a second matrix and a selection unit that selects at least one element from each of the first matrix and the second matrix and generates a characteristic vector having the selected at least two elements. The authentication unit may refer to the registration information including a vector as the characteristic information regarding each of the users and output the identification information regarding a user associated with a vector similar to the generated characteristic vector.

In this manner, the wavelet transform is applied to the first normalized electrocardiographic waveform. In addition, the wavelet transform is applied to the second normalized electrocardiographic waveform. Accordingly, the accuracy rate can be increased for even the electrocardiographic waveform measured for, for example, 3 seconds. Thus, a user (a person) can be authenticated in a short time with high accuracy.

In addition, if, in the first normalized electrocardiographic waveform acquired by the acquiring unit, a time interval between a peak to be adjusted representing a peak of at least one wave among the P wave, Q wave, S wave, and T wave and the peak of the first R wave is expanded or contracted to a predetermined time period corresponding to the peak to be adjusted, the characteristic information regarding each of the users included in the registration information may indicate the characteristic of the registered normalized electrocardiographic waveform acquired by expanding or contracting the electrocardiographic waveform of the user in the time axis direction and the amplitude direction, and the time interval between the peak of the first R wave and the peak of the second R wave in the registered normalized electrocardiographic waveform may be the same as that in the first normalized electrocardiographic waveform, and the time interval between each of the at least one peak to be adjusted and the peak of the first R wave in the registered normalized electrocardiographic waveform may be the same as that in the first normalized electrocardiographic waveform.

Thus, the time period between each of at least one of the peaks to be adjusted and the peak of the first R wave in the registered normalized electrocardiographic waveform is the same as that in the first normalized electrocardiographic waveform. Accordingly, authentication for the electrocardiographic waveform of a user can be performed without being influenced by the point in time (the position on the time axis) at which each of at least one peak to be adjusted appears. As a result, a user (a person) can be authenticated with high accuracy.

According to another aspect of the present disclosure, a personal authentication apparatus includes an electrocardiograph measuring circuit that measures an electrocardiographic waveform of a user using a plurality of electrodes in contact with the user, a peak detection unit that detects a plurality of peaks included in the electrocardiographic waveform, an acquiring unit that acquires a normalized electrocardiographic waveform by expanding or contracting the electrocardiographic waveform on the basis of the peaks, and an authentication unit that outputs information for identifying the user on the basis of prerecorded information and the normalized electrocardiographic waveform. The electrocardiographic waveform includes a first waveform and a second waveform that immediately follows the first waveform. The plurality of peaks include a peak of the first R wave included in the first waveform and a peak of the second R wave included in the second waveform. The plurality of peaks further include at least one of a peak of a P wave and a peak of a Q wave included in the first waveform. The first waveform and the second waveform do not include an R wave except the first R wave and the second R wave. The acquiring unit expands or contracts a time interval between the peak of the first R wave and the peak of the second R wave to a first predetermined time period. The acquiring unit performs one of first process, second process, and third process. In the first process, the acquiring unit expands or contracts a time interval between the peak of the first R wave and the peak of the P wave to a second predetermined time period. In the second process, the acquiring unit expands or contracts a time interval between the peak of the first R wave and the peak of the Q wave to a third predetermined time period. In the third process, the acquiring unit expands or contracts the time interval between the peak of the first R wave and the peak of the P wave to the second predetermined time period and expands or contracts the time interval between the peak of the first R wave and the peak of the Q wave to the third predetermined time period. The prerecorded information includes information based on the electrocardiographic waveform of each of the plurality of users including the user. Exemplary embodiments are described in detail below with reference to the accompanying drawings.

Note that each of the embodiments below describes a general or specific example. A value, a shape, a material, a constituent element, the positions and the connection form of the constituent elements, steps, and the sequence of steps used in the embodiments are only examples and shall not be construed as limiting the scope of the present disclosure. In addition, among the constituent elements in the embodiments described below, the constituent element that does not appear in an independent claim, which has the broadest scope, is described as an optional constituent element.

First Exemplary Embodiment

Configuration of Personal Authentication Apparatus

FIG. 7 is a block diagram of the configuration of a personal authentication apparatus according to the first exemplary embodiment.

A personal authentication apparatus 10 includes an electrocardiograph measuring unit 11, a peak detection unit 12, an acquiring unit 13, and an authentication unit 15.

Electrocardiograph Measuring Unit

The electrocardiograph measuring unit 11 measures the electrocardiographic waveform of a user using a plurality of electrodes in contact with the user (i.e., an electrode group). More specifically, the electrocardiograph measuring unit 11 measures the cardiac potential at predetermined sampling intervals and outputs electrocardiographic data indicating the electrocardiographic waveform. The electrocardiographic data indicates the cardiac potential at the sampling periods, that is, at predetermined elapsed times. Accordingly, the electrocardiographic data indicates the time change in the cardiac potential in the form of an electrocardiographic waveform. The electrocardiograph measuring unit 11 is configured as, for example, an electrocardiograph measuring circuit. Note that the electrocardiograph measuring unit 11 may or may not include the electrode group. If the electrocardiograph measuring unit 11 does not include the electrode group, the electrocardiograph measuring unit 11 is electrically connected to each of the electrodes contained in the electrode group.

The electrocardiograph measuring unit 11 having such a configuration measures the electrocardiographic waveform for a predetermined period of time (e.g., 1 to 2 seconds) to obtain the electrocardiographic waveform including an R wave having at least two peaks. For example, the electrocardiograph measuring unit 11 samples the cardiac potential at a sampling frequency of 1024 Hz.

The plurality of electrodes may be in contact with the user so that the heart of the user is located between the electrodes.

For example, any one of the electrodes is in contact with the right hand of the user, and any one of the remaining electrodes is in contact with the left hand of the user. Alternatively, any one of the electrodes is in contact with the right leg of the user, and any one of the remaining electrodes is in contact with the left leg of the user. Alternatively, the electrodes may be in contact with the user by the user holding the electrodes with their both hands. Note that the electrodes may be in contact with the user by bonding the electrodes to the user using an adhesive agent.

Peak Detection Unit

The peak detection unit 12 detects peaks of at least two R waves in the electrocardiographic waveform measured by the electrocardiograph measuring unit 11. In addition, the peak detection unit 12 detects, as a peak to be adjusted, the peak of the P wave in the electrocardiographic waveform measured by the electrocardiograph measuring unit 11. The peak to be adjusted is the peak of one of the P wave, Q wave, S wave, and T wave contained in the electrocardiographic waveform and allows the occurrence time thereof (the position of the peak in the time axis) to be adjusted. The peak to be adjusted is indicated by regulation information stored in a regulation storage unit DB1. According to the present exemplary embodiment, the peak of at least one of the P wave, Q wave, S wave, and T wave contained in the electrocardiographic waveform is selected as a peak to be adjusted. At that time, the peak of at least one of the P and Q waves needs to be selected. Hereinafter, the case in which only the peak of the P wave is selected as a peak to be adjusted is described first. Subsequently, another case, such as the case in which the peak to be adjusted is the peak of each of the P wave, Q wave, S wave, and T wave, is described with reference to FIG. 18A and the subsequent drawings.

As described above, the peak detection unit 12 detects the peaks of two R waves. In addition, the peak detection unit 12 refers to the regulation information and determines the peak of the P wave to be the peak to be adjusted. Thereafter, the peak detection unit 12 detects the peak of the P wave.

For example, the peak detection unit 12 detects, as the peak of the R wave, the peak of a wave having a width of a predetermined value or less at a predetermined potential and having a predetermined maximum potential value or higher in the electrocardiographic waveform. In addition, the peak detection unit 12 detects, as the peak of the P wave, the peak of a wave having its maximum potential value that appears in a predetermined time range prior to the time of the peak of the R wave. Note that the peak detection unit 12 may detect the peak of the R wave and the peak of the P wave on the basis of another existing technique. In addition, the peak detection unit 12 may detect, as the time of the peak of a wave, the time at which the potential of the wave is lower than the maximum potential value of the wave by a predetermined value.

Hereinafter, the peaks of at least two R waves are written as R1 wave, R2 wave, . . . , RN wave (N: an integer) in the order in which they appear in the electrocardiographic waveform. The peak of the N-th R wave is referred to as a "first R wave", and the peak of the (N+1)th R wave is referred to as a "second R wave". The time duration between the first R wave and the second R wave is referred to as an "R-R duration". Alternatively, the peak detection unit 12 may detect a peak of the S wave, a peak of the T wave, a peak of the P wave, and a peak of the Q wave in each of the R-R durations.

Acquiring Unit

The acquiring unit 13 expands or contracts the measured electrocardiographic waveform in the time axis direction and the amplitude direction on the basis of the peaks of the waves detected by the peak detection unit 12 and acquires a normalized electrocardiographic waveform (a first normalized electrocardiographic waveform).

When expanding or contracting the electrocardiographic waveform in the time axis direction, the acquiring unit 13 refers to the regulation information stored in the regulation storage unit DB1 and selects the P wave as the peak to be adjusted. In addition, the acquiring unit 13 determines a predetermined time period (a second predetermined time period) for the peak of the P wave. The second predetermined time period represents the time interval between the peak of the first R wave and the peak to be adjusted. The acquiring unit 13 expands or contracts the time interval between the peak of the first R wave and the peak of the second R wave in the electrocardiographic waveform to a predetermined time period RRnorm (a first predetermined time period). In addition, the acquiring unit 13 expands or contracts the time interval between the peak of the first R wave and the peak of the P wave, which is the peak to be adjusted, in the electrocardiographic waveform to the second predetermined time period.

When expanding or contracting the electrocardiographic waveform in the amplitude direction, the acquiring unit 13 divides the potential in the first duration in the electrocardiographic waveform that is expanded or contracted in the time axis direction by the peak value of the first R wave and divides the potential in the second duration in the electrocardiographic waveform by the peak value of the second R wave. In this manner, the electrocardiographic waveform is expanded or contracted in the amplitude direction. In addition, if, for example, information indicating a predetermined magnitude of the potential is stored in the regulation storage unit DB1, the acquiring unit 13 may expand or contract the electrocardiographic waveform in the amplitude direction using the information. The information indicates, for example, a magnitude of potential of V0. In such a case, the acquiring unit 13 multiplies the potential in the first duration of the electrocardiographic waveform expanded or contracted in the time axis direction by V0/(the peak value of the first R wave). In addition, the acquiring unit 13 multiplies the potential in the second duration of the electrocardiographic waveform by V0/(the peak value of the second R wave). Thus, the electrocardiographic waveform is expanded or contracted in the amplitude direction so that the highest potential of the expanded or contracted electrocardiographic waveform is set to V0.

Authentication Unit

The authentication unit 15 refers to the registration information stored in a registration storage unit DB2 and authenticates a user having the normalized electrocardiographic waveform acquired by the acquiring unit 13. Note that the registration information includes identification information regarding a plurality of users and the characteristic information indicating the characteristics of the electrocardiographic waveform corresponding to the identification information regarding each of the users. According to the present exemplary embodiment, the characteristic information is the electrocardiographic waveform registered for the user (a registered electrocardiographic waveform). In addition, authentication of a user includes outputting the identification information regarding one of the users from the identification information regarding the plurality of users contained in the registration information. Through such authentication, a user having the electrocardiographic waveform measured by the electrocardiograph measuring unit 11 can be identified.

For example, the authentication unit 15 selects, from among a plurality of registered electrocardiographic waveforms contained in the registration information, a registered electrocardiographic waveform that is the most similar to or that has the highest correlation with the normalized electrocardiographic waveform acquired by the acquiring unit 13 and outputs the user identification information associated with the selected registered electrocardiographic waveform. Alternatively, the authentication unit 15 calculates the similarity between each of the plurality of registered electrocardiographic waveforms contained in the registration information and the normalized electrocardiographic waveform acquired by the acquiring unit 13 and selects the registered electrocardiographic waveform having the highest similarity among the similarities each higher than or equal to a predetermined similarity. Thereafter, the authentication unit 15 outputs the user identification information associated with the selected registered electrocardiographic waveform. The predetermined similarity may be indicated by the registration information in the registration storage unit DB2 or be indicated by information other than the registration information stored in the registration storage unit DB2. Alternatively, the authentication unit 15 may store information indicating the predetermined similarity. Still alternatively, the authentication unit 15 may read the information from a recording medium provided in the personal authentication apparatus 10.

In addition, if all the similarities calculated for the plurality of registered electrocardiographic waveforms contained in the registration information are lower than the predetermined similarity, the authentication unit 15 may output information indicating that user authentication is unavailable. That is, the authentication unit 15 may output information indicating that the acquired normalized electrocardiographic waveform is not related to any one of the users having the registered identification information.

Regulation Storage Unit

FIG. 8 illustrates an example of the regulation information according to the first exemplary embodiment.

The regulation information stored in the regulation storage unit DB1 indicates a peak to be adjusted and the predetermined time period corresponding to the peak to be adjusted. The peak to be adjusted is the peak of the P wave. The predetermined time period is the second predetermined time period and is, for example, 0.85×RRnorm. Note that the coefficient to be multiplied by RRnorm to indicate the predetermined time period of the P wave may be a value in the range of 0.79 to 0.94, instead of 0.85.

Registration Storage Unit

FIG. 9 illustrates an example of the registration information according to the first exemplary embodiment.

The registration information stored in the registration storage unit DB2 contains the identification information regarding a plurality of users and the characteristic information indicating the characteristics of the electrocardiographic waveform corresponding to the identification information regarding each of the plurality of users. According to the present exemplary embodiment, the characteristic information is the above-described registered electrocardiographic waveform, which is the normalized registered electrocardiographic waveform of a user. The registered electrocardiographic waveform is formed from points in time and the magnitudes of the cardiac potential at the points in time. The identification information regarding a user includes information that allows a person to be identified, such as the name, the age, or the weight of the user.

In addition, the registration information may indicate the number of the R-R durations for each of the users. The number of the R-R durations is the number of the R-R durations contained in the electrocardiographic waveform of the user measured by the electrocardiograph measuring unit 11 when the registered electrocardiographic waveform is generated. The number of the R-R durations is used to calculate the average of the registered electrocardiographic waveforms of all the users (the overall average) described below.

In the registered electrocardiographic waveform, the above-described shift operation may or may not be performed so that the P wave, Q wave, R wave, S wave, and T wave are arranged in this order.

Figure 10:
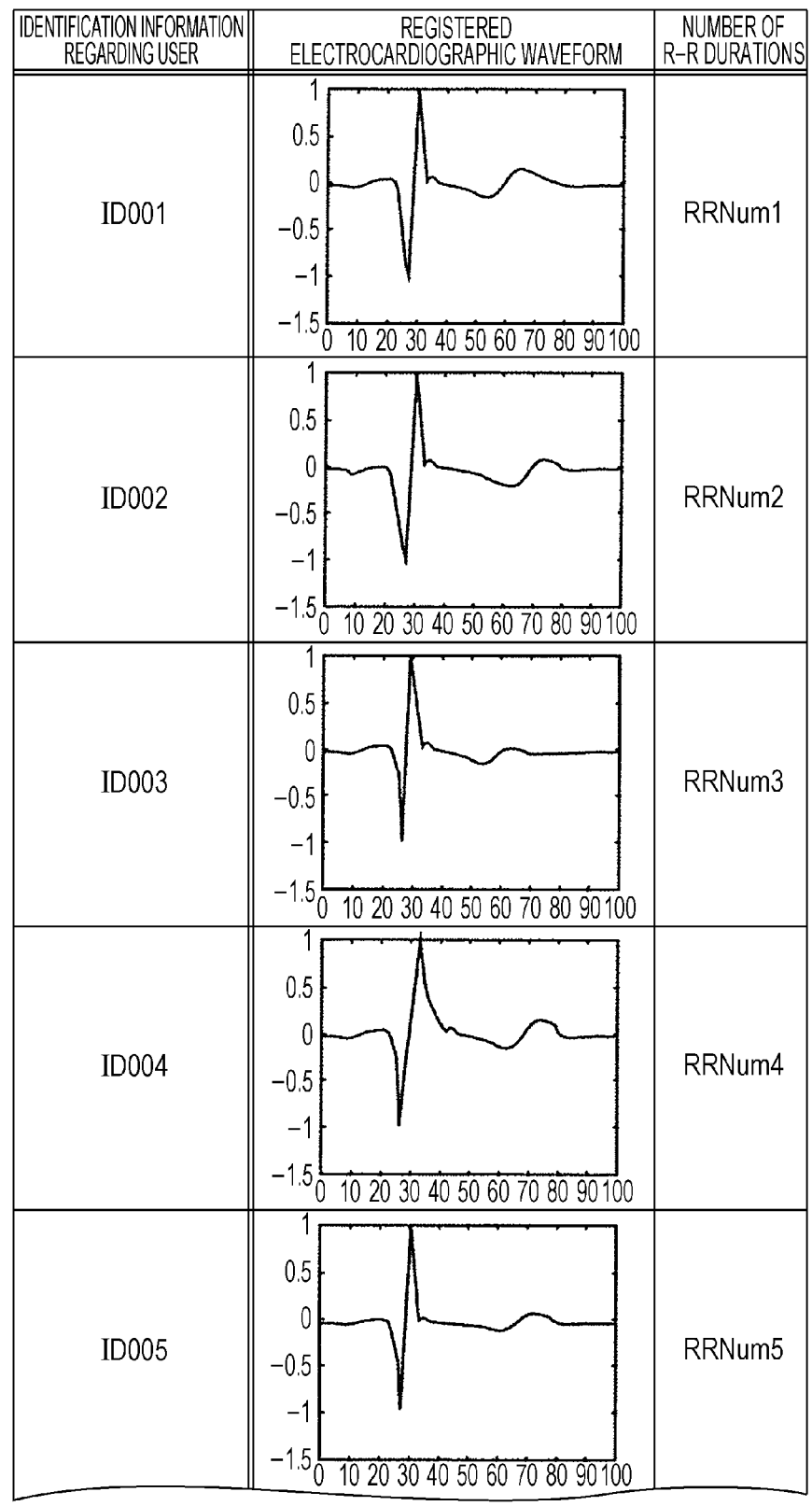
FIG. 10 illustrates another example of the registration information according to the first exemplary embodiment.

FIG. 10 illustrates another example of the registration information according to the first exemplary embodiment.

Instead of indicating a registered electrocardiographic waveform by using specific points in time and the cardiac potentials at the points in time as illustrated in FIG. 9, the normalized electrocardiographic waveform itself may be used as the registered electrocardiographic waveform as illustrated in FIG. 10. Even in such a case, the above-described shift operation may or may not be performed so that the P wave, Q wave, R wave, S wave, and T wave are arranged in this order in the registered electrocardiographic waveform.

In addition, the registered electrocardiographic waveform according to the present exemplary embodiment is an electrocardiographic waveform normalized by expanding or contracting the user electrocardiographic waveform in the time axis direction and the amplitude direction. Furthermore, if the user electrocardiographic waveform measured by the electrocardiograph measuring unit 11 in order to generate the registered electrocardiographic waveform contains a plurality of R-R durations, the normalized electrocardiographic waveforms equal in number to the number of R-R durations are averaged. The averaged electrocardiographic waveform serves as the above-described registered electrocardiographic waveform. In addition, the time period between the peak of the first R wave and the peak to be adjusted (the peak of the P wave) in the registered electrocardiographic waveform is the same as the above-described second predetermined time period.

Figure 11:
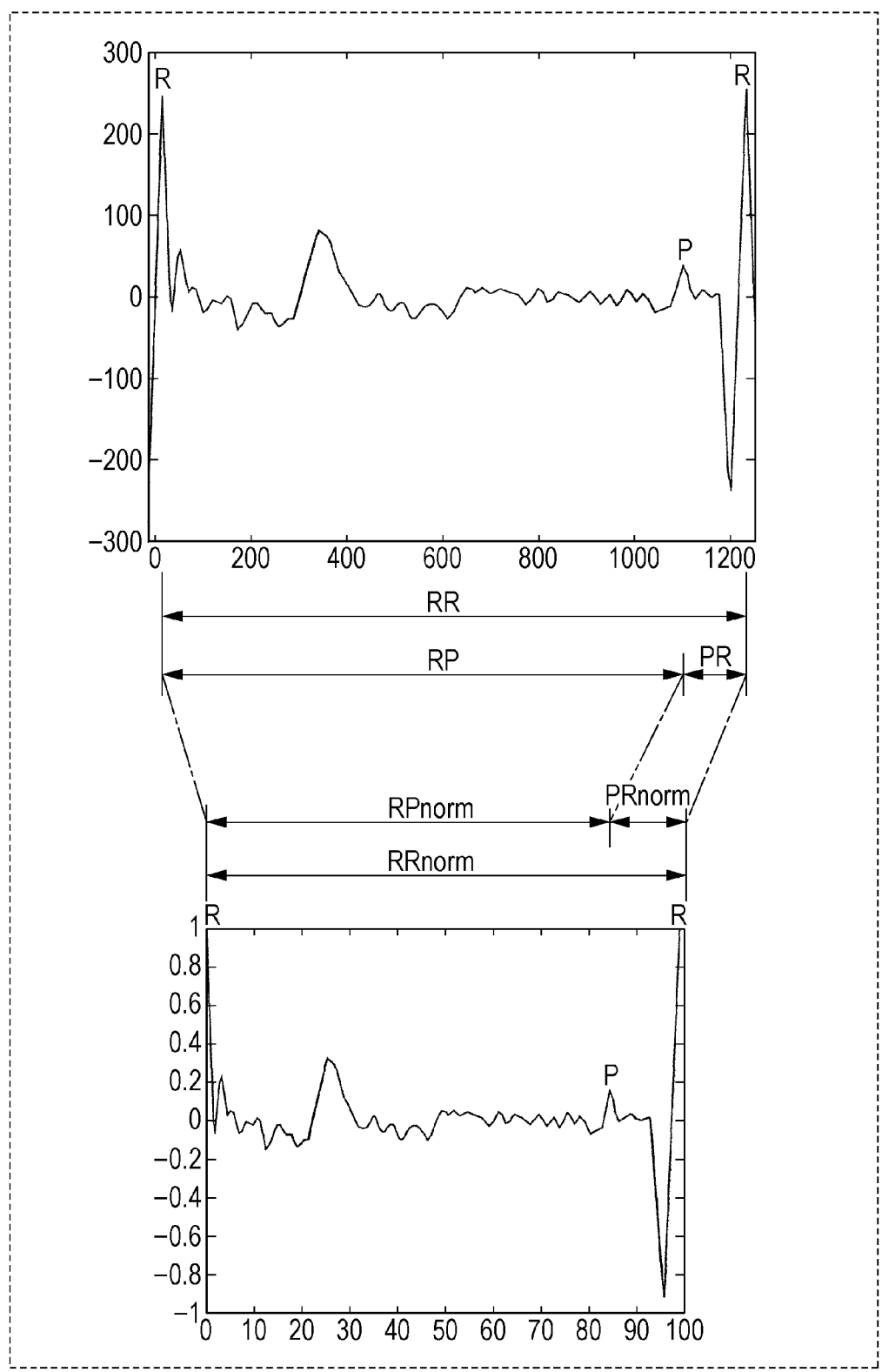
FIG. 11 illustrates an example of normalization according to the first exemplary embodiment.

FIG. 11 illustrates an example of normalization according to the first exemplary embodiment.

The acquiring unit 13 normalizes the electrocardiographic waveform in the R-R duration by expanding or contracting the electrocardiographic waveform in the time axis direction and the amplitude direction.

More specifically, the acquiring unit 13 separates the electrocardiographic waveform in the R-R duration into an electrocardiographic waveforms in an R-P duration between the peak of the first R wave and the peak of the P wave and a P-R duration between the peak of the P wave and the peak of the second R wave. Thereafter, the acquiring unit 13 expands or contracts the electrocardiographic waveform in each of the durations so that the time period of the R-R duration is the same as a first predetermined time period RRnorm, the time period of the R-P duration is the same as a second predetermine time period RPnorm, and the time period of the P-R duration is the same as a predetermine time period PRnorm. Note that the first predetermined time period RRnorm is, for example, the time period for 100 samples. The second predetermine time period RPnorm is the time period for 0.85×100 (=85) samples, as indicated by the regulation information in FIG. 8. In addition, the predetermine time period PRnorm is a time period obtained by subtracting the second predetermine time period RPnorm from the first predetermined time period RRnorm and is a time period for 100–85 (=15) samples. In this manner, the peak to be adjusted, which is the peak of the P wave, is adjusted so as to occur at a predetermined point in time. That is, the peak to be adjusted is aligned so that the time period between the peak to be adjusted and the peak of the first R wave is set to a predetermined time period. To align the peak to be adjusted, the linear interpolation given by the above-described equations (1) and (2) is used as a method for expanding or contracting the electrocardiographic waveform in the time axis direction.

Figure 12:
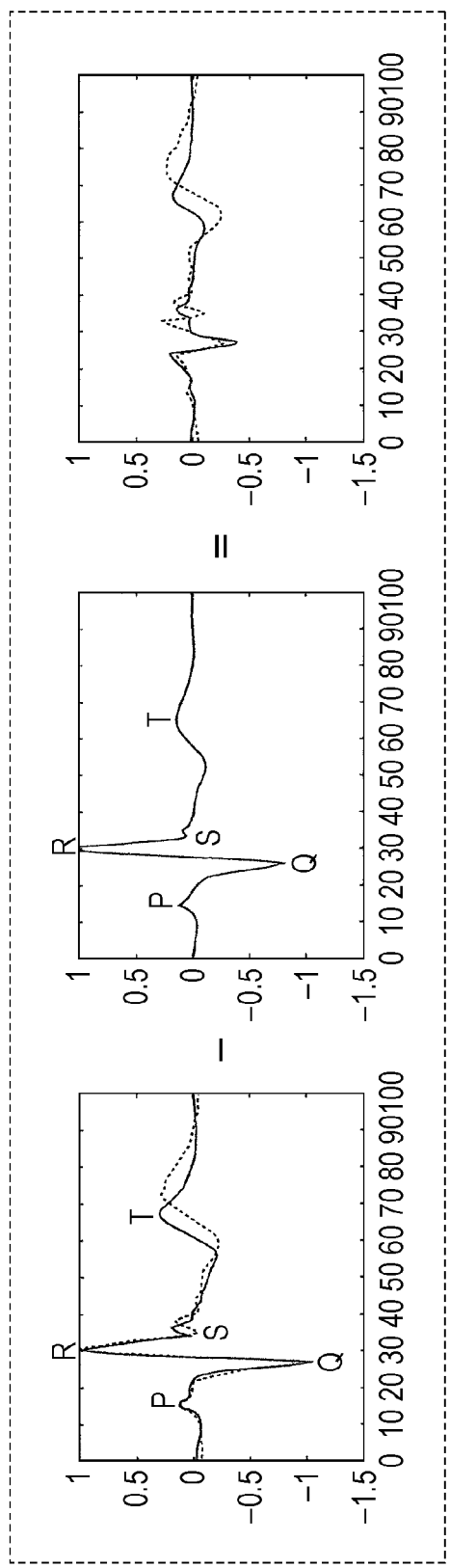
FIG. 12 illustrates an example of a correlation between two electrocardiographic waveforms according to the first exemplary embodiment.

FIG. 12 illustrates an example of a correlation between two electrocardiographic waveforms according to the first exemplary embodiment.

A graph on the left illustrated in FIG. 12 indicates the normalized electrocardiographic waveform of a user acquired by the acquiring unit 13 (a solid line) and the registered electrocardiographic waveform of the user (a broken line). For example, the user is the examinee 1 illustrated in FIG. 5. A graph in the middle illustrated in FIG. 12 indicates the average of the registered electrocardiographic waveforms of all the users (the overall average). A graph on the right illustrated in FIG. 12 indicates the difference obtained by subtracting the overall average from the normalized electrocardiographic waveform (a solid line) and the difference obtained by subtracting the overall average from the registered electrocardiographic waveform (a broken line). The correlation between the differences is 0.49, which is high. Accordingly, since the correlation between the acquired normalized electrocardiographic waveform and the registered electrocardiographic waveform of the examinee 1 is the highest among the correlations between the acquired normalized electrocardiographic waveform and the registered electrocardiographic waveform of the examinees 1 to 6, the identification information regarding the examinee 1 can be correctly output for the acquired normalized electrocardiographic waveform. Note that the correlation is represented in the form of, for example, the Pearson product-moment correlation coefficient.

Processing Flow of Authentication Phase

Figure 13:
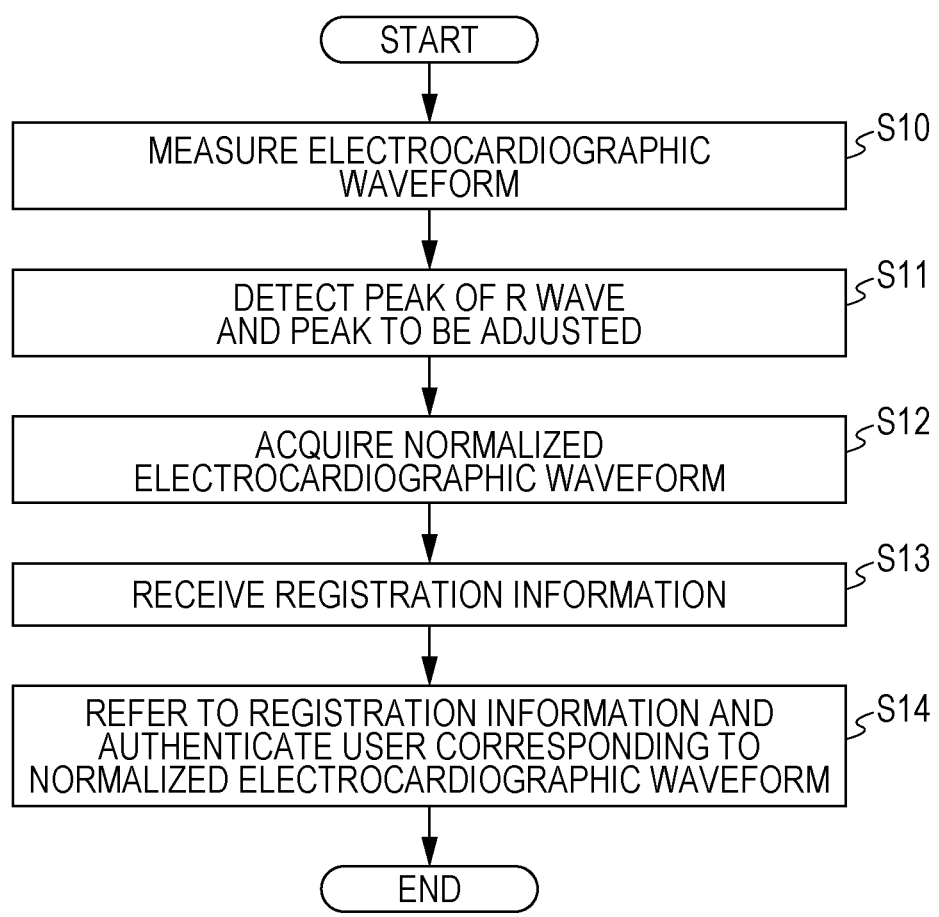
FIG. 13 is a flowchart of a processing operation performed by the personal authentication apparatus in an authentication phase according to the first exemplary embodiment.

FIG. 13 is a flowchart of a processing operation performed by the personal authentication apparatus 10 in the authentication phase according to the first exemplary embodiment.

The electrocardiograph measuring unit 11 measures the electrocardiographic waveform of a user using a plurality of electrodes in contact with the user first (step S10).

The peak detection unit 12 detects, from the electrocardiographic waveform measured in step S10, the peaks of the first R wave and the second R wave of the electrocardiographic waveform. In addition, the peak detection unit 12 detects the peak of the P wave as the peak to be adjusted (step S11).

The acquiring unit 13 acquires the normalized electrocardiographic waveform by expanding or contracting the electrocardiographic waveform in the time axis direction and the amplitude direction on the basis of the detected peaks (step S12). At that time, the acquiring unit 13 expands or contacts the electrocardiographic waveform in the time axis direction so that the time period between the peak of the first R wave and the peak of the second R wave in the electrocardiographic waveform is the same as the first predetermined time period (RRnorm). In addition, the acquiring unit 13 expands or contracts the time period between the peak of the first R wave and the peak of the P wave, which is the peak to be adjusted, in the normalized electrocardiographic waveform to the second predetermined time period. That is, the acquiring unit 13 aligns the peaks of the P wave.

In addition, if a plurality of the R-R durations are included in the electrocardiographic waveform measured in step S10, the acquiring unit 13 acquires the averaged normalized electrocardiographic waveform in step S12. That is, the acquiring unit 13 generates the normalized electrocardiographic waveform for each of the R-R durations. Thereafter, the acquiring unit 13 calculates the average of the normalized electrocardiographic waveforms equal in number to the number of the R-R durations and obtains the averaged normalized electrocardiographic waveform.

The authentication unit 15 receives the registration information stored in the registration storage unit DB2 (step S13). Subsequently, the authentication unit 15 refers to the registration information received in step S13 and selects the registered electrocardiographic waveform similar to the acquired normalized electrocardiographic waveform acquired in step S12. Thereafter, the authentication unit 15 outputs the identification information regarding the user associated with the selected registered electrocardiographic waveform. That is, the authentication unit 15 outputs the identification information regarding the user associated with the registered electrocardiographic waveform having the characteristics similar to those of the acquired normalized electrocardiographic waveform.

Processing Flow of Acquiring Unit

Figure 14:
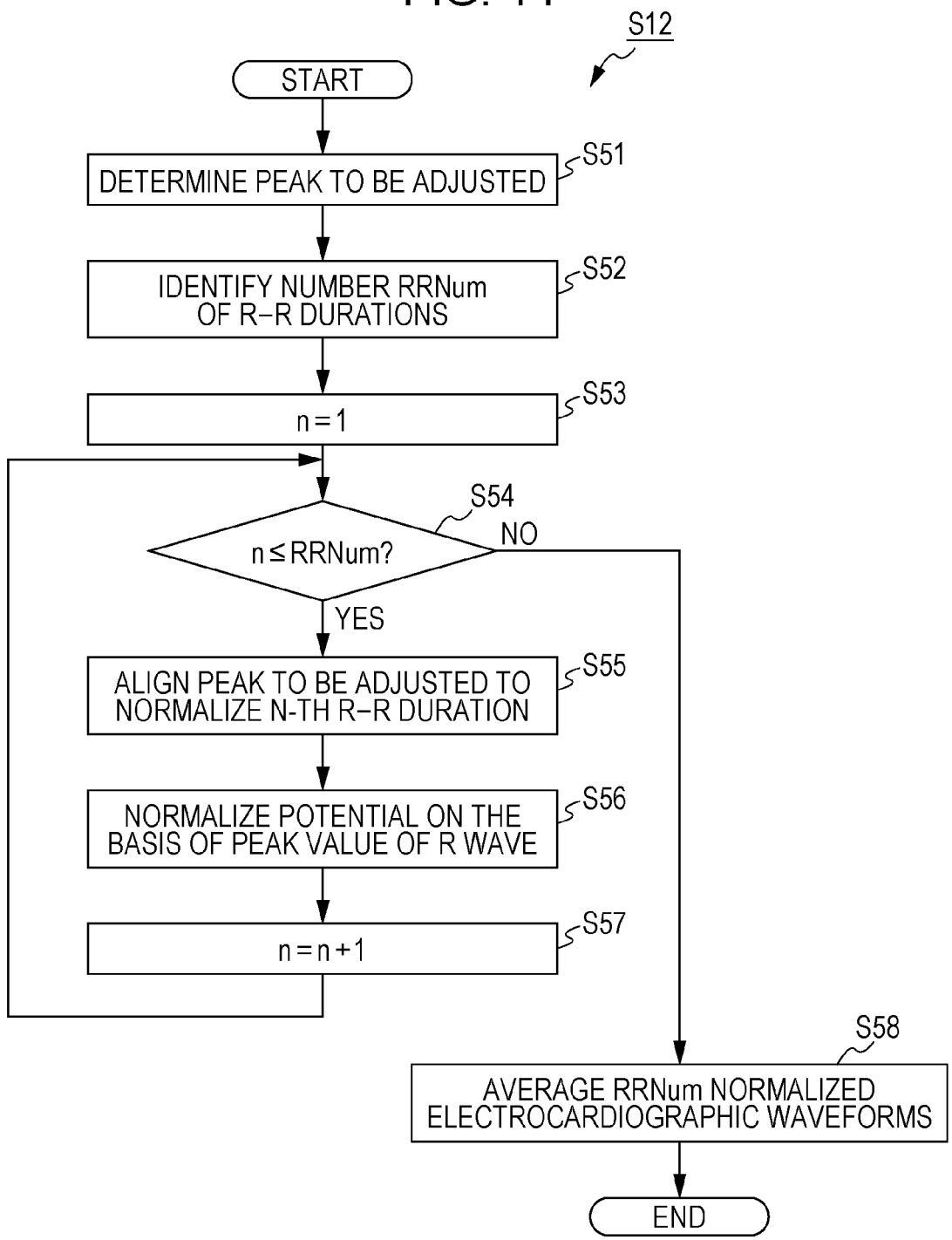
FIG. 14 is a flowchart of the processing operation performed by an acquiring unit according to the first exemplary embodiment.

FIG. 14 is a flowchart of the processing operation performed by the acquiring unit 13 according to the first exemplary embodiment. That is, FIG. 14 is a flowchart of the detailed process in step S12 illustrated in FIG. 13.

The acquiring unit 13 refers to the regulation information stored in the regulation storage unit DB1 and determines the peak to be aligned, that is, the peak to be adjusted (e.g., the peak of the P wave) from among the peak of the P wave, the peak of the Q wave, the peak of the S wave, and the peak of the T wave (step S51). Thereafter, the acquiring unit 13 identifies the number RRNum of the R-R durations contained in the electrocardiographic waveform on the basis of the peaks of the R wave detected in step S11 illustrated in FIG. 13 (step S52). Subsequently, the acquiring unit 13 initializes a counter n (a value) to 1 (step S53).

Subsequently, the acquiring unit 13 determines whether the counter n is less than or equal to the number RRNum (step S54). If it is determined that the counter n is less than or equal to the number RRNum (Yes in step S54), the acquiring unit 13 expands or contracts the electrocardiographic waveform in the time axis direction and aligns the peak to be adjusted determined in step S51. Thus, the acquiring unit 13 normalizes the n-th R-R duration of the electrocardiographic waveform (step S55). In addition, the acquiring unit 13 normalizes each of the potentials in the R-R duration through expansion or contraction in the amplitude direction on the basis of the peak value of the R wave in the n-th R-R duration (step S56). In this manner, the normalized electrocardiographic waveform in the n-th R-R duration is generated. Furthermore, the acquiring unit 13 increments the counter n by one (step S57) and repeatedly performs the process in step S54 and the subsequent processes.

However, if, in step S54, the acquiring unit 13 determines that the counter n is not less than or equal to the number RRNum (No in step S54), the acquiring unit 13 averages the normalized electrocardiographic waveforms equal in number to the number RRNum (step S58). In this manner, the averaged normalized electrocardiographic waveform can be obtained.

At that time, the acquiring unit 13 may shift the averaged normalized electrocardiographic waveform. That is, the acquiring unit 13 shifts part of the averaged normalized electrocardiographic waveform to the top end of the remaining part. The part of the waveform is a waveform in the time range from the time indicated by (ratio3×RRnorm) to the time indicated by RRnorm. The remaining waveform is a waveform in the time range from the time 0 to the time indicated by (ratio3×RRnorm). Note that RRnorm represents the above-described first predetermined time period, and the time indicated by RRnorm is the point in time when RRnorm has elapsed from 0. Similarly, the time indicated by (ratio3×RRnorm) is the point in time when (ratio3×RRnorm) has elapsed from 0. In addition, ratio3 is, for example, 0.7. In this manner, in the averaged normalized electrocardiographic waveform, the P wave, Q wave, R wave, S wave, and T wave are arranged in this order. Note that the shift operation is optional.

Processing Flow of Expansion or Contraction in Time Axis Direction

Figure 15:
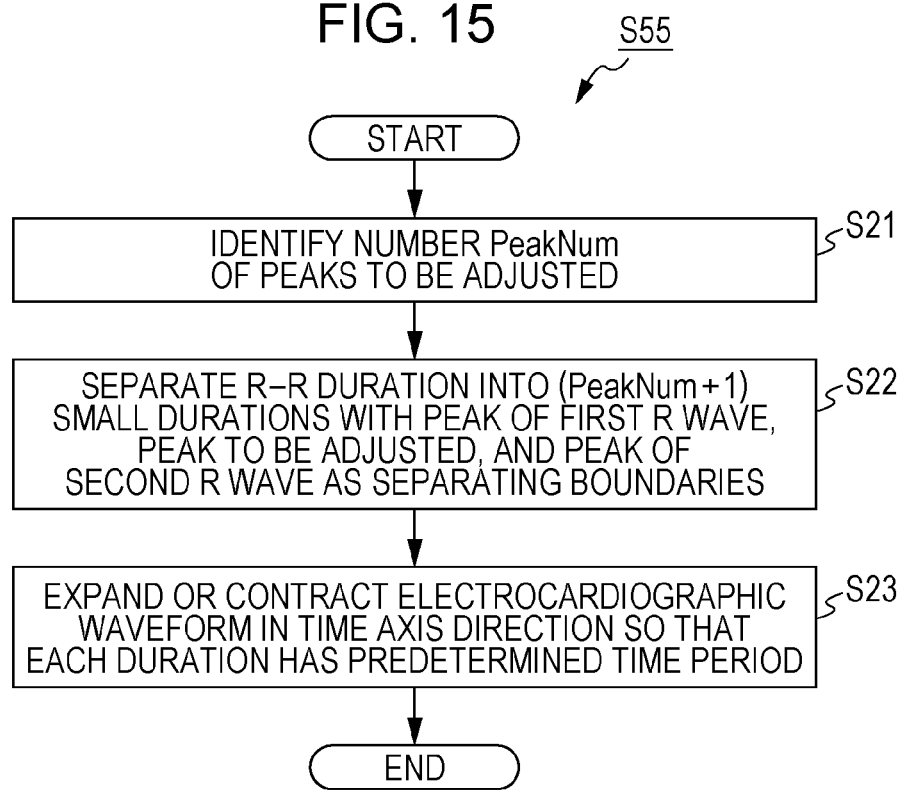
FIG. 15 is a flowchart of the processing operation of expansion or contraction performed by the acquiring unit in the time axis direction according to the first exemplary embodiment.

FIG. 15 is a flowchart of the processing operation of expansion or contraction performed by the acquiring unit 13 in the time axis direction according to the first exemplary embodiment. That is, FIG. 15 is a flowchart of detailed processing in step S55 illustrated in FIG. 14.

The acquiring unit 13 identifies the number PeakNum of the peaks to be adjusted determined in step S51 illustrated in FIG. 14 (step S21). For example, if the peak to be adjusted is only the peak of the P wave, the acquiring unit 13 identifies the number PeakNum as "1".

Subsequently, the acquiring unit 13 separates the R-R duration into (the number PeakNum+1) small durations so that each of the peak of the first R wave detected in step S11 illustrated in FIG. 13, the peak to be adjusted, and the peak of the second R wave serves as a boundary (step S22).

Subsequently, the acquiring unit 13 expands or contracts the electrocardiographic waveform in the time axis direction on the basis of the regulation information so that each of the small durations has a predetermined period of time (step S23). In this manner, the electrocardiographic waveform in the R-R duration is expanded or contracted in the time axis direction and is normalized. That is, normalization in the time axis direction is performed.

Processing Flow of Expansion or Contraction in Amplitude Direction

Figure 16:
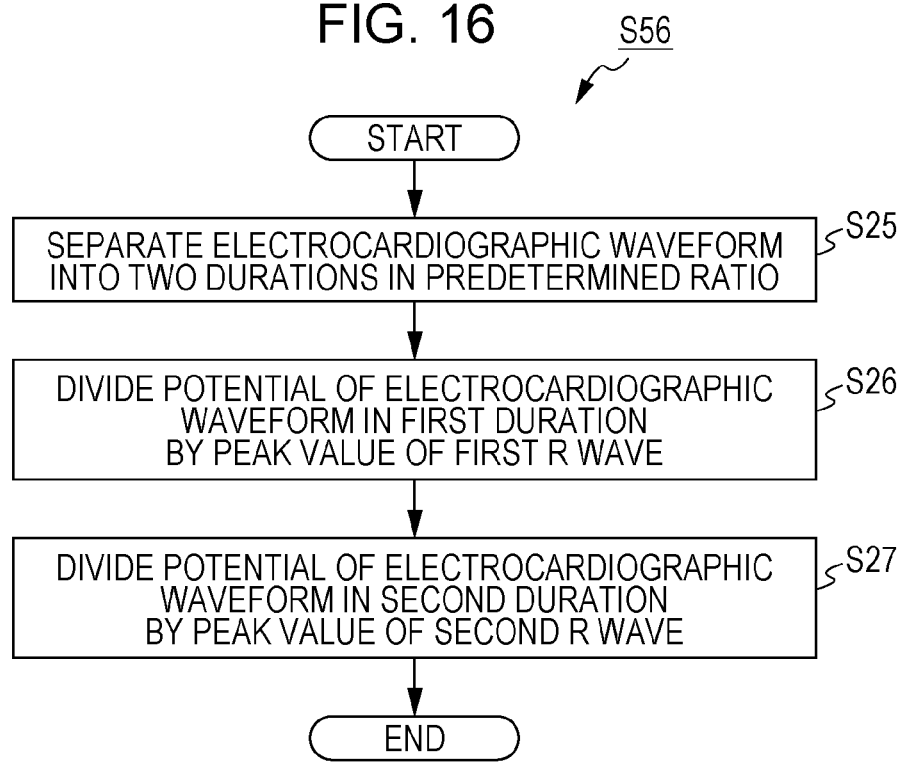
FIG. 16 is a flowchart of the processing operation of expansion or contraction performed by the acquiring unit in the amplitude direction according to the first exemplary embodiment.

FIG. 16 is a flowchart of the processing operation of expansion or contraction performed by the acquiring unit 13 in the amplitude direction according to the first exemplary embodiment. That is, FIG. 16 is a flowchart of detailed processing in step S56 illustrated in FIG. 14.

The acquiring unit 13 separates the electrocardiographic waveform normalized through the expansion or contraction in the time axis direction performed in step S55 illustrated in FIG. 14 into waveforms in two durations using the predetermined ratio ratio3 (step S25). That is, the acquiring unit 13 separates the electrocardiographic waveform into a waveform in the first duration and a waveform in the second duration. The first duration is a duration from the time 0 to the time indicated by (ratio3×RRnorm). The second duration is a duration from the time indicated by (ratio3×RRnorm) to the time indicated by RRnorm.

Subsequently, the acquiring unit 13 divides the potentials of the electrocardiographic waveform in the first duration by the peak value of the first R wave (step S26).

Thereafter, the acquiring unit 13 divides the potentials of the electrocardiographic waveform in the second duration by the peak value of the second R wave (step S27). In this manner, the electrocardiographic waveform in the R-R duration is expanded or contracted in the amplitude direction (or the height direction) and is normalized. That is, normalization in the amplitude direction is performed.

Processing Flow of Authentication Unit

FIG. 17 is a flowchart of the processing operation performed by the authentication unit 15 according to the first exemplary embodiment. That is, FIG. 17 is a flowchart of detailed processing in step S14 illustrated in FIG. 13.

The authentication unit 15 calculates the average of the registered electrocardiographic waveforms of all the users (the overall average) on the basis of the registration information received in step S13 illustrated in FIG. 13 using the above-described equation (3) (step S30).

The authentication unit 15 generates the signature corresponding to the identification information regarding each of the registered users on the basis of the registration information received in step S13 illustrated in FIG. 13. That is, the authentication unit 15 generates the signatures of all the registered users (step S31). More specifically, the authentication unit 15 subtracts the overall average calculated in step S30 from the registered electrocardiographic waveform in the user identification information corresponding to each of the users. The obtained difference serves as the signature.

The authentication unit 15 generates the signature of the acquired normalized electrocardiographic waveform acquired in step S12 illustrated in FIG. 13 (more specifically, the averaged normalized electrocardiographic waveform) (step S32). That is, the authentication unit 15 subtracts the overall average calculated in step S30 from the acquired normalized electrocardiographic waveform. Thus, the authentication unit 15 defines the difference as the signature of the acquired normalized electrocardiographic waveform.

The authentication unit 15 calculates the correlation between the signature generated in step S32 and the signature of each of the users generated in step S31 (step S33). Thereafter, the authentication unit 15 searches the registration information for the identification information regarding the user corresponding to the signature having the highest correlation among the correlations calculated in step S33 (step S34).

Note that in the above-described example, the peak to be adjusted is only the peak of the P wave. However, the peak of at least one of the P wave, Q wave, S wave, and T wave contained in the electrocardiographic waveform may be selected as a peak to be adjusted. At that time, the peak of at least one of the P and Q waves needs to be selected. For example, the peak of each of the P wave, Q wave, S wave, and T wave may be selected as the peak to be adjusted.

Another Example of Regulation Storage Unit

FIG. 18A illustrates another example of the regulation information according to the first exemplary embodiment.

The regulation information stored in the regulation storage unit DB1 indicates each of the peaks to be adjusted and a predetermined time period corresponding to the peak. The peak to be adjusted is the peak of each of the P wave, Q wave, S wave, and T wave. In addition, the regulation information indicates 0.85×RRnorm as the predetermined time period corresponding to the peak of the P wave (the second predetermined time period) and indicates 0.95×RRnorm as the predetermined time period corresponding to the peak of the Q wave (the third predetermined time period). Furthermore, the regulation information indicates 0.05×RRnorm as the predetermined time period corresponding to the peak of the S wave (the fourth predetermined time period) and indicates 0.35×RRnorm as the predetermined time period corresponding to the peak of the T wave (the fifth predetermined time period).

Note that the coefficient to be multiplied by RRnorm to indicate the predetermined time period corresponding to the peak of the P wave (the second predetermined time period) may be a value in the range of 0.79 to 0.94, instead of 0.85. Similarly, the coefficient to be multiplied by RRnorm to indicate the predetermined time period corresponding to the peak of the Q wave (the third predetermined time period) may be a value in the range of 0.95 to 0.98, instead of 0.95. Similarly, the coefficient to be multiplied by RRnorm to indicate the predetermined time period corresponding to the peak of the S wave (the fourth predetermined time period) may be a value in the range of 0.01 to 0.07, instead of 0.05. Similarly, the coefficient to be multiplied by RRnorm to indicate the predetermined time period corresponding to the peak of the T wave (the fifth predetermined time period) may be a value in the range of 0.26 to 0.43, instead of 0.35.

The peak detection unit 12 refers to the regulation information and determines the peaks of the P wave, Q wave, S wave, and T wave as the peaks to be adjusted. Thereafter, the peak detection unit 12 detects the peaks.

For example, as described above, the peak detection unit 12 detects, as the peak of the R wave, a peak of the wave having a width less than a threshold value at a predetermined potential and having a maximum value of the potential higher than or equal to a threshold value in the electrocardiographic waveform. Thereafter, the peak detection unit 12 detects the peak of each of the P wave, Q wave, S wave, and T wave on the basis of the detected peak of the R wave. More specifically, the peak detection unit 12 detects, as the peak of the P wave, a peak appearing in a predetermined time range prior to the time of the peak of the R wave and having the maximum value of the potential. In addition, the peak detection unit 12 detects, as the peak of the T wave, a peak appearing in a predetermined time range subsequent to the time of the peak of the R wave and having the maximum value of the potential. Furthermore, the peak detection unit 12 detects, as the peak of the Q wave, a peak appearing prior to the time of the peak of the R wave and having the minimum value of the potential and detects, as the peak of the S wave, a peak appearing subsequent to the time of the peak of the R wave and having the minimum value of the potential. Note that the peak detection unit 12 may detect the peaks of the P wave, the Q wave, the R wave, the S wave, and the T wave on the basis of another existing technique. In addition, the peak detection unit 12 may detect, as the time of the peak of a wave, the time of the wave that indicates a potential that is lower or higher than the maximum value or the minimum value of the potential by a predetermined value.

FIG. 18B illustrates how the predetermined time periods in the regulation information are determined according to the first exemplary embodiment.

As illustrated in FIG. 18B(a), 12 electrocardiographic waveforms obtained through 12 measurements for each of the six examinees vary from one another. That is, the point in time at which the peak of each of the P wave, the Q wave, the R wave, the S wave, and the T wave in the electrocardiographic waveforms appear varies. In addition, even in a plurality of electrocardiographic waveforms acquired from one person, the times at which the peaks of each of the P wave, the Q wave, the R wave, the S wave, and the T wave in the electrocardiographic waveforms appear vary from one another. Note that in FIG. 18B(a), RS/RR represents the ratio of the duration between the peak of the first R wave and the peak of the S wave in the R-R duration to the R-R duration. Similarly, RT/RR represents the ratio of the duration from the peak of the first R wave to the peak of the T wave in the R-R duration to the R-R duration. RP/RR represents the ratio of the duration from the peak of the first R wave to the peak of the P wave in the R-R duration to the R-R duration. RQ/RR represents the ratio of the duration from the peak of the first R wave to the peak of the Q wave in the R-R duration to the R-R duration.

As illustrated in FIG. 18B(b), the average and the standard deviation of the ratios for each of the peaks are calculated on the basis of the statistical results of the points in time at which the peaks appear. In addition, as illustrated in FIG. 18B(c), "the average−(2×the standard deviation)" and "the average+(2×the standard deviation)" are calculated for the ratio of each of the peaks. As a result, as illustrated in FIG. 18B(d), it is determined that the ratio for each of the peaks is in the range from "the average−(2×the standard deviation)" to "the average+(2×the standard deviation)".

The regulation information indicates, as the predetermined period of time, the product of the ratio within the range indicated in FIG. 18B(d) and RRnorm representing the time period of the R-R duration. Accordingly, since the regulation information indicates an appropriate predetermined time period for each of the peaks, the occurrence of each of the peaks at an inappropriate point in time caused by expansion or contraction in the time axis direction on the basis of the regulation information can be prevented. As a result, a decrease in accuracy of authentication caused by a change in the time of each of the peaks due to the expansion or contraction in the time axis direction can be prevented.

Figure 19:
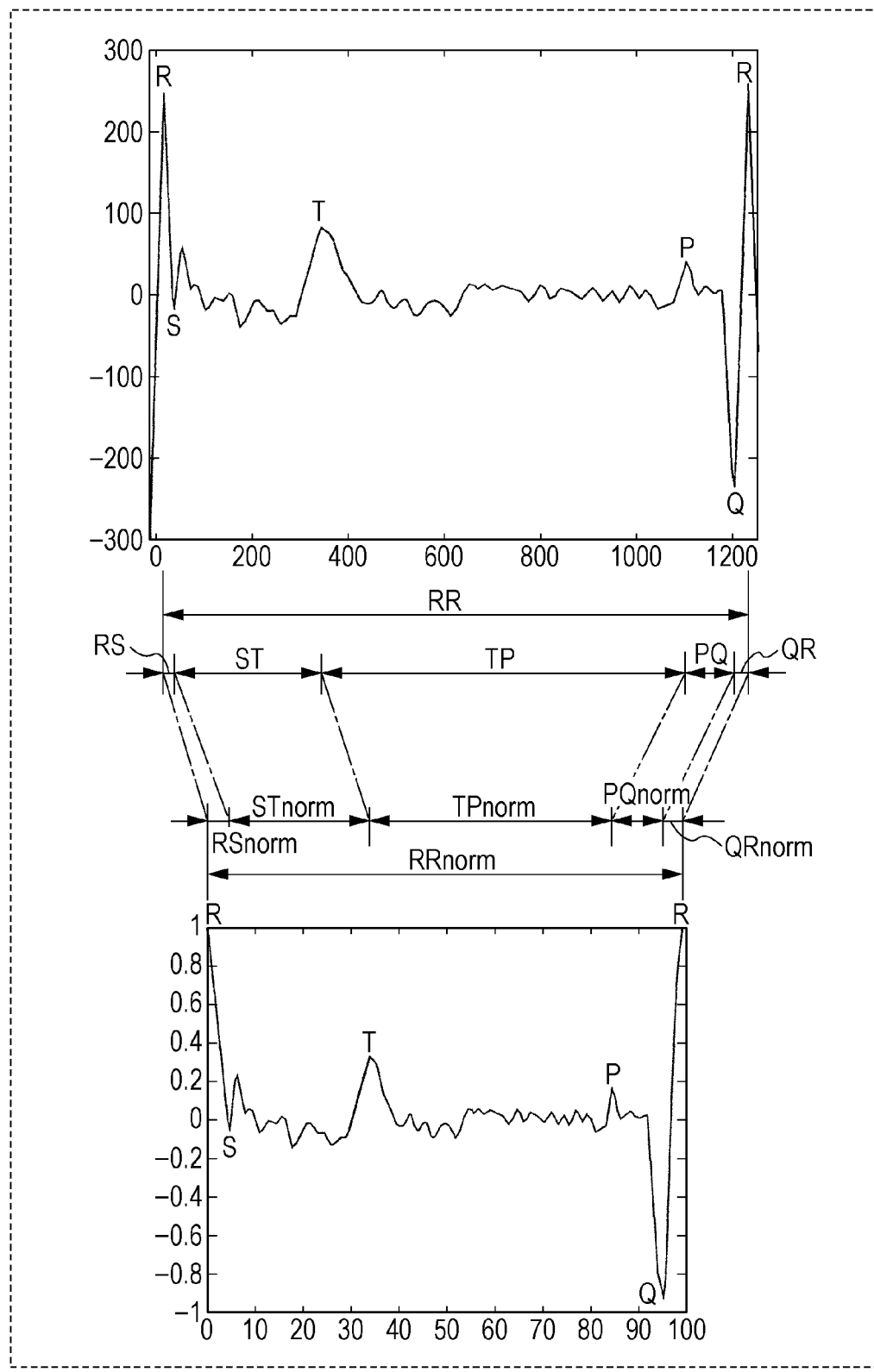
FIG. 19 illustrates another example of normalization according to the first exemplary embodiment.

FIG. 19 illustrates another example of normalization according to the first exemplary embodiment.

The acquiring unit 13 refers to the regulation information illustrated in FIG. 18A and expands or contracts the electrocardiographic waveform in the time axis direction and the amplitude direction. Thus, the acquiring unit 13 obtains the normalized electrocardiographic waveform. More specifically, the acquiring unit 13 obtains the averaged normalized electrocardiographic waveform. At that time, the acquiring unit 13 expands or contracts the time period between the peak of the first R wave and the peak of the second R wave in the electrocardiographic waveform to the first predetermined time period (RRnorm). In addition, the acquiring unit 13 expands or contracts the time period between the peak of the P wave and the peak of the first R wave in the electrocardiographic waveform to the second predetermined time period. Furthermore, the acquiring unit 13 expands or contracts the time period between the peak of the Q wave and the peak of the first R wave in the electrocardiographic waveform to the third predetermined time period. Still furthermore, the acquiring unit 13 expands or contracts the time period between the peak of the S wave and the peak of the first R wave in the electrocardiographic waveform to the fourth predetermined time period. Yet still furthermore, the acquiring unit 13 expands or contracts the time period between the peak of the T wave and the peak of the first R wave in the electrocardiographic waveform to the fifth predetermined time period. That is, the acquiring unit 13 performs normalization so that the position of the peak of each of the P wave, Q wave, S wave, and T wave (the position on the time axis) is aligned at a predetermined position at all times.

More specifically, the acquiring unit 13 separates the R-R duration into an R-S duration, an S-T duration, a T-P duration, a P-Q duration, and a Q-R duration. The R-S duration is a duration between the peak of the first R wave and the peak of the S wave. The S-T duration is a duration between the peak of the S wave and the peak of the T wave. The T-P duration is a duration between the peak of the T wave and the peak of the P wave. The P-Q duration is a duration between the peak of the P wave and the peak of the Q wave. The Q-R duration is a duration between the peak of the Q wave and the peak of the second R wave. Subsequently, the acquiring unit 13 expands or contracts the electrocardiographic waveform in each of the durations in the time axis direction so that each of the durations including the R-R duration is set to a predetermined time period for the duration. The predetermined time period for the R-R duration is RRnorm (the first predetermined time period) and, more specifically, a period of time for 100 samples. The predetermined time periods for the R-S duration, the S-T duration, the T-P duration, the P-Q duration, and the Q-R duration are RSnorm, STnorm, TPnorm, PQnorm, and QRnorm, respectively. RSnorm is the fourth predetermined time period, and STnorm is a time period calculated as (the fifth predetermined time period−the fourth predetermined time period). TPnorm is a time period calculated as (the second predetermined time period−the fifth predetermined time period). PQnorm is a time period calculated as (the third predetermined time period−the second predetermined time period). QRnorm is a time period calculated as (the first predetermined time period−the third predetermined time period). That is, RSnorm, STnorm, TPnorm, PQnorm, QRnorm, and RRnorm are time periods for 5 samples, 30 samples, 50 samples, 10 samples, 5 samples, and 100 samples, respectively.

Through such expansion or contraction in the time axis direction, each of the positions of the P wave, Q wave, S wave, and T wave (the position on the time axis) is aligned at a predetermined position at all times.

Note that to align each of the positions of the P wave, Q wave, S wave, and T wave at a predetermined position at all times, the peaks of all the waves are the peaks to be adjusted. Accordingly, in step S11 illustrated in FIG. 13, the peak of each of the P wave, Q wave, S wave, and T wave is detected. In addition, in step S51 illustrated in FIG. 14, the peak of each of the P wave, Q wave, S wave, and T wave is determined to be the peak to be adjusted. In addition, in step S21 illustrated in FIG. 15, the number PeakNum of the peaks to be adjusted is identified as 4.

Figure 20:
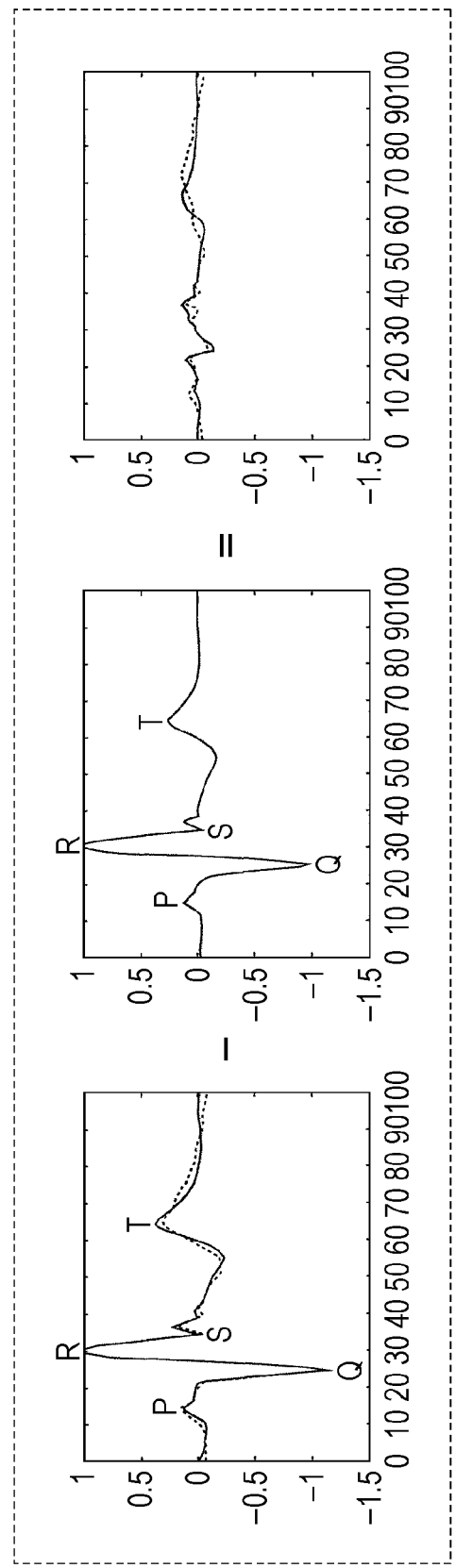
FIG. 20 illustrates another example of the correlation between two waveforms according to the first exemplary embodiment.

FIG. 20 illustrates another example of a correlation between two waveforms according to the first exemplary embodiment.

A graph on the left in FIG. 20 illustrates the normalized electrocardiographic waveform acquired by the acquiring unit 13 in the above-described manner (a solid line) and the registered electrocardiographic waveform of the user (a broken line). For example, the user is the examinee 1 illustrated in FIG. 5. A graph in the middle in FIG. 20 indicates the average of the registered electrocardiographic waveforms for all the users (the overall average). A graph on the right in FIG. 20 indicates the difference obtained by subtracting the overall average from the normalized electrocardiographic waveform (a solid line) and the difference obtained by subtracting the overall average from the registered electrocardiographic waveform (a broken line). The correlation between the differences is 0.66, which is high. Accordingly, since the correlation between the acquired normalized electrocardiographic waveform and the registered electrocardiographic waveform of the examinee 1 is the highest among the correlations between the acquired normalized electrocardiographic waveform and the registered electrocardiographic waveform of the examinees 1 to 6, the identification information regarding the examinee 1 can be correctly output for the acquired normalized electrocardiographic waveform.

Note that according to the present exemplary embodiment, the registered electrocardiographic waveform is the electrocardiographic waveform normalized by expanding or contracting the electrocardiographic waveform of the user in the time axis direction and the amplitude direction. In addition, if there are a plurality of R-R durations in the electrocardiographic waveform of the user measured by the electrocardiograph measuring unit 11 to generate the registered electrocardiographic waveform, the plurality of the normalized electrocardiographic waveforms equal in number to the number of R-R durations are averaged. The electrocardiographic waveform obtained through the averaging operation is the above-described registered electrocardiographic waveform. In addition, the time period between the peak of the first R wave and each of the peaks to be adjusted in the registered electrocardiographic waveform is the same as any one of the above-described second to fifth predetermined time periods. That is, the time period between the peak of the first R wave and the peak of the P wave in the registered electrocardiographic waveform is the same as the second predetermined time period. The time period between the peak of the first R wave and the peak of the Q wave is the same as the third predetermined time period. The time period between the peak of the first R wave and the peak of the S wave is the same as the fourth predetermined time period. The time period between the peak of the first R wave and the peak of the T wave is the same as the fifth predetermined time period.

At that time, as described above, the peak of at least one of the P wave, Q wave, S wave, and T wave may be selected as a peak to be adjusted. Note that the peak of at least one of the P and Q waves needs to be selected.

FIG. 21 illustrates combinations of the peaks aligned through normalization (the peaks to be adjusted) and the accuracy rate of each of the combinations according to the first exemplary embodiment.

As illustrated in FIG. 21, the number of combinations of the peaks to be adjusted is 15. Among the 15 combinations, the accuracy rates of three combinations including only one of the peaks of the S and T waves as the peak to be adjusted or the both are lower than or equal to 72%. In contrast, the accuracy rates of twelve combinations other than the three combinations are higher than 72%. Consequently, according to the present exemplary embodiment, by using, as the peak to be adjusted, the peak of at least one wave including the P wave or Q wave among the P wave, Q wave, S wave, and T wave, a user can be authenticated with high accuracy.

As described above, according to the present exemplary embodiment, the personal authentication apparatus 10 includes the electrocardiograph measuring unit 11, the peak detection unit 12, the acquiring unit 13, and the authentication unit 15. The electrocardiograph measuring unit 11 measures the electrocardiographic waveform of a user using a plurality of electrodes in contact with the user. The peak detection unit 12 detects one of the peak of the P wave and the peak of the Q wave, the peak of the first R wave, and the peak of the second R wave in the measured electrocardiographic waveform. The acquiring unit 13 expands or contracts the measured electrocardiographic waveform in the time axis direction and the amplitude direction on the basis of the peaks of the waves detected by the peak detection unit 12 and obtains the first normalized electrocardiographic waveform. The authentication unit 15 refers to the identification information regarding a plurality of users and the registration information corresponding to the identification information regarding each of the users and including the characteristic information that indicates the characteristics of the electrocardiographic waveform of the user. Thereafter, the authentication unit 15 outputs the identification information of the user corresponding to the characteristic information that indicates the characteristics similar to the first normalized electrocardiographic waveform. At that time, the acquiring unit 13 expands or contracts the measured electrocardiographic waveform between the peak of the first R wave and the peak of the second R wave in the time axis direction to the first predetermined time period (RRnorm). In addition, the acquiring unit 13 expands or contracts the measured electrocardiographic waveform between the peak of the first R wave and the peak of the P wave in the time axis direction to the second predetermined time period (e.g., 0.85×RRnorm) or expands or contracts the measured electrocardiographic waveform between the peak of the first R wave and the peak of the Q wave in the time axis direction to the third predetermined time period (e.g., 0.95×RRnorm). For example, the characteristic information regarding each of the users included in the registration information represents the electrocardiographic waveform.

Thus, in the first normalized electrocardiographic waveform, the time period between the peak of the first R wave and the peak of the P wave is set to the second predetermined time period, or the time period between the peak of the first R wave and the peak of the Q wave is set to the third predetermined time period. Accordingly, authentication for the electrocardiographic waveform of a user can be performed without being influenced by the time period between the peak of the first R wave and the peak of the P wave or the time period between the peak of the first R wave and the peak of the Q wave. As a result, for example, as illustrated in FIG. 21, an accuracy rate of 94% can be obtained for the P wave, or an accuracy rate of 83% can be obtained for the Q wave. Thus, a user (a person) can be authenticated with high accuracy.

In addition, the peak detection unit 12 detects the peak of the P wave and the peak of the Q wave. The acquiring unit 13 expands or contracts the measured electrocardiographic waveform between the peak of the first R wave and the peak of the P wave in the time axis direction to the second predetermined time period (e.g., 0.85×RRnorm). Furthermore, the acquiring unit 13 expands or contracts the measured electrocardiographic waveform between the peak of the first R wave and the peak of the Q wave in the time axis direction to the third predetermined time period (e.g., 0.95×RRnorm).

Accordingly, authentication for the electrocardiographic waveform of a user can be performed without being influenced by the time period between the peak of the first R wave and the peak of the P wave or the time period between the peak of the first R wave and the peak of the Q wave. As a result, for example, as illustrated in FIG. 21, an accuracy rate of 83% can be obtained for the P wave and the Q wave. Thus, a user (a person) can be authenticated with high accuracy.

The peak detection unit 12 further detects the peak of the S wave in the measured electrocardiographic waveform. The acquiring unit 13 further expands or contracts the measured electrocardiographic waveform between the peak of the first R wave and the peak of the S wave in the time axis direction to the fourth predetermined time period (e.g., 0.05×RRnorm).

Accordingly, authentication for the electrocardiographic waveform of a user can be performed without being influenced by the time period between the peak of the first R wave and the peak of the S wave. As a result, for example, as illustrated in FIG. 21, an accuracy rate of 94% can be obtained for the P wave and the S wave, and an accuracy rate of 83% can be obtained for the Q wave and the S wave. Thus, a user (a person) can be authenticated with high accuracy.

In addition, the peak detection unit 12 detects the peak of the T wave in the measured electrocardiographic waveform. The acquiring unit 13 further expands or contracts the measured electrocardiographic waveform between the peak of the first R wave and the peak of the T wave in the time axis direction to the fifth predetermined time period (e.g., 0.35×RRnorm).

Accordingly, authentication for the electrocardiographic waveform of a user can be performed without being influenced by the time period between the peak of the first R wave and the peak of the T wave. As a result, for example, as illustrated in FIG. 21, an accuracy rate of 89% can be obtained for the P wave and the T wave, and an accuracy rate of 83% can be obtained for the Q wave and the T wave. Thus, a user (a person) can be authenticated with high accuracy.

In addition, the peak detection unit 12 further detects the peak of the S wave and the peak of the T wave in the measured electrocardiographic waveform. The acquiring unit 13 expands or contracts the measured electrocardiographic waveform between the peak of the first R wave and the peak of the S wave in the time axis direction to the fourth predetermined time period (e.g., 0.05×RRnorm). In addition, the acquiring unit 13 expands or contracts the measured electrocardiographic waveform between the peak of the first R wave and the peak of the T wave in the time axis direction to the fifth predetermined time period (e.g., 0.35×RRnorm).

Accordingly, authentication for the electrocardiographic waveform of a user can be performed without being influenced by the time period between the peak of the first R wave and the peak of the S wave and the time period between the peak of the first R wave and the peak of the T wave. As a result, for example, as illustrated in FIG. 21, an accuracy rate of 94% can be obtained for the P wave, the S wave, and the T wave, or an accuracy rate of 83% can be obtained for the Q wave, the S wave, and the T wave. Thus, a user (a person) can be authenticated with high accuracy.

Modifications

While the personal authentication apparatus 10 according to the first exemplary embodiment has been described with reference to authentication using the registration information stored in the registration storage unit DB2, a registration process that generates the registration information may be performed.

Configuration of Personal Authentication Apparatus

Figure 22:
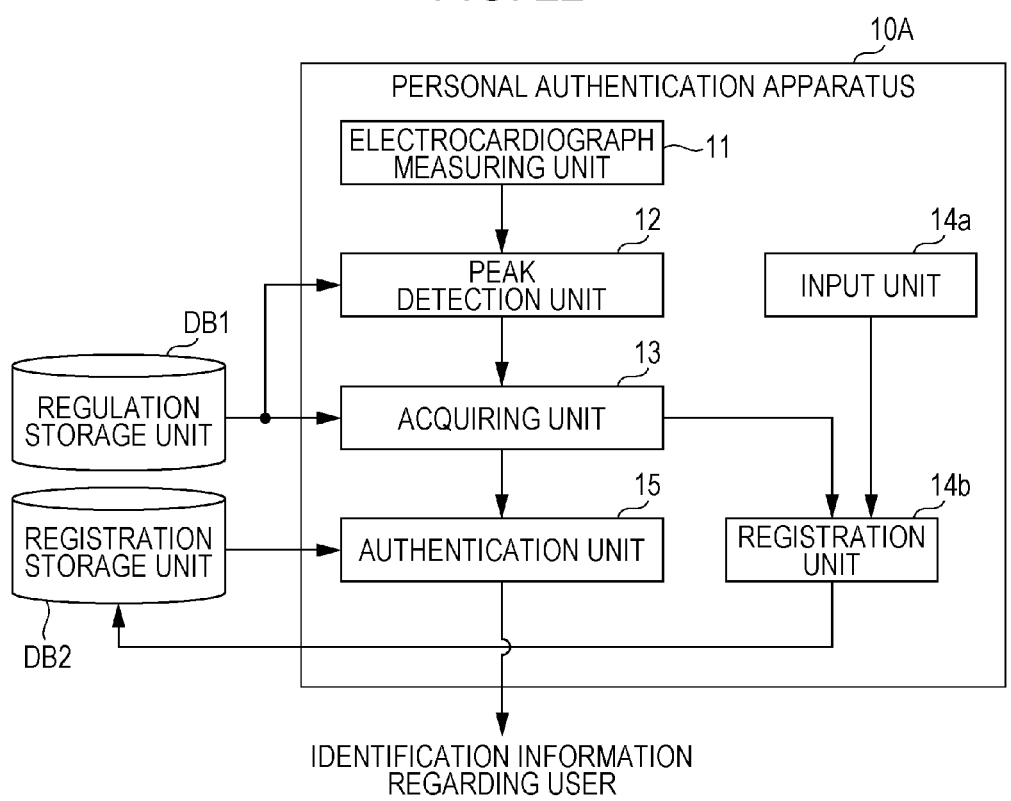
FIG. 22 is a block diagram of the configuration of a personal authentication apparatus according to a modification of the first exemplary embodiment.

FIG. 22 is a block diagram of the configuration of a personal authentication apparatus according to a modification of the first exemplary embodiment.

A personal authentication apparatus 10A includes an electrocardiograph measuring unit 11, a peak detection unit 12, an acquiring unit 13, an input unit 14a, a registration unit 14b, and an authentication unit 15.

Input Unit

The input unit 14a receives the identification information regarding a user through, for example, the operation performed by the user. The input unit 14a is formed from, for example, a keyboard and one of a mouse and a touch panel.

Registration Unit

Each time the registration unit 14b receives the identification information regarding a user by the input unit 14a, the registration unit 14b associates the identification information regarding the user with the normalized electrocardiographic waveform acquired by the acquiring unit 13 for the identification information regarding the user and the number of the R-R durations. In this manner, the registration unit 14b generates the above-described registration information. Thereafter, the registration unit 14b stores the generated registration information in the registration storage unit DB2. Through such processing, the normalized electrocardiographic waveform of the user acquired by the acquiring unit 13 is registered as the registered electrocardiographic waveform. For example, the registration unit 14b registers the normalized electrocardiographic waveform acquired by the acquiring unit 13 as the registered electrocardiographic waveform within a predetermined time period after the identification information of the user is received by the input unit 14a.

Processing Flow in Registration Phase

Figure 23:
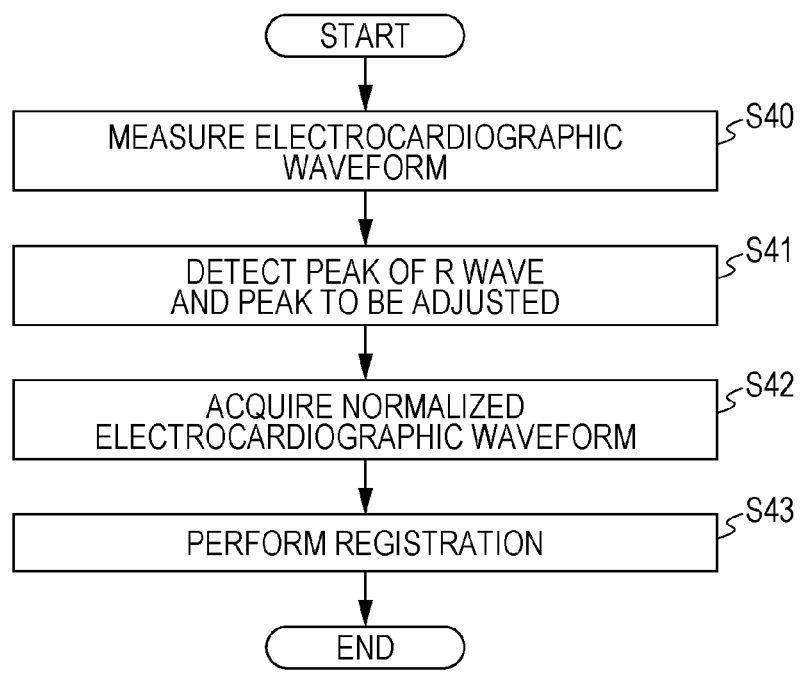
FIG. 23 is a flowchart of the processing operation performed by a personal authentication apparatus in the registration phase according to the modification of the first exemplary embodiment.

FIG. 23 is a flowchart of the processing operation performed by the personal authentication apparatus 10A in the registration phase according to the modification of the first exemplary embodiment.

The personal authentication apparatus 10A performs the processes in steps S40 to S42. The processes performed in steps S40 to S42 are the same as the processes performed by the personal authentication apparatus 10 of the above-described first exemplary embodiment, that is, the processes performed in steps S10 to S12 illustrated in FIG. 13, respectively.

Subsequently, the registration unit 14b associates the normalized electrocardiographic waveform acquired by the acquiring unit 13, the user identification information received by the input unit 14a in advance, and the number of the R-R durations used for generating the normalized electrocardiographic waveform with one another and stores the information in the registration information (step S43). At that time, the normalized electrocardiographic waveform is stored as the registered electrocardiographic waveform. Such a storing process is performed for each of the users to be registered and, thus, the registration information illustrated in FIG. 9 or FIG. 10 is generated. In addition, through the process in step S43, the electrocardiographic waveform of a user to be registered can be registered.

As described above, unlike the personal authentication apparatus 10 according to the first exemplary embodiment, the personal authentication apparatus 10A according to the present modification further includes the input unit 14a and the registration unit 14b. The input unit 14a receives the identification information regarding each of a plurality of users to be registered. The registration unit 14b associates the identification information regarding each of the users to be registered received by the input unit 14a with the characteristic information indicating the characteristics of the first normalized electrocardiographic waveform acquired by the acquiring unit 13 for the user. In this manner, the registration unit 14b generates the registration information.

Thus, the registration information can be generated using the first normalized electrocardiographic waveform acquired by the acquiring unit 13. Accordingly, correct registration information can be easily generated.

In addition, the above-described first exemplary embodiment and the modification of the first exemplary embodiment, the duration between at least one of the peaks to be adjusted and the peak of the first R wave in the first normalized electrocardiographic waveform acquired by the acquiring unit 13 is expanded or contracted to a predetermined time period corresponding to the peak to be adjusted. Note that the peak of at least one of the P wave, Q wave, S wave, and T wave is selected as a peak to be adjusted. At that time, the peak of at least one of the P and Q waves needs to be selected. In such a case, the characteristic information regarding each of the users contained in the registration information indicates the characteristics of the registered normalized electrocardiographic waveform (the registered electrocardiographic waveform) that is acquired by expanding or contracting the electrocardiographic waveform of the user in the time axis direction and the amplitude direction. Furthermore, the duration between the peak of the first R wave and the peak of the second R wave in the registered normalized electrocardiographic waveform is the same as that in the first normalized electrocardiographic waveform, and the time period between each of at least one of the peaks to be adjusted and the peak of the first R wave in the registered normalized electrocardiographic waveform is the same as that in the first normalized electrocardiographic waveform.

Thus, the time period between each of at least one of the peaks to be adjusted and the peak of the first R wave in the registered normalized electrocardiographic waveform is the same as that in the first normalized electrocardiographic waveform. Accordingly, authentication for the electrocardiographic waveform of a user can be performed without being influenced by the point in time (the position on the time axis) at which each of at least one peak to be adjusted appears. As a result, a user (a person) can be authenticated with high accuracy.

While the above-described first exemplary embodiment and modification have been described with reference to use of the signature, the need for the signature may be eliminated. In such a case, the authentication unit 15 directly calculates the correlation or the similarity between the normalized electrocardiographic waveform acquired by the acquiring unit 13 and the registered electrocardiographic waveform of each of the users indicated by the registration information without using a signature. Accordingly, in such a case, since the overall average of the registered electrocardiographic waveforms need not be calculated to generate the signature, the registration information need not contain the number of R-R durations.

FIG. 24 illustrates combinations of the peaks each aligned through normalization (the peaks to be adjusted) and the accuracy rate of each of the combinations when authentication is performed without using the signature according to the first exemplary embodiment and the modification.

As illustrated in FIG. 24, if there is no peak to be adjusted, the accuracy of authentication is 61%. That is, the accuracy rate in this case is an accuracy rate obtained when authentication is performed using an existing method in which any one of the P wave, Q wave, S wave, and T wave is not aligned and without using the signature. In contrast, when there is a peak to be adjusted, the number of combinations of the peaks to be adjusted is 15, as illustrated in FIG. 24. Among the 15 combinations, the accuracy rates of three combinations including only one of the peaks of the S and T waves as the peak to be adjusted or the both are lower than or equal to 72%. In contrast, the accuracy rates of twelve combinations other than the three combinations are higher than 72%. Consequently, according to the above-described first exemplary embodiment and the modification, by using, as the peak to be adjusted, the peak of at least one wave including the P wave or Q wave among the P wave, Q wave, S wave, and T wave, a user can be authenticated with accuracy higher than in the existing method even when a signature is not used. More specifically, a user can be authenticated with an accuracy rate of 83% or higher.

Second Exemplary Embodiment

A personal authentication apparatus according to the present exemplary embodiment is characterized in that instead of an electrocardiographic waveform, a vector obtained through wavelet transform is used as the characteristic information that indicates the characteristics of the electrocardiographic waveform of a user.

Configuration of Personal Authentication Apparatus

Figure 25:
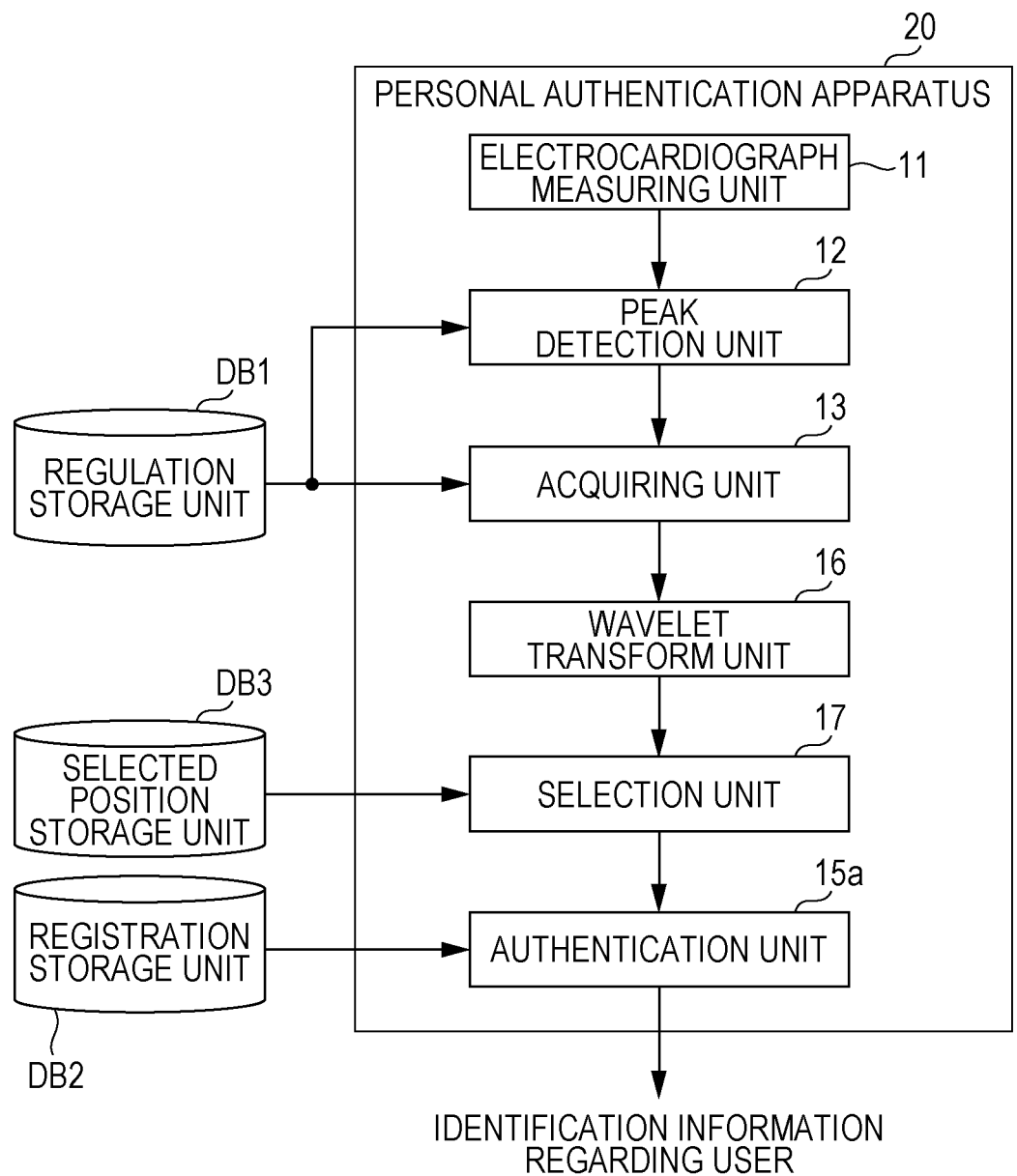
FIG. 25 is a block diagram of the configuration of a personal authentication apparatus according to a second exemplary embodiment.

FIG. 25 is a block diagram of the configuration of the personal authentication apparatus according to the second exemplary embodiment.

According to the present exemplary embodiment, a personal authentication apparatus 20 includes an electrocardiograph measuring unit 11, a peak detection unit 12, an acquiring unit 13, a wavelet transform unit 16, a selection unit 17, and an authentication unit 15a. The electrocardiograph measuring unit 11, the peak detection unit 12, and the acquiring unit 13 are similar to those of the first exemplary embodiment. Accordingly, detailed descriptions of the electrocardiograph measuring unit 11, the peak detection unit 12, and the acquiring unit 13 are not repeated.

Wavelet Transform Unit

The wavelet transform unit 16 applies wavelet transform to a normalized electrocardiographic waveform acquired by the acquiring unit 13 to generate a wavelet matrix. The wavelet matrix represents a plurality of wavelet coefficients arranged in the form of a matrix. In addition, if the size of the wavelet matrix is larger than a predetermined size, the wavelet transform unit 16 scales down the wavelet matrix. In this manner, a matrix having a size smaller than the size of the wavelet matrix is generated. Note that according to the present exemplary embodiment, the need for scale-down of the wavelet matrix performed by the wavelet transform unit 16 may be eliminated.

Selection Unit

The selection unit 17 refers to selected position information stored in a selected position storage unit DB3. Thereafter, the selection unit 17 selects, from the matrix generated by the wavelet transform unit 16, elements located at at least two positions indicated by the selected position information. That is, the selection unit 17 generates a vector having the selected elements (hereinafter referred to as a "characteristic vector"). Note that among the elements of the matrix, the selected position information indicates the position of each of at least two elements to be included in the characteristic vector in the matrix. For example, if the matrix has 8 rows and 10 columns, the selected position information indicates the position of each of the elements to be included in the characteristic vector using row n and column m (1≤n≤8, and 1≤m≤10).

Authentication Unit

The authentication unit 15a refers to the registration information stored in the registration storage unit DB2 and authenticates the user of the characteristic vector generated by the selection unit 17.

Registration Storage Unit

FIG. 26 illustrates an example of registration information according to the second exemplary embodiment.

The registration information stored in the registration storage unit DB2 includes the identification information regarding a plurality of users and the characteristic information indicating the characteristics of the electrocardiographic waveform corresponding to the identification information regarding each of the users. According to the present exemplary embodiment, the characteristic information is the characteristic vector registered for the user (hereinafter referred to as a "registered characteristic vector"). In addition, the registration information includes a plurality of registered characteristic vectors for each of the users. In the example illustrated in FIG. 26, each of the registered characteristic vectors is, for example, a two-dimensional vector that contains two elements. However, the registered characteristic vector may be a three-dimensional vector that contains three elements.

If, as illustrated in FIG. 26, the registered characteristic vector is a two-dimensional vector, the selection unit 17 selects the values of two elements of the wavelet matrix and generates a two-dimensional characteristic vector. In addition, the authentication unit 15a refers to the registration information illustrated in FIG. 26, selects a registered characteristic vector similar to the characteristic vector generated by the selection unit 17, and outputs the identification information regarding a user corresponding to the selected registered characteristic vector.

Note that the registered characteristic vector according to the present exemplary embodiment is a characteristic vector based on the normalized electrocardiographic waveform obtained by expanding or contracting the electrocardiographic waveform of the user in the time axis direction and the amplitude direction (the normalized electrocardiographic waveform of the first exemplary embodiment). That is, the registered characteristic vector is a vector having the elements located at the positions indicated by the above-described selected position information among the elements of the matrix obtained by applying wavelet transform to the normalized electrocardiographic waveform and scaling down the result. In addition, the normalized electrocardiographic waveform is the averaged one. Furthermore, like the first exemplary embodiment, in the normalized electrocardiographic waveform, the time period between the peak to be adjusted detected by the peak detection unit 12 and the peak of the first R wave is the same as the predetermined time period corresponding to the peak to be adjusted.

Figure 27:
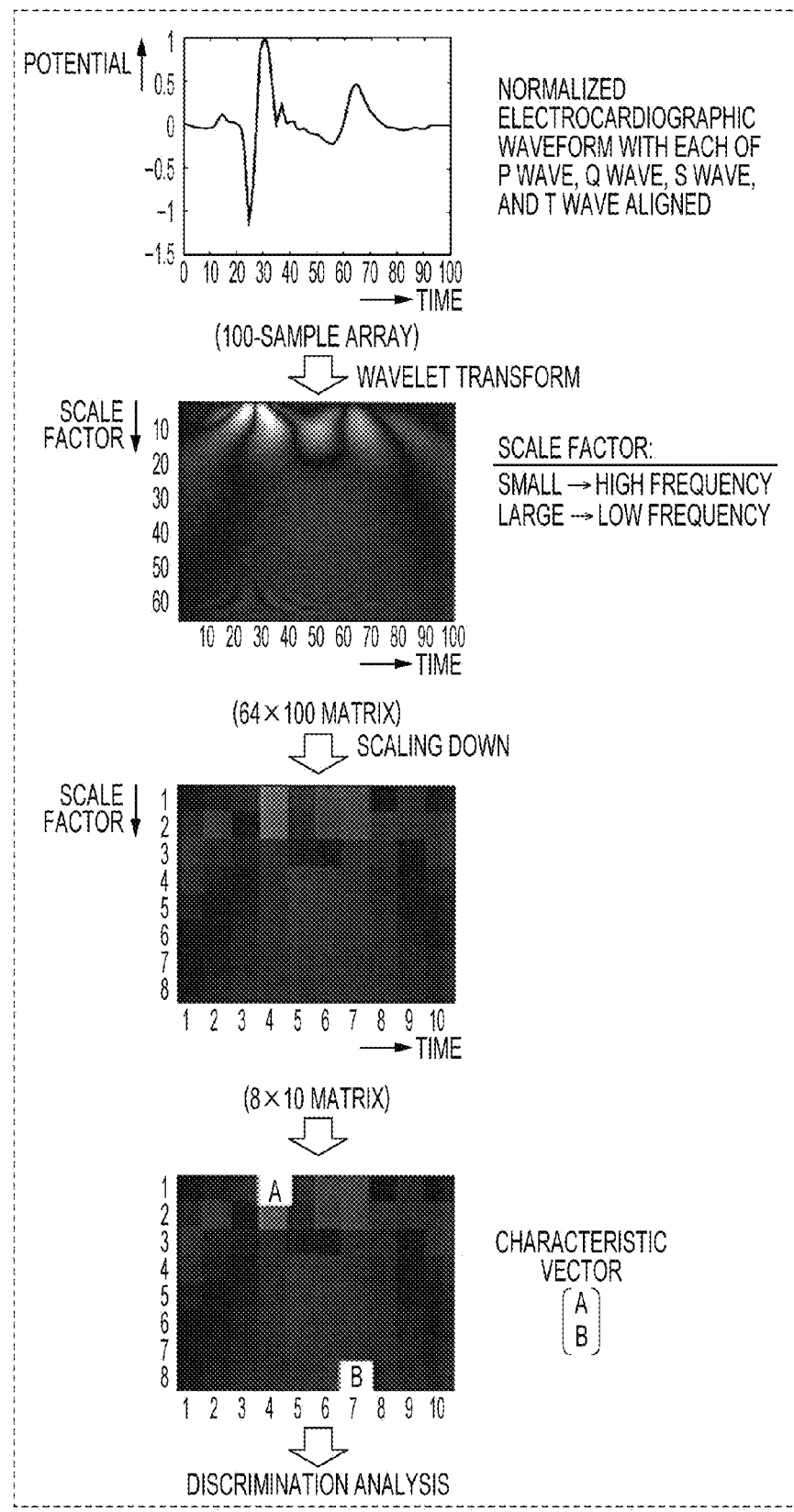
FIG. 27 illustrates an example of the method for generating a characteristic vector according to the second exemplary embodiment.

FIG. 27 illustrates an example of the method for generating the characteristic vector according to the second exemplary embodiment.

The acquiring unit 13 generates the normalized electrocardiographic waveform having the peaks of, for example, the P wave, Q wave, S wave, and T wave each being aligned as the peak to be adjusted. The wavelet transform unit 16 applies the wavelet transform to the normalized electrocardiographic waveform. At that time, for example, the Mexican hat mother wavelet is used as the wavelet transform. The scale factor of the wavelet is 1 to 64, which correspond to 4 Hz to 256 Hz, respectively. Since the electrocardiographic waveform is an array of 100 samples, the result of the wavelet transform is represented as a matrix of 64 lows and 100 columns. This matrix is the wavelet matrix, which includes 64×100 wavelet coefficients as its elements.

To reduce the calculation time, the wavelet transform unit 16 scales down the generated wavelet matrix into a matrix of 8 rows and 10 columns. To scale down the wavelet matrix, the wavelet transform unit 16 separates the matrix of 64 lows and 100 columns into blocks each having 8 rows and 10 columns and averages the wavelet coefficients in each of the blocks.

The selection unit 17 selects, from the matrix of 8 rows and 10 columns, the elements located at two positions indicated by the selected position information to generate a two-dimensional characteristic vector. The authentication unit 15a performs, for example, discrimination analysis using the generated characteristic vector and the registration information to search for a registered characteristic vector that is similar to the characteristic vector. Thereafter, the authentication unit 15a outputs the identification information regarding a user corresponding to the similar registered characteristic vector.

Processing Flow in Authentication Phase

Figure 28:
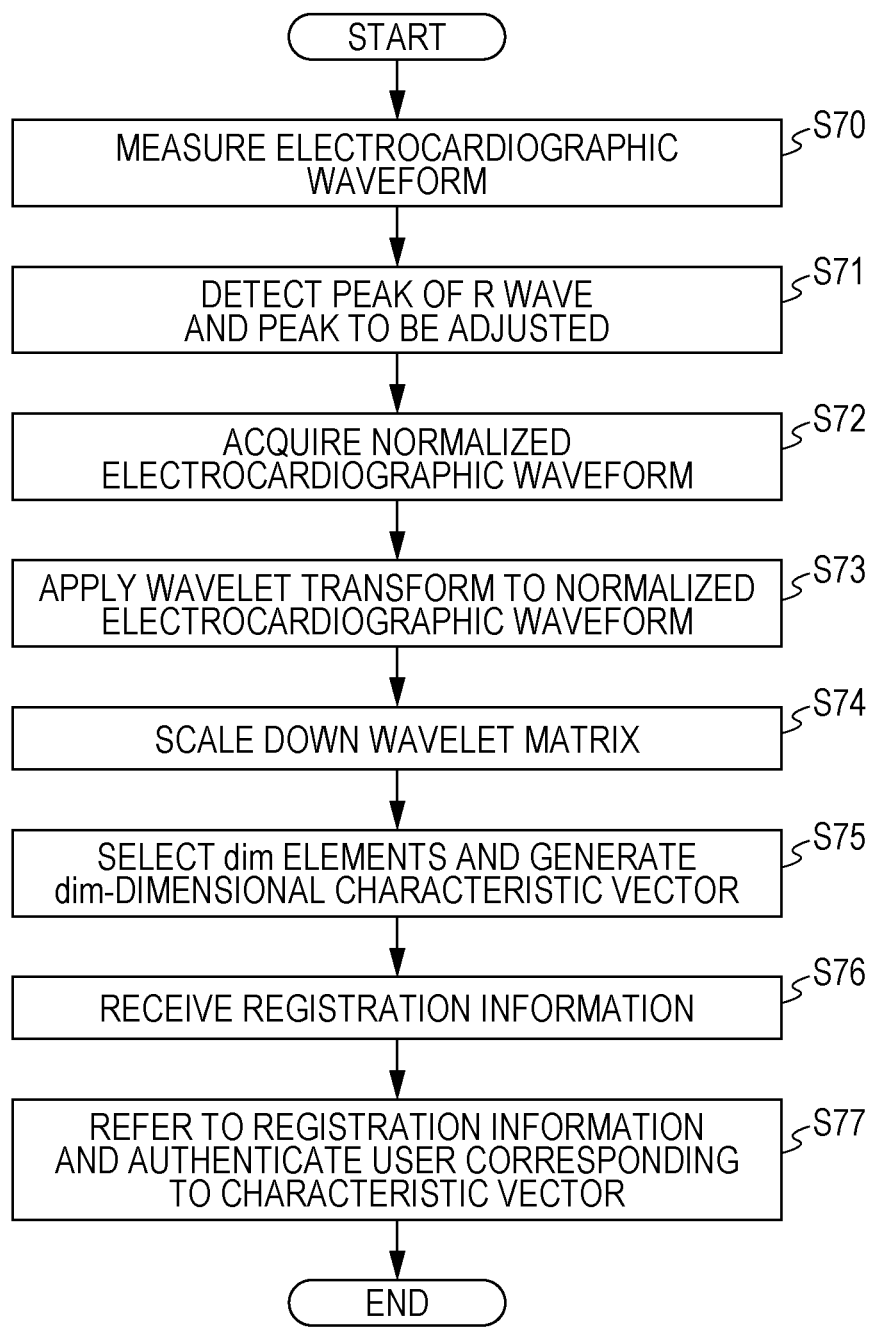
FIG. 28 is a flowchart of the processing operation performed by the personal authentication apparatus in the authentication phase according to the second exemplary embodiment.

FIG. 28 is a flowchart of the processing operation performed by the personal authentication apparatus 20 in the authentication phase according to the second exemplary embodiment.

The electrocardiograph measuring unit 11 measures the electrocardiographic waveform of a user using a plurality of electrodes in contact with the user first (step S70).

The peak detection unit 12 detects, from the electrocardiographic waveform measured in step S70, the peaks of the first R wave and the second R wave in the electrocardiographic waveform. In addition, the peak detection unit 12 detects the peaks of the P wave, Q wave, S wave, and T wave as the peaks to be adjusted (step S71).

The acquiring unit 13 expands or contracts the electrocardiographic waveform in the time axis direction and the amplitude direction on the basis of the detected peaks and acquires the normalized electrocardiographic waveform (step S72). At that time, the acquiring unit 13 expands or contracts the time period between the peak of the first R wave and the peak of the second R wave in the electrocardiographic waveform in the time axis direction to the first predetermined time period (RRnorm). In addition, the acquiring unit 13 expands or contracts the time period between the peak of the first R wave and each of the peaks to be adjusted, which are the peaks of the P wave, Q wave, S wave, and T wave, in the electrocardiographic waveform to the predetermined time period corresponding to the peak. That is, the acquiring unit 13 aligns the peak of each of the P wave, Q wave, S wave, and T wave.

In addition, if the measured electrocardiographic waveform measured in step S70 has a plurality of R-R durations, the acquiring unit 13 acquires the averaged normalized electrocardiographic waveform in step S72. That is, the acquiring unit 13 generates the normalized electrocardiographic waveform for each of the plurality of R-R durations. Thereafter, the acquiring unit 13 calculates the average of the normalized electrocardiographic waveforms equal in number to the number of the R-R durations to obtain the averaged normalized electrocardiographic waveform.

The wavelet transform unit 16 applies the wavelet transform to the normalized electrocardiographic waveform acquired in step S72 and generates a wavelet matrix (step S73). Subsequently, if the size of the wavelet matrix generated in step S73 is larger than a predetermined size, the wavelet transform unit 16 scales down the wavelet matrix (step S74).

The selection unit 17 selects, from the matrix obtained through the scale-down in step S74, dim elements located at the positions indicated by the selected position information and generates a dim-dimensional characteristic vector (step S75). Note that "dim" represents an integer greater than or equal to 2.

The authentication unit 15a acquires the registration information stored in the registration storage unit DB2 (step S76). Thereafter, the authentication unit 15a refers to the acquired registration information (e.g., the registration information illustrated in FIG. 26) and authenticates the user corresponding to the characteristic vector generated by the selection unit 17 (step S77). That is, the authentication unit 15a performs the discrimination analysis using the generated characteristic vector and a plurality of the registered characteristic vectors each corresponding to the identification information regarding one of the plurality of users. As a result, the authentication unit 15a outputs the identification information regarding the user corresponding to the generated characteristic vector.

FIG. 29 illustrates combinations of the peaks to be adjusted for each of the numbers of selected elements and the highest accuracy rate of each of the combinations according to the second exemplary embodiment. Note that the number of selected elements is the number of elements selected by the selection unit 17 (the above-described "dim"). Hereinafter, the number is referred to as the "number of selected elements".

According to the present exemplary embodiment, as illustrated in FIG. 29, the highest accuracy rate 100% can be obtained even when the number of selected elements is 2 or 3 and even when normalization is performed using any one of the 12 combinations of the peaks to be adjusted. Note that dim elements are selected form the matrix, and the accuracy rate varies in accordance with a combination of the selected dim elements. The highest accuracy rate illustrated in FIG. 29 is the highest accuracy rate among the accuracy rates of a plurality of combinations of dim elements. The number of combinations of two elements is 3160, and the number of combinations of three elements is 82160. That is, the highest accuracy rate illustrated in FIG. 29 is the highest value among the accuracy rates obtained for these combinations. In addition, the accuracy rate is based on the electrocardiographic waveforms measured 12 times for each of the above-described 6 examinees.

As used herein, a combination of dim elements is referred to as an "element combination", and a combination of the peaks to be adjusted is referred to as a "peak-to-be-adjusted combination".

FIG. 30 illustrates the peak-to-be-adjusted combinations for each of the numbers of selected elements and the number of element combinations each having an accuracy rate of 100% for the peak-to-be-adjusted combination according to the second exemplary embodiment.

According to the present exemplary embodiment, as illustrated in FIG. 30, when the number of selected elements is 2 and the peak-to-be-adjusted combination includes only the peak of the P wave, the number of the element combinations each having an accuracy rate of 100% is 3.

Each of the two elements included in the three element combinations is, for example, any one of the 8×10 elements included in the matrix having 8 rows and 10 columns. As illustrated in FIG. 30, the number of element combinations having an accuracy rate of 100% generally increases with increasing number of the peaks to be adjusted included in the peak-to-be-adjusted combination. That is, as the number of the peaks to be adjusted increases, authentication can be performed more easily.

Figure 31:
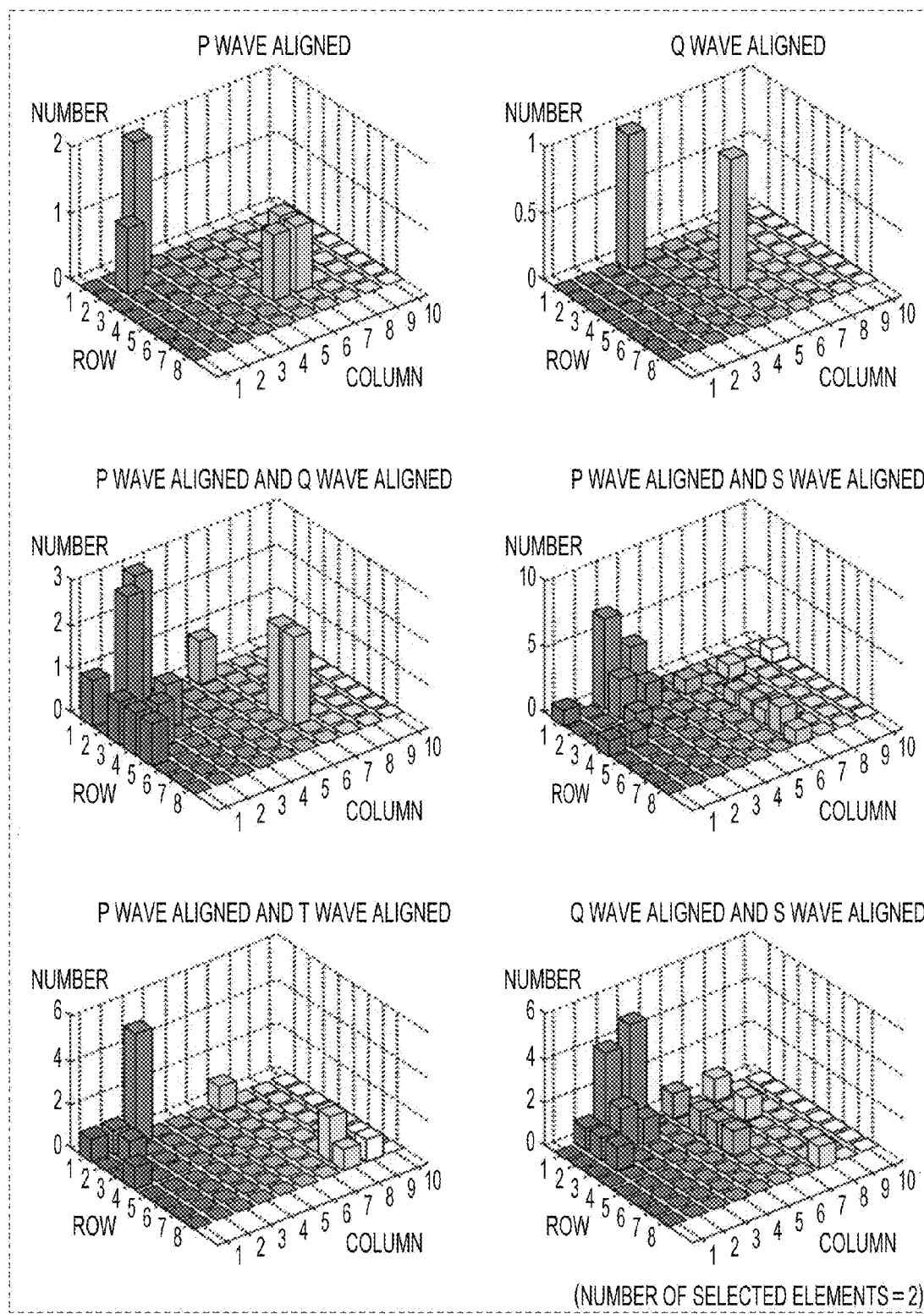
FIG. 31 illustrates the positions of two elements included in each of the element combinations having an accuracy rate of 100% in a matrix when the number of selected elements is 2 according to the second exemplary embodiment.
Figure 32:
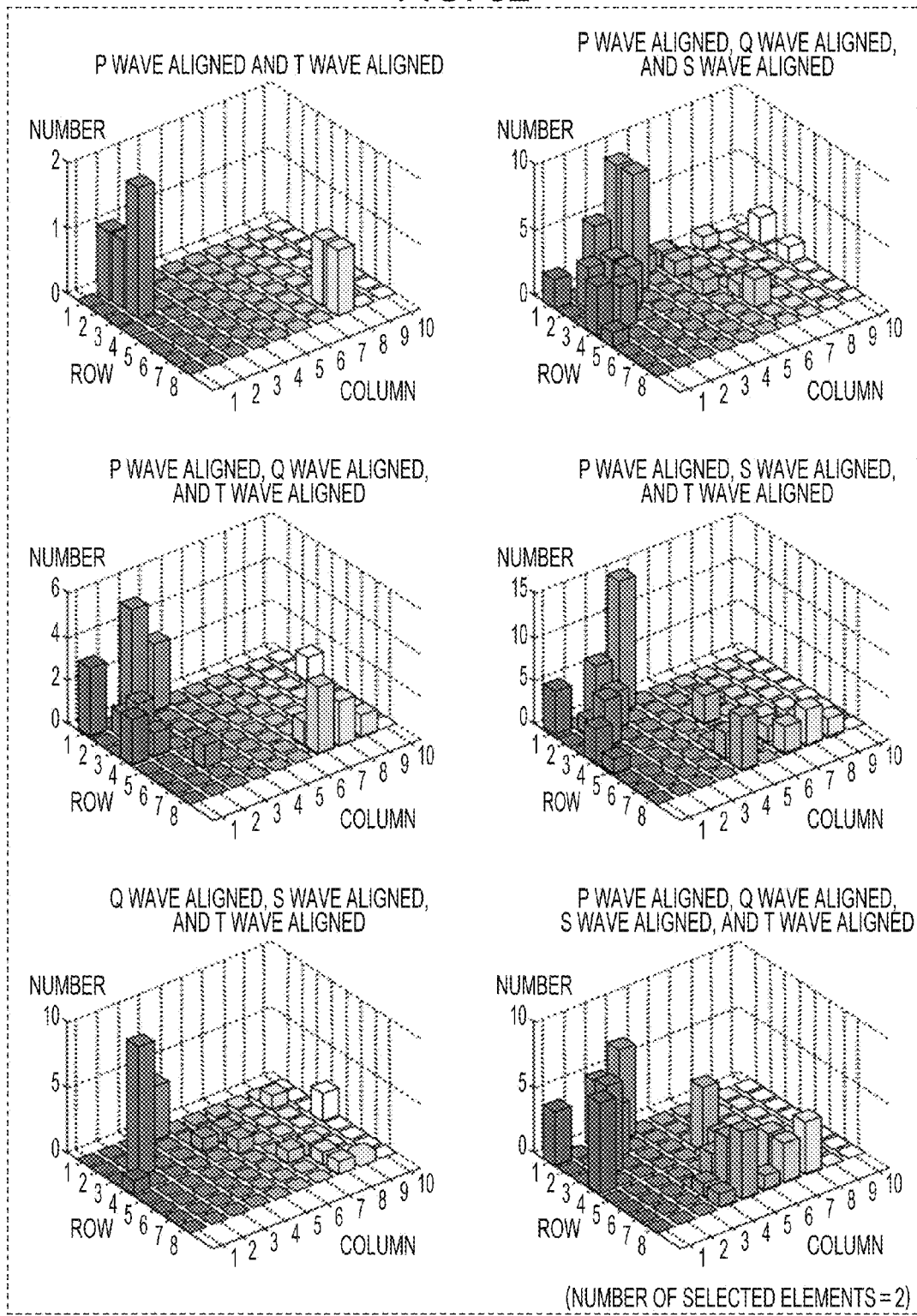
FIG. 32 illustrates the positions of two elements included in each of the element combinations having an accuracy rate of 100% in the matrix when the number of selected elements is 2 according to the second exemplary embodiment.

FIGS. 31 and 32 illustrate the positions of two elements included in each of the element combinations having an accuracy rate of 100% in the matrix when the number of selected elements is 2 according to the second exemplary embodiment. Note that in FIGS. 31 and 32, the axis of each of the three-dimensional graphs in the horizontal direction represents the column number of the matrix, and the axis in the depth direction represents the row number of the matrix. Furthermore, the ordinate of the three-dimensional graph represents the number of the element combinations each including the elements indicated by the row number and the column number of the matrix and having an accuracy rate of 100%.

As illustrated in FIG. 30, when the number of selected elements is 2 and if the peak-to-be-adjusted combination includes only the peak of the P wave (i.e., the peaks of the P wave are aligned), the number of the element combinations each having an accuracy rate of 100% is 3. In such a case, as indicated by the upper left graph in FIG. 31, the number of the element combinations each including the element located at the position (1, 3) of the matrix and having an accuracy rate of 100% is 2, and the number of the element combinations each including the element located at the position (2, 2) of the matrix and having an accuracy rate of 100% is 1. Similarly, the number of the element combinations each including the element located at the position (6, 6) of the matrix and having an accuracy rate of 100% is 1, and the number of the element combinations each including the element located at the position (5, 7) of the matrix and having an accuracy rate of 100% is 1. The number of the element combinations each including the element located at the position (6, 7) of the matrix and having an accuracy rate of 100% is 1. Note that the position (n, m) represents the position of the entry in the n-th row and the m-th column of the matrix.

According to the present exemplary embodiment, in each of the graphs in FIGS. 31 and 32, when the number of selected elements is 2, that is, the characteristic vector is a two-dimensional vector, the selected position information indicates the positions of two elements in the matrix, where the two elements are selected in descending order of the value on the ordinate. Accordingly, when the peak-to-be-adjusted combination includes only the peak of the P wave (when the peaks of only the P wave are aligned), the selected position information indicates the position (1, 3) and one of the position (2, 2), the position (6, 6), the position (5, 7), and the position (6, 7), as illustrated in the upper left graph in FIG. 31.

Figure 33:
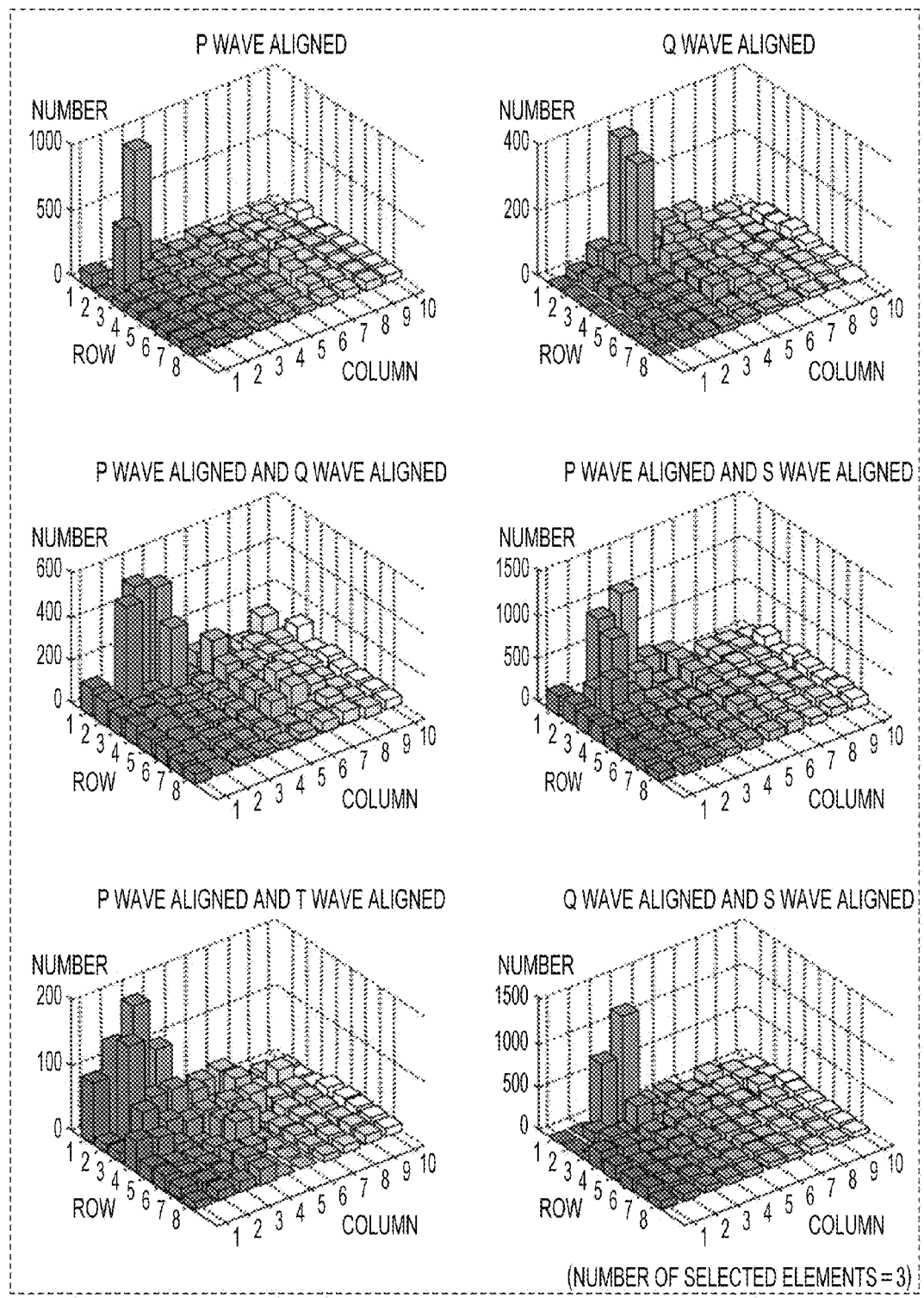
FIG. 33 illustrates the positions of three elements included in each of the element combinations having an accuracy rate of 100% in the matrix when the number of selected elements is 3.
Figure 34:
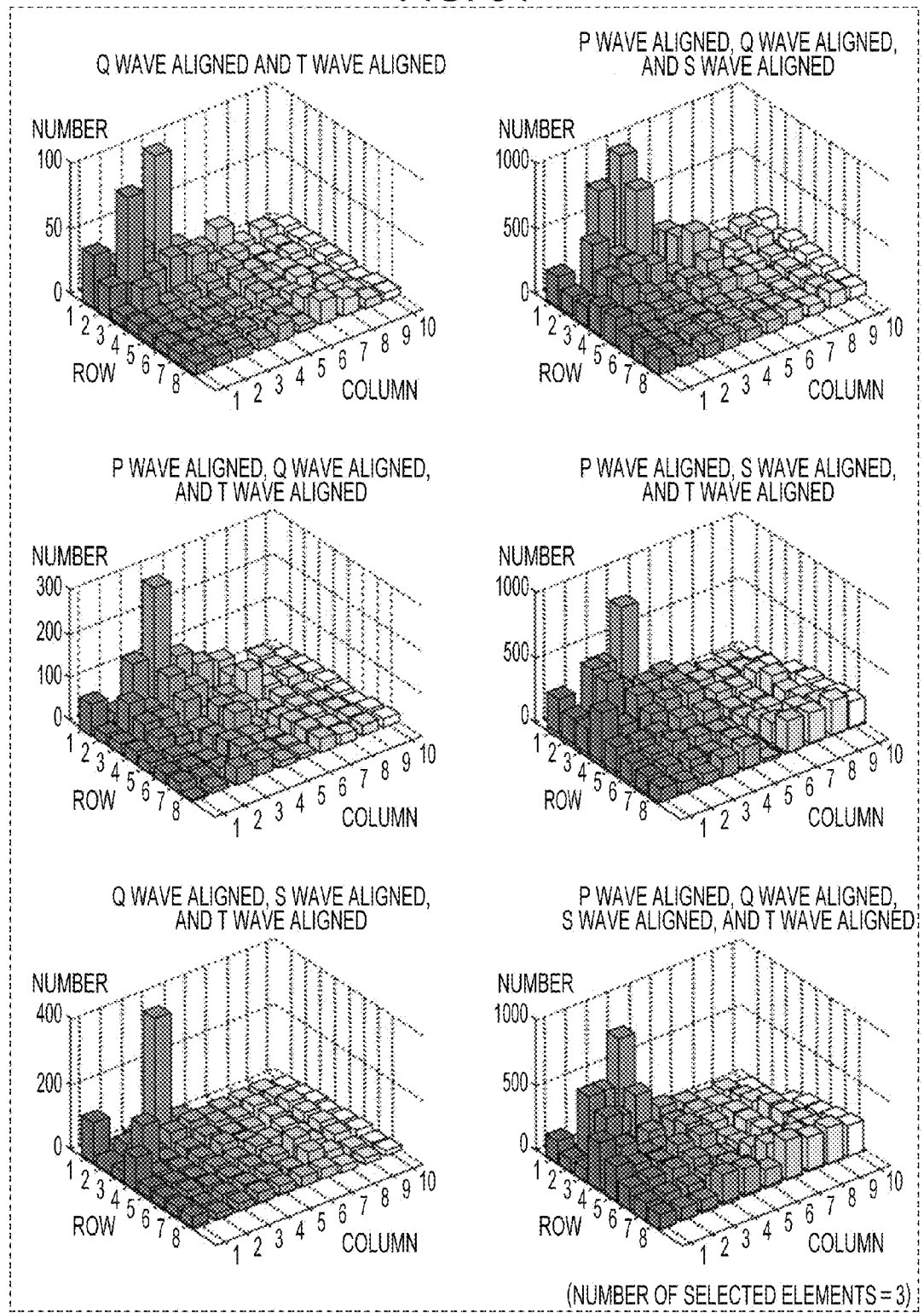
FIG. 34 illustrates the positions of three elements included in each of the element combinations having an accuracy rate of 100% in the matrix when the number of selected elements is 3.

FIGS. 33 and 34 illustrate the positions of three elements included in each of the element combinations having an accuracy rate of 100% in the matrix when the number of selected elements is 3.

As illustrated in FIG. 30, when the number of selected elements is 3 and if the peak-to-be-adjusted combination includes only the peak of the P wave (the peaks of only the P wave are aligned), the number of the element combinations each having an accuracy rate of 100% is 1706. In such a case, as illustrated in the upper left graph in FIG. 33, most of the element combinations includes the element located at the position (1, 3).

According to the present exemplary embodiment, as in the case where the number of selected elements is 2, when the number of selected elements is 3, the selected position information indicates the positions of three elements in the matrix, where the three elements are selected in the descending order of the value on the ordinate of the graph in FIGS. 33 and 34. Note that when the number of selected elements is 3, the characteristic vector is a three-dimensional vector. Accordingly, if the peak-to-be-adjusted combination includes the peaks of only the P wave and S wave (the peaks of the P wave are aligned, and the peaks of the S wave are aligned), the selected position information indicates the position (1, 4), the position (1, 3), and the position (2, 3), as illustrated in a graph on the right and second from the top in FIG. 33.

According to the present exemplary embodiment, since the selected position information indicates the position of each of the elements contained in the element combinations each having an accuracy rate of 100% in this manner, a user can be authenticated with high accuracy.

As described above, unlike the personal authentication apparatus 10 of the first exemplary embodiment, the personal authentication apparatus 20 according to the present exemplary embodiment further includes the wavelet transform unit 16 and the selection unit 17. The wavelet transform unit 16 applies the wavelet transform to the first normalized electrocardiographic waveform acquired by the acquiring unit 13 to generate a first matrix. The selection unit 17 selects, from the generated first matrix, at least two elements and generates a characteristic vector containing the at least two selected elements. In addition, the authentication unit 15a refers to the registration information including a vector serving as the characteristic information of each of the users and searches for the identification information regarding a user associated with a vector similar to the generated characteristic vector. Thereafter, the authentication unit 15a outputs the found identification information of the user.

In this manner, since the characteristic information included in the registration information is a vector, the amount of data of the registration information can be reduced more than the amount of data in the form of an electrocardiographic waveform used in the first exemplary embodiment. Accordingly, the capacity of the registration storage unit DB2, which is a memory that stores the registration information, can be reduced. In addition an accuracy rate of 100% can be obtained for the electrocardiographic waveform measured for, for example, 20 seconds or longer.

Modifications

According to the above-described second exemplary embodiment, the personal authentication apparatus 20 performs authentication using the registration information stored in the registration storage unit DB2. However, a registration process that generates the registration information may be performed.

Configuration of Personal Authentication Apparatus

Figure 35:
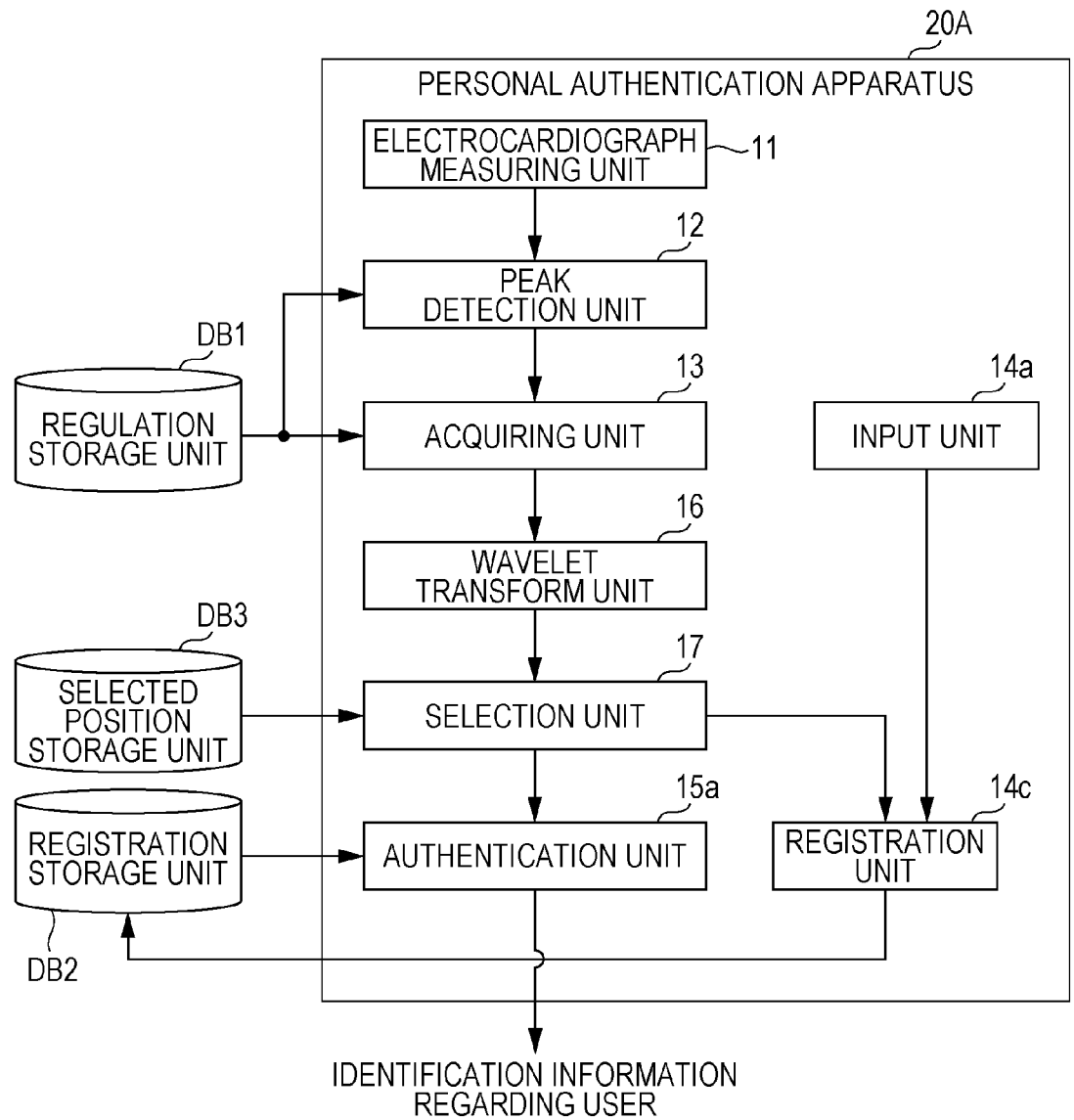
FIG. 35 is a block diagram of the configuration of a personal authentication apparatus according to a modification of the second exemplary embodiment.
Figure 44:
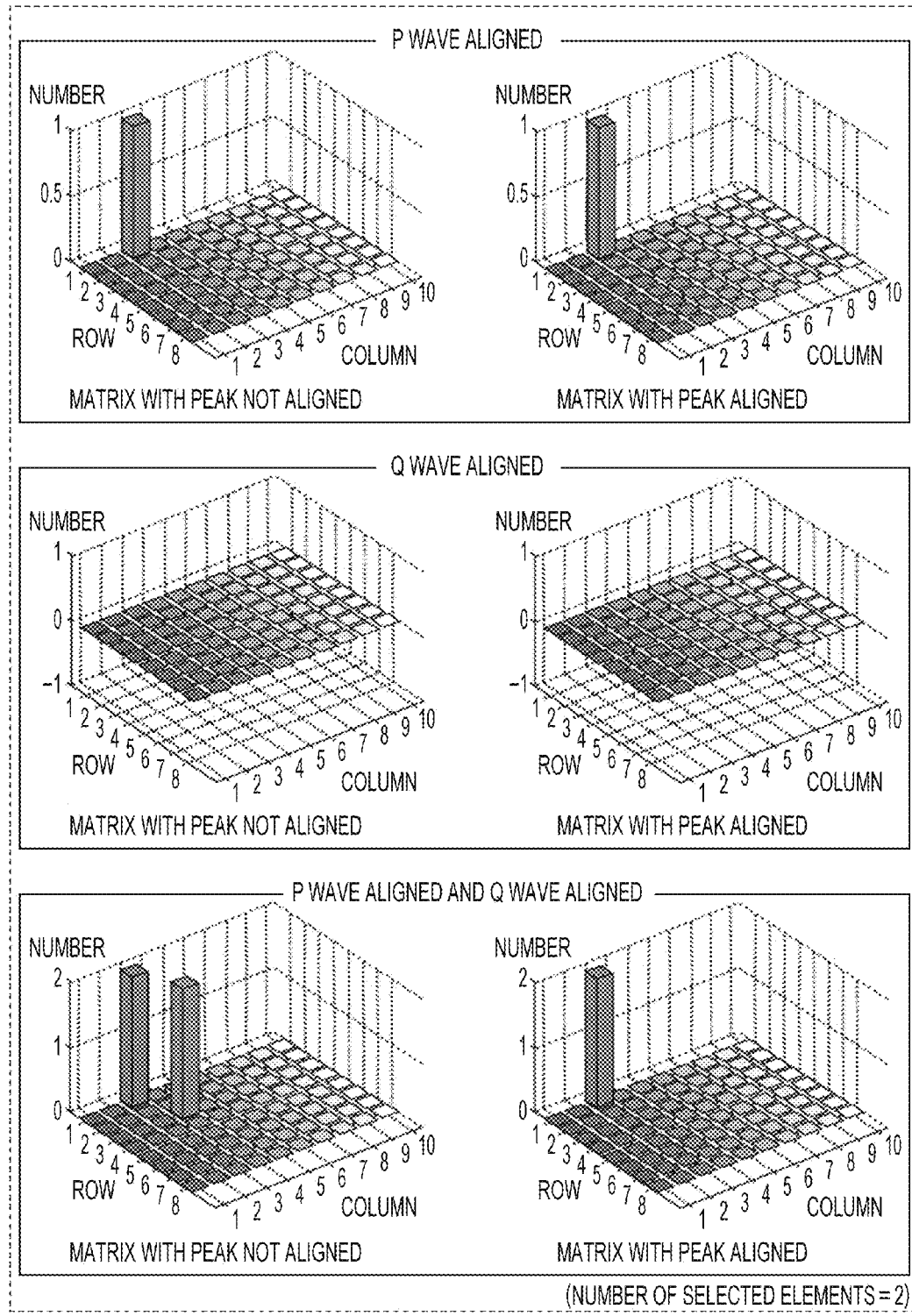
FIG. 44 illustrates the positions of two elements included in each of the element combinations having an accuracy rate of 100% in the matrix when the number of selected elements is 2 according to the third exemplary embodiment.
Figure 45:
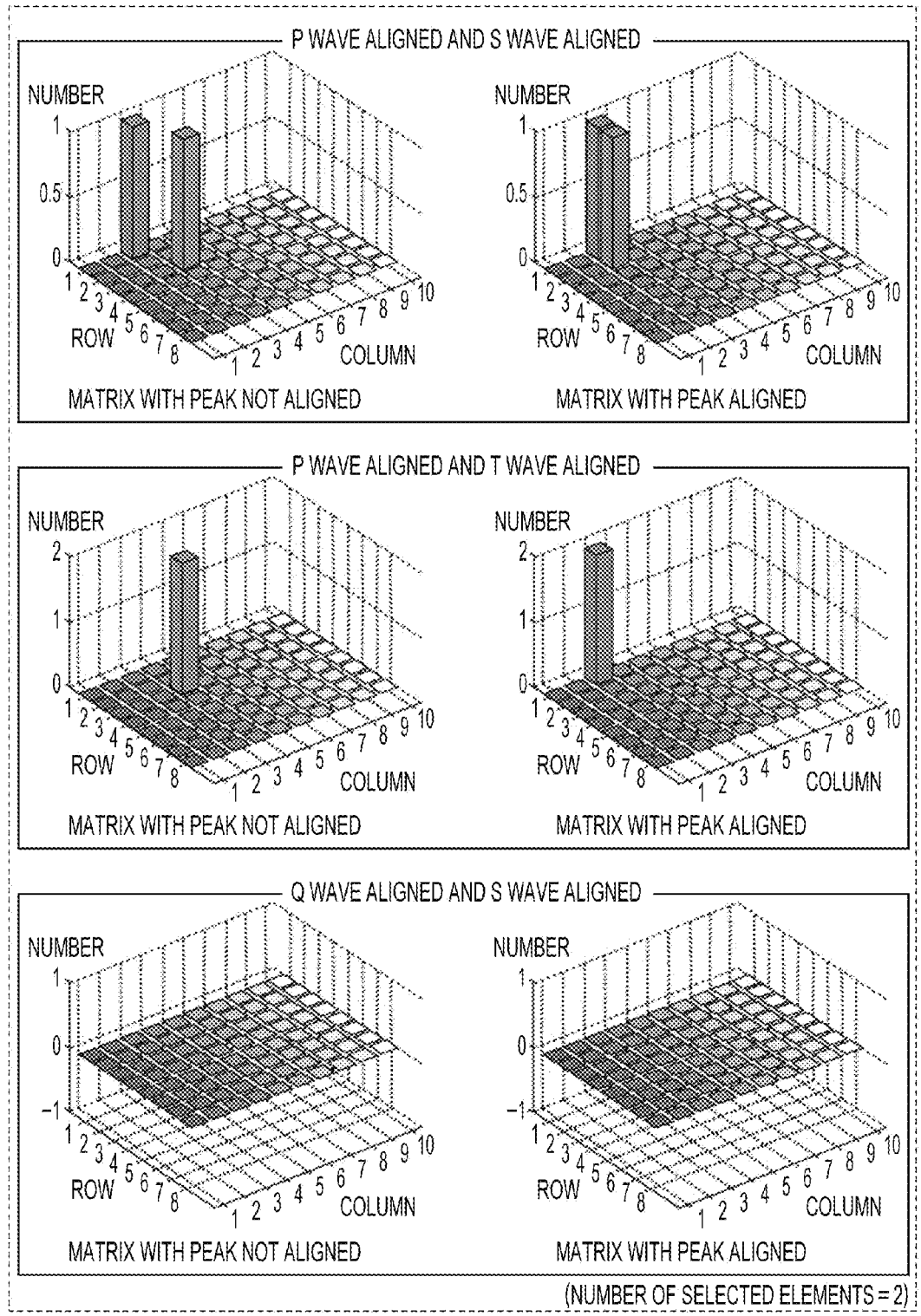
FIG. 45 illustrates the positions of two elements included in each of the element combinations having an accuracy rate of 100% in the matrix when the number of selected elements is 2 according to the third exemplary embodiment.
Figure 46:
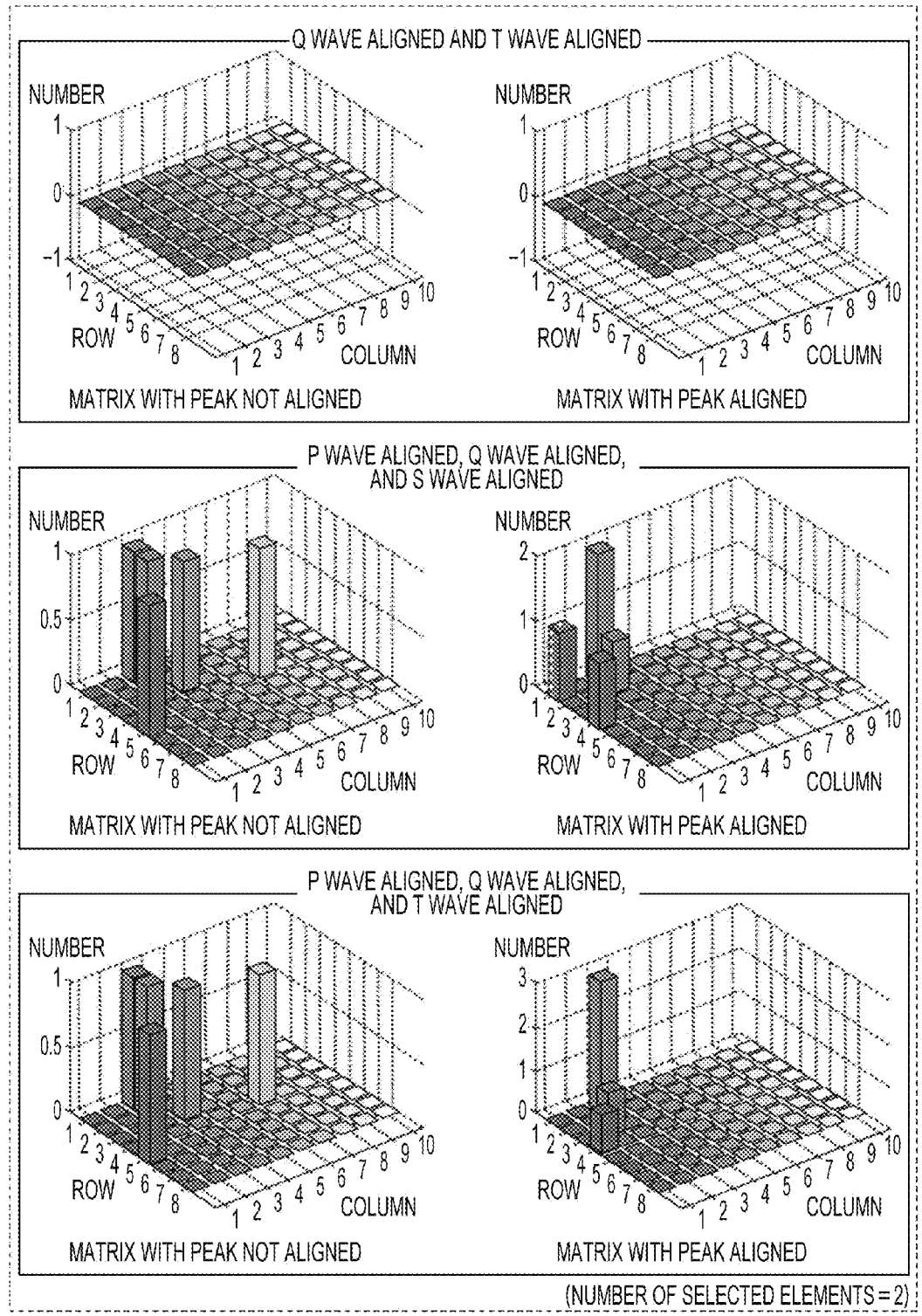
FIG. 46 illustrates the positions of two elements included in each of the element combinations having an accuracy rate of 100% in the matrix when the number of selected elements is 2 according to the third exemplary embodiment.
Figure 47:
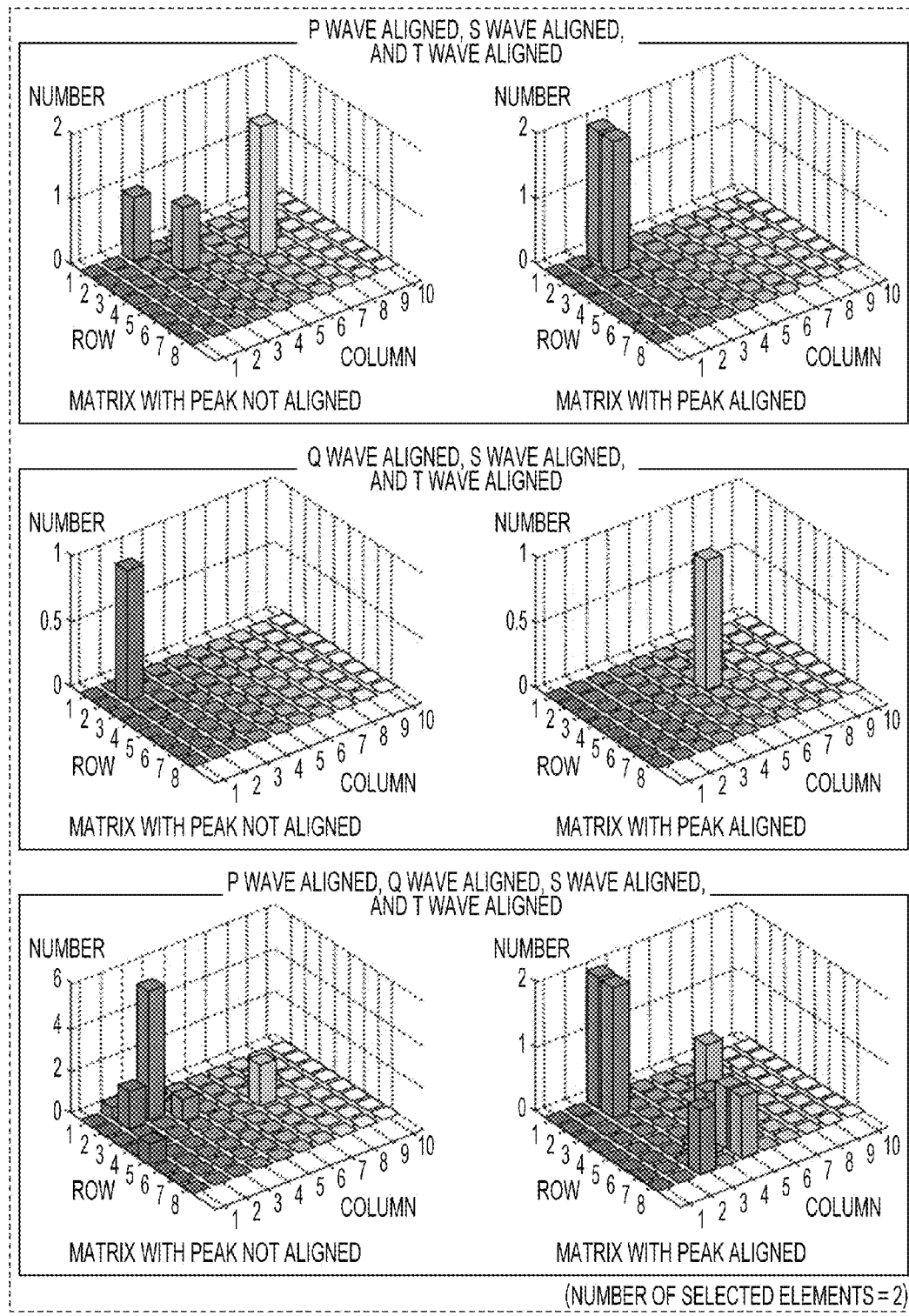
FIG. 47 illustrates the positions of two elements included in each of the element combinations having an accuracy rate of 100% in the matrix when the number of selected elements is 2 according to the third exemplary embodiment.
Figure 48:
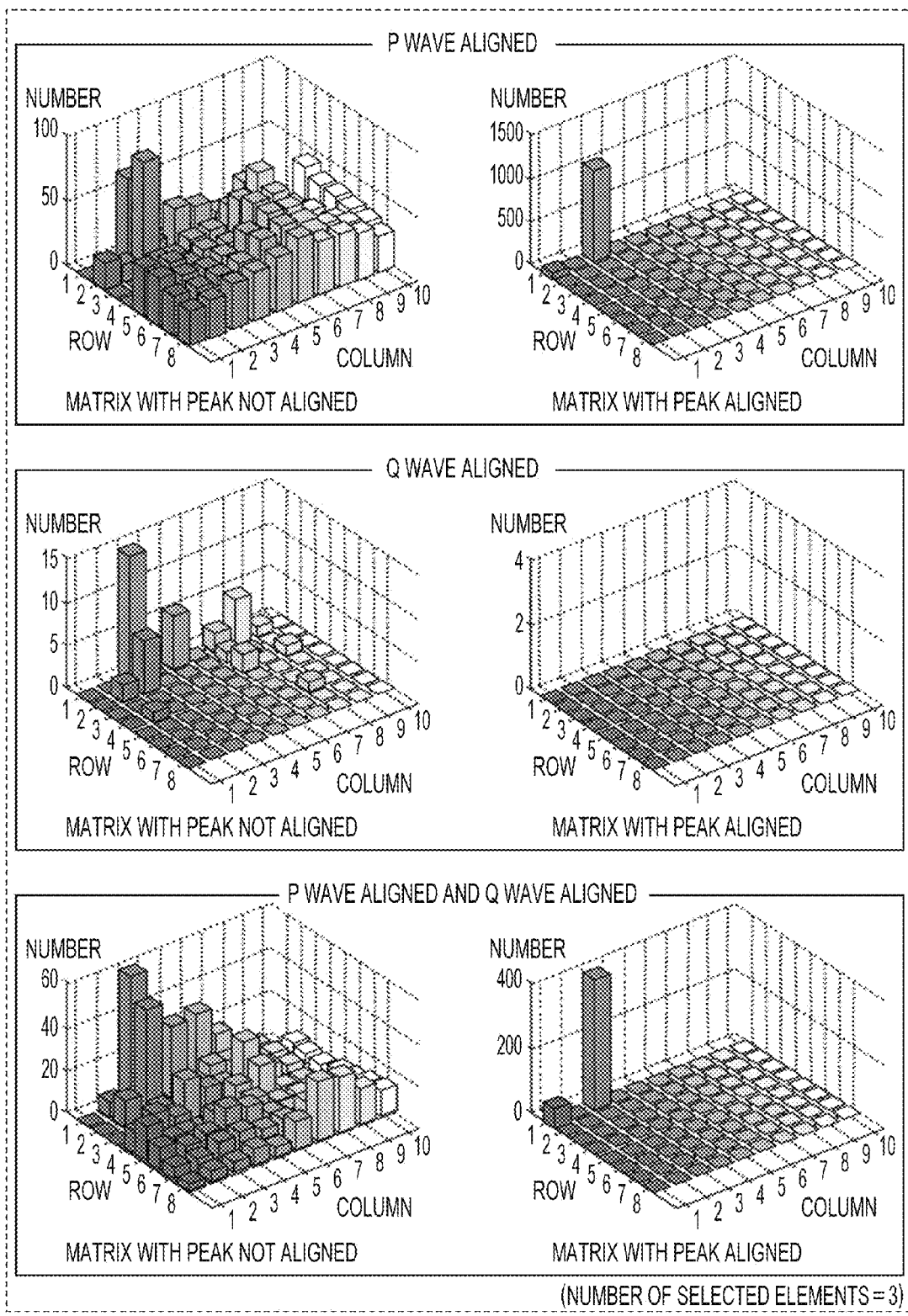
FIG. 48 illustrates the positions of three elements included in each of the element combinations having an accuracy rate of 100% in the matrix when the number of selected elements is 3 according to the third exemplary embodiment.
Figure 49:
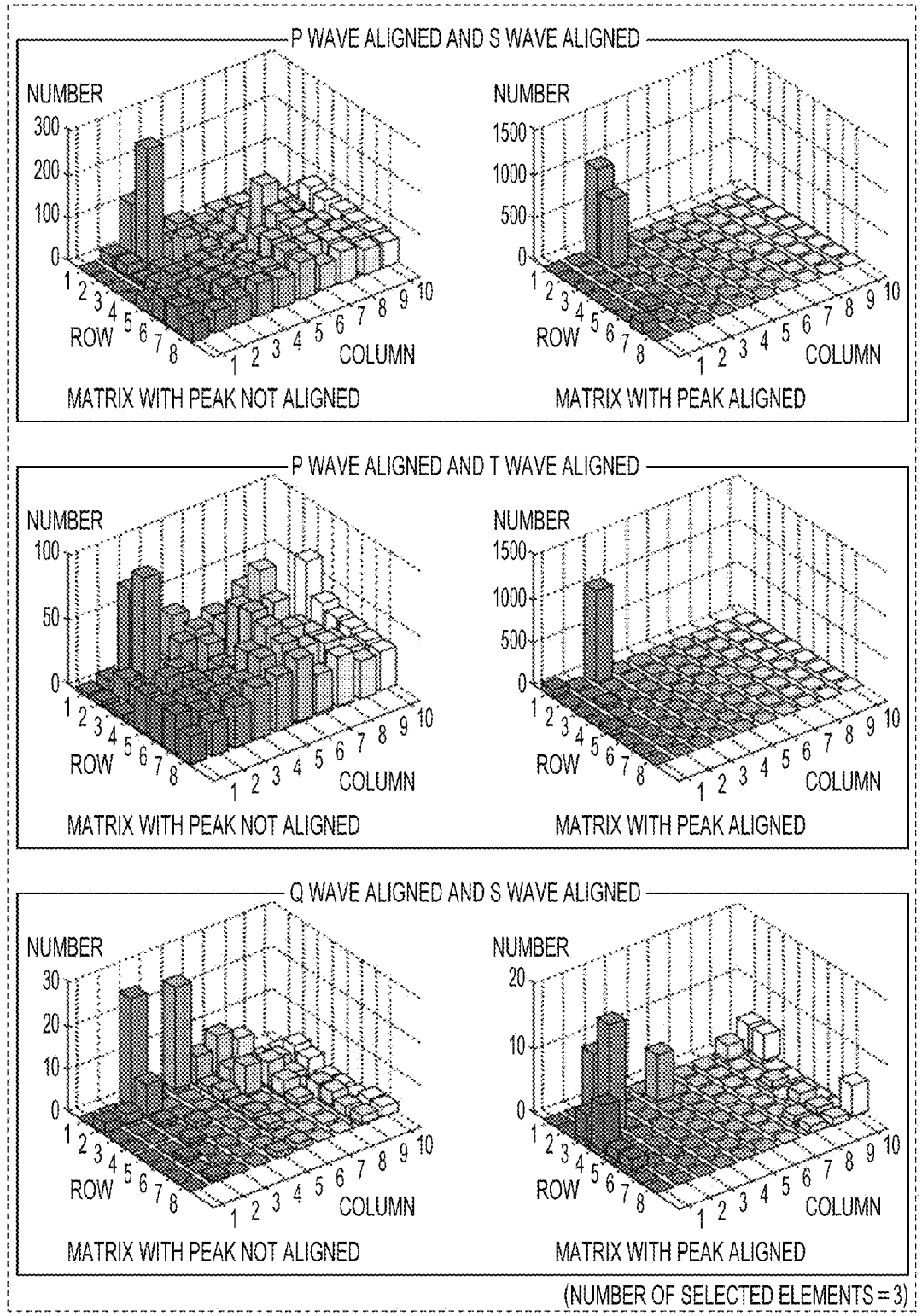
FIG. 49 illustrates the positions of three elements included in each of the element combinations having an accuracy rate of 100% in the matrix when the number of selected elements is 3 according to the third exemplary embodiment.
Figure 50:
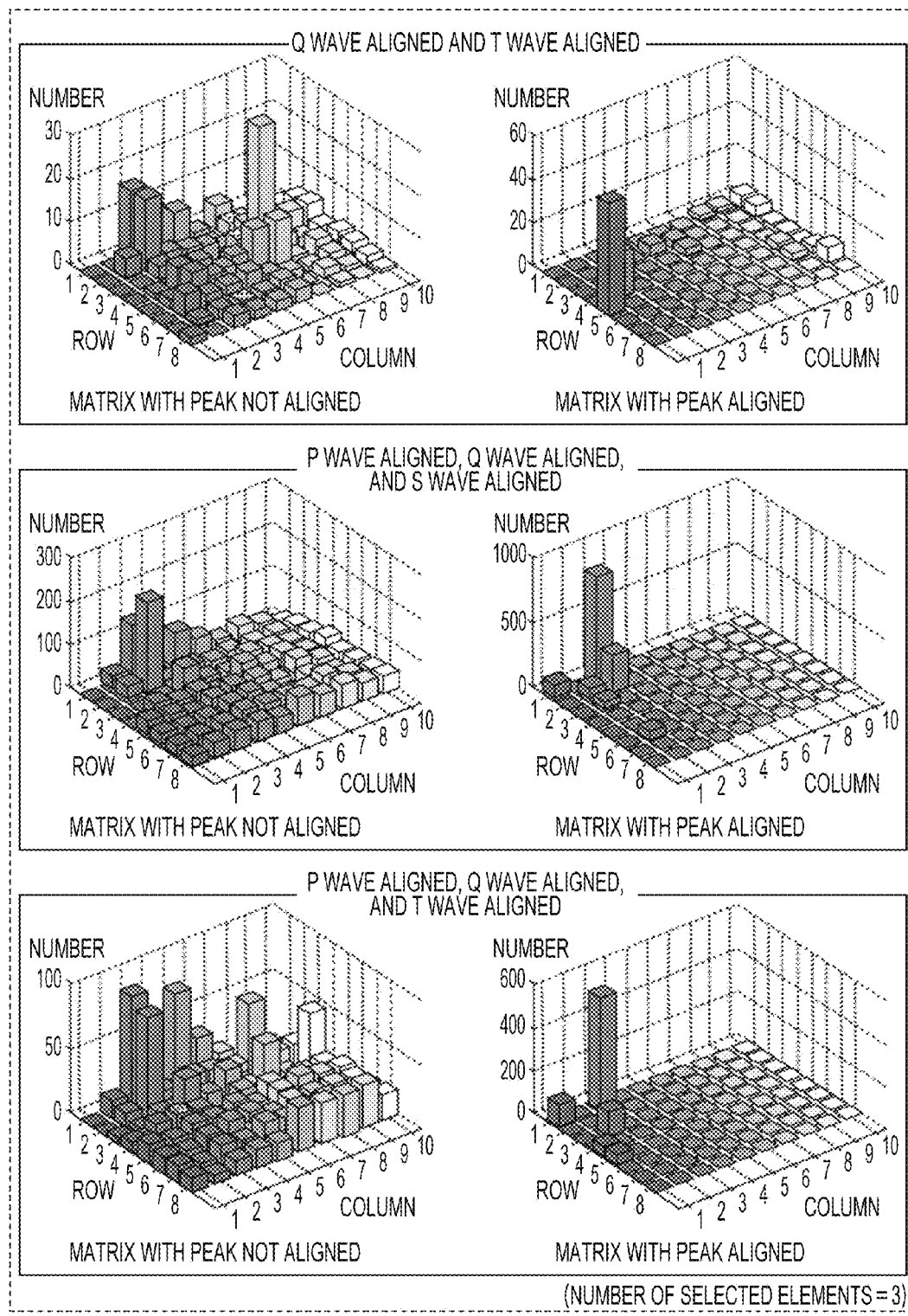
FIG. 50 illustrates the positions of three elements included in each of the element combinations having an accuracy rate of 100% in the matrix when the number of selected elements is 3 according to the third exemplary embodiment.
Figure 51:
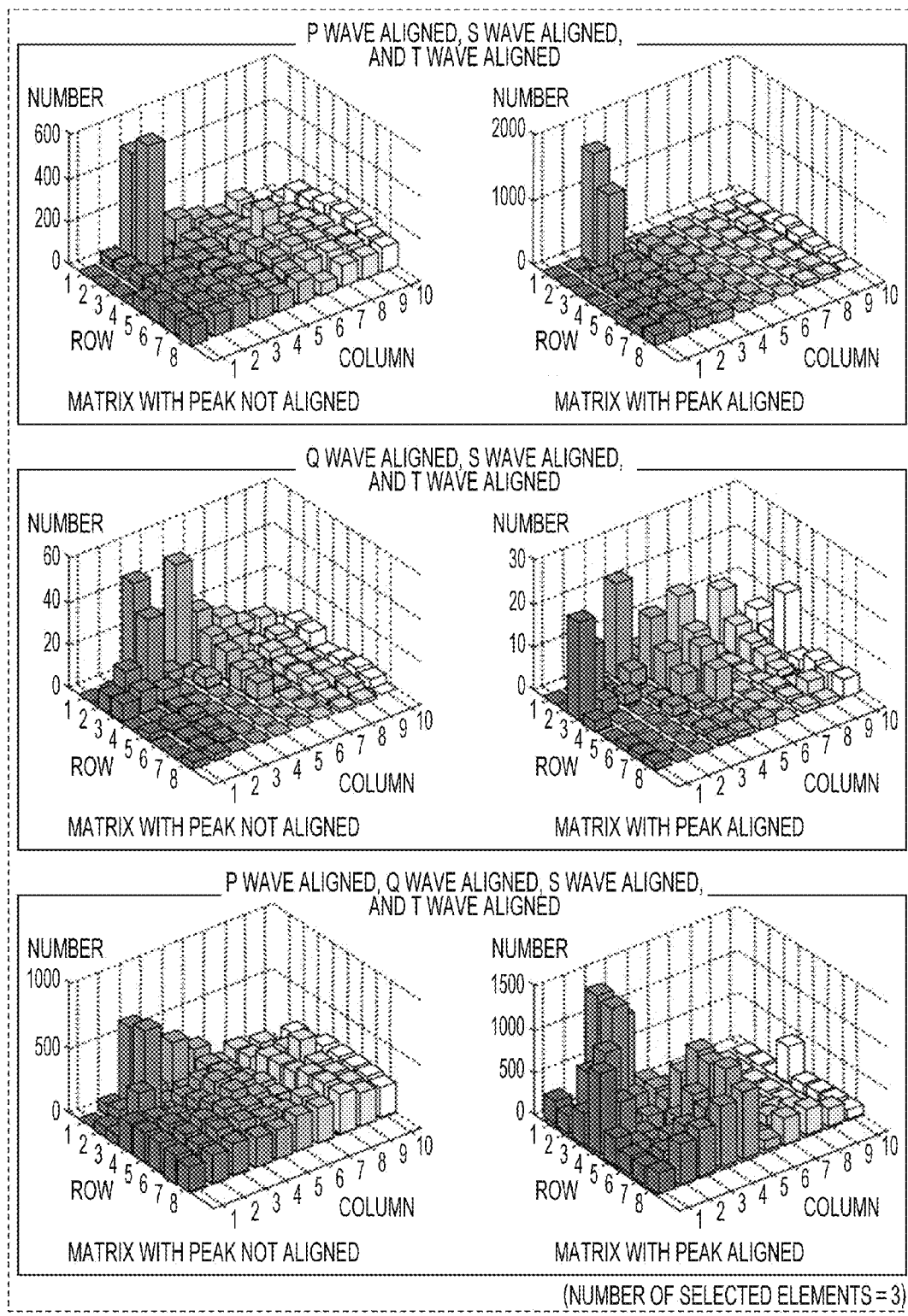
FIG. 51 illustrates the positions of three elements included in each of the element combinations having an accuracy rate of 100% in the matrix when the number of selected elements is 3 according to the third exemplary embodiment.

FIG. 35 is a block diagram of the configuration of a personal authentication apparatus according to a modification of the second exemplary embodiment.

A personal authentication apparatus 20A includes an electrocardiograph measuring unit 11, a peak detection unit 12, an acquiring unit 13, a wavelet transform unit 16, a selection unit 17, an input unit 14a, a registration unit 14c, and an authentication unit 15a.

Input Unit

The input unit 14a receives the identification information regarding a user through, for example, the operation performed by the user. The input unit 14a is formed from, for example, a keyboard and one of a mouse and a touch panel.

Registration Unit

Each time the identification information regarding a user is received by the input unit 14a, the registration unit 14c associates the identification information regarding the user with a characteristic vector containing dim elements selected by the selection unit 17 for the identification information regarding the user. In this manner, the registration unit 14c generates the above-described registration information. Thereafter, the registration unit 14c stores the generated registration information in the registration storage unit DB2. Through such processing, the characteristic vector containing dim elements acquired by the selection unit 17 is registered as the registered characteristic vector. For example, the registration unit 14c registers the characteristic vector containing dim elements acquired by the selection unit 17 as a registered characteristic vector within a predetermined time period after the identification information regarding the user is received by the input unit 14a.

Processing Flow in Registration Phase

FIG. 36 is a flowchart of the processing operation performed by the personal authentication apparatus 20A in the registration phase according to the modification of the second exemplary embodiment.

The personal authentication apparatus 20A performs the processes in steps S80 to S85. The processes performed in steps S80 to S85 are the same as the processes performed by the personal authentication apparatus 20 of the above-described second exemplary embodiment in the authentication phase, that is, the processes performed in steps S70 to S75 illustrated in FIG. 28, respectively.

Subsequently, the registration unit 14c associates the characteristic vector containing dim elements selected by the selection unit 17 with the user identification information received by the input unit 14a and stores the characteristic vector in the registration information (step S86). At that time, the characteristic vector is stored as the registered characteristic vector. Such a storing process is performed for each of a plurality of measurements for each of the users to be registered and, thus, the registration information illustrated in FIG. 26 is generated. In addition, through the process in step S86, the characteristic vector of a user to be registered can be registered.

As described above, unlike the personal authentication apparatus 20 according to the second exemplary embodiment, the personal authentication apparatus 20A according to the present modification further includes an input unit 14a and a registration unit 14c. The input unit 14a receives the identification information regarding each of a plurality of users to be registered. The registration unit 14c associates the identification information regarding each of the users to be registered received by the input unit 14a with the characteristic information indicating the characteristics of the first normalized electrocardiographic waveform acquired by the acquiring unit 13 for the user. In this manner, the registration unit 14c generates the registration information.

Thus, like the modification of the first exemplary embodiment, according to the present modification, the registration information is generated by using the first normalized electrocardiographic waveform acquired by the acquiring unit 13. Accordingly, correct registration information can be easily generated.

Third Exemplary Embodiment

In the above-described exemplary embodiments, a user is authenticated using the electrocardiographic waveform measured for 20 seconds or longer. The present inventor obtained the accuracy rate of authentication in each of the above-described exemplary embodiment using the electrocardiographic waveform for the first 3 seconds.

FIG. 37 illustrates the accuracy rate when the electrocardiographic waveform is measured for 20 seconds or longer and the accuracy rate when the electrocardiographic waveform is measured for 3 seconds in the first exemplary embodiment.

As illustrated in FIG. 37, according to the first exemplary embodiment, even when the peak-to-be-adjusted combination used for normalization is any one of the 12 peak-to-be-adjusted combinations, the accuracy rate for the 3-second measurement is lower than the accuracy rate for the 20-second or longer measurement. In addition, even when no peak to be adjusted is set (i.e., in the case of the Japanese Patent No. 4782141), the accuracy rate for the 3-second measurement is lower than the accuracy rate for the 20-second or longer measurement.

FIG. 38 illustrates the accuracy rate when the electrocardiographic waveform is measured for 20 seconds or longer and the accuracy rate when the electrocardiographic waveform is measured for 3 seconds in the second exemplary embodiment.

As illustrated in FIG. 38, according to the second exemplary embodiment, even when the number of selected elements is either 2 or 3 and the peak-to-be-adjusted combination used for normalization is any one of the 12 peak-to-be-adjusted combinations, the accuracy rate for the 3-second measurement is lower than the accuracy rate for the 20-second or longer measurement.

Accordingly, the personal authentication apparatus according to the present exemplary embodiment applies the wavelet transform to two types of normalized electrocardiographic waveform. In this manner, a user can be authenticated with high accuracy rate even for the electrocardiographic waveform having a short time length. Note that like the personal authentication apparatus 20 according to the second exemplary embodiment, the personal authentication apparatus according to the present exemplary embodiment includes the electrocardiograph measuring unit 11, the peak detection unit 12, the acquiring unit 13, the wavelet transform unit 16, the selection unit 17, and the authentication unit 15a illustrated in FIG. 25. However, the acquiring unit 13, the wavelet transform unit 16, and the selection unit 17 according to the present exemplary embodiment perform processing that partially differs from that of the second exemplary embodiment.

FIG. 39 illustrates an example of a method for generating the characteristic vector according to the third exemplary embodiment.

According to the present exemplary embodiment, the personal authentication apparatus 20 performs the wavelet transform and scaling down on even a normalized electrocardiographic waveform having a peak that is not time-adjusted in addition to the normalized electrocardiographic waveform having a peak that is time-adjusted. Note that the normalized electrocardiographic waveform having a peak that is time-adjusted is an electrocardiographic waveform normalized so that the time period between the peak to be adjusted and the peak of the first R wave is set to a predetermined time period corresponding to the peak to be adjusted. That is, in the normalized electrocardiographic waveform having a peak that is time-adjusted, the peak of each of the P wave, Q wave, S wave, and T wave is aligned. In contrast, although the normalized electrocardiographic waveform having a peak that is not time-adjusted is a normalized electrocardiographic waveform, the peak of any one of the P wave, Q wave, S wave, and T wave included in the electrocardiographic waveform is not adjusted such that the time period between the peak thereof and the peak of the first R wave is the same as the predetermined time period. That is, in the normalized electrocardiographic waveform having a peak that is not time-adjusted, the peak of none of the P wave, Q wave, S wave, and T wave is aligned.

The personal authentication apparatus 20 selects at least one element from the matrix obtained from each of the normalized electrocardiographic waveform having a peak that is time-adjusted and the normalized electrocardiographic waveform having a peak that is not time-adjusted. Note that like the second exemplary embodiment, these matrices are matrices obtained by applying the wavelet transform to the normalized electrocardiographic waveform and scaling down the normalized electrocardiographic waveform.

In this manner, when selecting one element from each of two matrices, the personal authentication apparatus 20 generates a two-dimensional characteristic vector containing the two selected elements. In addition, when selecting one element from one of the two matrices and selecting two elements from the other matrix, the personal authentication apparatus 20 generates a three-dimensional characteristic vector containing the selected three elements.

Thereafter, like the second exemplary embodiment, the personal authentication apparatus 20 performs the discrimination analysis using the generated characteristic vector and authenticates the user.

The number of combinations of two or three elements selected from two matrices each having 8 rows and 10 columns is large. The number of combinations of two elements, that is, the number of combinations when the number of selected elements is 2 is 6400, and the number of combinations of three elements, that is, the number of combinations when the number of selected elements is 3 is 505600. According to the present exemplary embodiment, the accuracy rates for all the combinations are calculated, and the highest accuracy rate is obtained.

FIG. 40 illustrates the highest accuracy rate when the number of selected elements is 2 according to the third exemplary embodiment. FIG. 41 illustrates the highest accuracy rate when the number of selected elements is 3 according to the third exemplary embodiment.

As can be seen from FIGS. 40 and 41, according to the present exemplary embodiment, the highest accuracy rate for the electrocardiographic waveform measured for 20 seconds or longer is almost 100% even when any one of the peaks is used as the peak to be adjusted. According to the present exemplary embodiment, the number of the peak-to-be-adjusted combinations having the highest accuracy rate 100% for the data obtained by 3-second measurement is greater than the number of the peak-to-be-adjusted combinations having the highest accuracy rate 100% according to the second exemplary embodiment if the number of selected elements is 3.

FIG. 42 illustrates the number of element combinations having an accuracy rate of 100% when the number of selected elements is 2 according to the third exemplary embodiment. FIG. 43 illustrates the number of element combinations having an accuracy rate of 100% when the number of selected elements is 3 according to the third exemplary embodiment.

As can be seen from FIGS. 42 and 43, according to the present exemplary embodiment, the number of the element combinations having an accuracy rate of 100% for the electrocardiographic waveform measured for 3 seconds is greater than the number of the element combinations having an accuracy rate of 100% according to the second exemplary embodiment if the number of selected elements is 3.

FIGS. 44 to 47 illustrate the positions of two elements contained in each of the element combinations having an accuracy rate of 100% in the matrix when the number of selected elements is 2, according to the third exemplary embodiment. Note that in each of FIGS. 44 to 47, two graphs are illustrated for each of the peak-to-be-adjusted combinations, that is, for each of aligned waves. One of the two graphs corresponds to a matrix obtained from the normalized electrocardiographic waveform having a peak that is not time-adjusted (i.e., a matrix having a peak that is not aligned). The other graph corresponds to a matrix obtained from the normalized electrocardiographic waveform having a peak that is time-adjusted (i.e., a matrix having a peak that is aligned).

According to the present exemplary embodiment, when the number of selected elements is 2, that is, the characteristic vector is a two-dimensional vector, the selected position information indicates the position of the element having the highest value on the ordinate in the matrix in each of the two graphs in each of FIGS. 44 to 47.

FIGS. 48 to 51 illustrate the positions of three elements included in each of the element combinations having an accuracy rate of 100% in the matrix when the number of selected elements is 3, according to the third exemplary embodiment. Note that as in FIGS. 44 to 47, in FIGS. 48 to 51, two graphs are illustrated for each of the peak-to-be-adjusted combinations, that is, for each of aligned waves.

According to the present exemplary embodiment, when the number of selected elements is 3, that is, the characteristic vector is a three-dimensional vector, the selected position information indicates the position of the element having the highest value on the ordinate in the matrix in one of the two graphs in FIGS. 48 to 51. In addition, the selected position information indicates the positions of two elements having the highest value and the second highest value on the ordinate in the matrix in the other graph in FIGS. 48 to 51.

In this manner, since the selected position information according to the present exemplary embodiment indicates the position of each of the elements included in the element combination having an accuracy rate of 100%, a user can be authenticated with high accuracy.

Processing Flow in Authentication Phase

Figure 52:
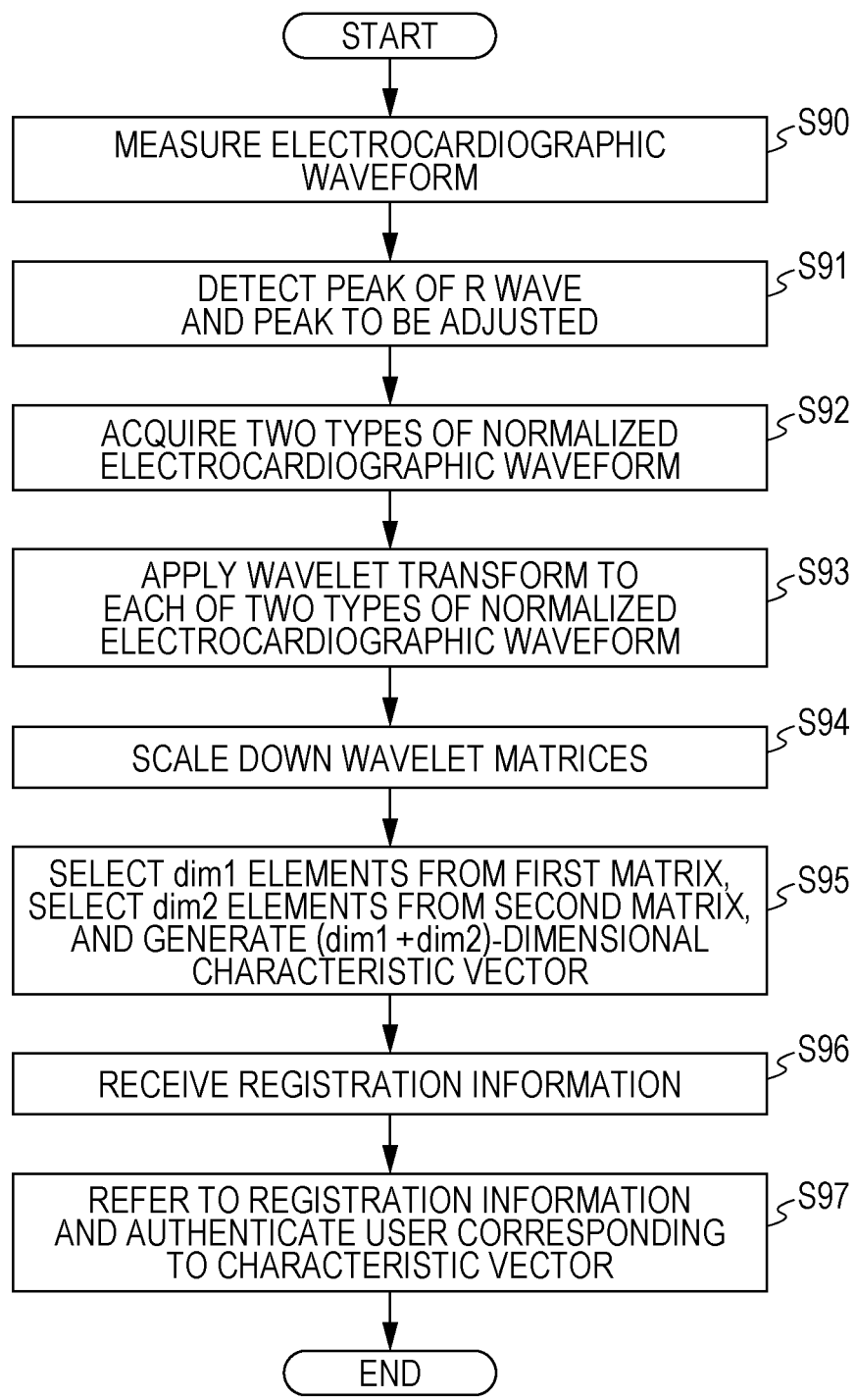
FIG. 52 is a flowchart of the processing operation performed by the personal authentication apparatus in the authentication phase according to the third exemplary embodiment.

FIG. 52 is a flowchart of the processing operation performed by the personal authentication apparatus in the authentication phase according to the third exemplary embodiment.

The electrocardiograph measuring unit 11 measures the electrocardiographic waveform of a user using a plurality of electrodes in contact with the user first (step S90).

The peak detection unit 12 detects, from the electrocardiographic waveform measured in step S90, the peaks of the first R wave and the second R wave in the electrocardiographic waveform. In addition, the peak detection unit 12 detects the peaks of the P wave, Q wave, S wave, and T wave as the peaks to be adjusted (step S91).

The acquiring unit 13 expands or contracts the electrocardiographic waveform in the time axis direction and the amplitude direction on the basis of the detected peaks and acquires a normalized electrocardiographic waveform having a peak that is time-adjusted and a normalized electrocardiographic waveform having a peak that is not time-adjusted (step S92). When acquiring the normalized electrocardiographic waveform having a peak that is time-adjusted, the acquiring unit 13 expands or contracts the time period between the peak of the first R wave and the peak of the second R wave to a first predetermined time period (RRnorm). In addition, the acquiring unit 13 expands or contracts the time period between the peak of the first R wave and each of the peaks to be adjusted (i.e., the peaks of the P wave, Q wave, S wave, and T wave) in the electrocardiographic waveform to the predetermined time period corresponding to the peak to be adjusted. That is, the acquiring unit 13 aligns the peak of each of the P wave, Q wave, S wave, and T wave. In contrast, when acquiring the normalized electrocardiographic waveform having a peak that is not time-adjusted, the acquiring unit 13 expands or contracts the time period between the peak of the first R wave and the peak of the second R wave to a first predetermined time period (RRnorm). However, at that time, the acquiring unit 13 does not adjust the time of the peak of any one of the P wave, Q wave, S wave, and T wave. That is, the acquiring unit 13 does not align the peak of any one of the P wave, Q wave, S wave, and T wave.

The wavelet transform unit 16 applies the wavelet transform to the normalized electrocardiographic waveform having a peak that is time-adjusted and the normalized electrocardiographic waveform having a peak that is not time-adjusted acquired in step S92 and generates two wavelet matrices (step S93). Subsequently, if the size of each of the two wavelet matrices generated in step S93 is larger than a predetermined size, the wavelet transform unit 16 scales down the wavelet matrix (step S94).

The selection unit 17 selects, from one of the two matrices generated through scale-down in step S94, dim1 elements located at the positions indicated by the selected position information. In addition, the selection unit 17 selects dim2 elements located at the positions indicated by the selected position information from the other matrix. Thereafter, the selection unit 17 generates a (dim1+dim2)-dimensional characteristic vector containing the (dim1+dim2) elements (step S95). Note that each of dim1 and dim2 is 1 or 2.

The authentication unit 15*a* acquires the registration information stored in the registration storage unit DB2 (step S96). Thereafter, the authentication unit 15*a* refers to the acquired registration information (e.g., the registration information illustrated in FIG. 26) and authenticates the user having the characteristic vector generated by the selection unit 17 (step S97). That is, the authentication unit 15*a* performs the discrimination analysis using the generated characteristic vector and a plurality of the registered characteristic vectors each corresponding to the identification information regarding one of a plurality of users included in the registration information. As a result, the authentication unit 15*a* outputs the identification information of a user corresponding to the generated characteristic vector.

As described above, unlike the first exemplary embodiment, the acquiring unit 13 according to the present exemplary embodiment additionally expands or contracts the measured electrocardiographic waveform in the time axis direction and the amplitude direction and acquires a second normalized electrocardiographic waveform. At that time, the acquiring unit 13 expands or contracts, among the peaks included in the measured electrocardiographic waveform, only the time period between the peak of the first R wave and the peak of the second R wave to the first predetermined time period in the time axis direction. In addition, unlike the first exemplary embodiment, the personal authentication apparatus 20 according to the present exemplary embodiment further include the wavelet transform unit 16 and the selection unit 17. The wavelet transform unit 16 applies the wavelet transform to the first normalized electrocardiographic waveform acquired by the acquiring unit 13 and generates a first matrix. In addition, the wavelet transform unit 16 applies the wavelet transform to the second normalized electrocardiographic waveform acquired by the acquiring unit 13 and generates a second matrix. The selection unit 17 selects at least one element from each of the first matrix and the second matrix and generates a characteristic vector having at least two selected elements. Furthermore, the authentication unit 15*a* refers to the registration information including the registered characteristic vectors as the characteristic information regarding all the users and searches for the registered characteristic vector that is similar to the generated characteristic vector and outputs the identification information regarding a user associated with the found registered characteristic vector.

In this manner, the wavelet transform is applied to the first normalized electrocardiographic waveform and the second normalized electrocardiographic waveform. Accordingly, the accuracy rate can be increased for even an electrocardiographic waveform measured for, for example, 3 seconds. Thus, a user (a person) can be authenticated in a short time with high accuracy.

Modifications

According to the above-described third exemplary embodiment, the personal authentication apparatus 20 performs authentication using the registration information stored in the registration storage unit DB2. However, a registration process that generates the registration information may be performed.

Like the personal authentication apparatus 20A according to the modification of the second exemplary embodiment, the personal authentication apparatus 20A according to the present modification includes the electrocardiograph measuring unit 11, the peak detection unit 12, the acquiring unit 13, the input unit 14*a*, the registration unit 14*c*, the wavelet transform unit 16, the selection unit 17, and the authentication unit 15*a* illustrated in FIG. 35.

Processing Flow in Registration Phase

Figure 53:
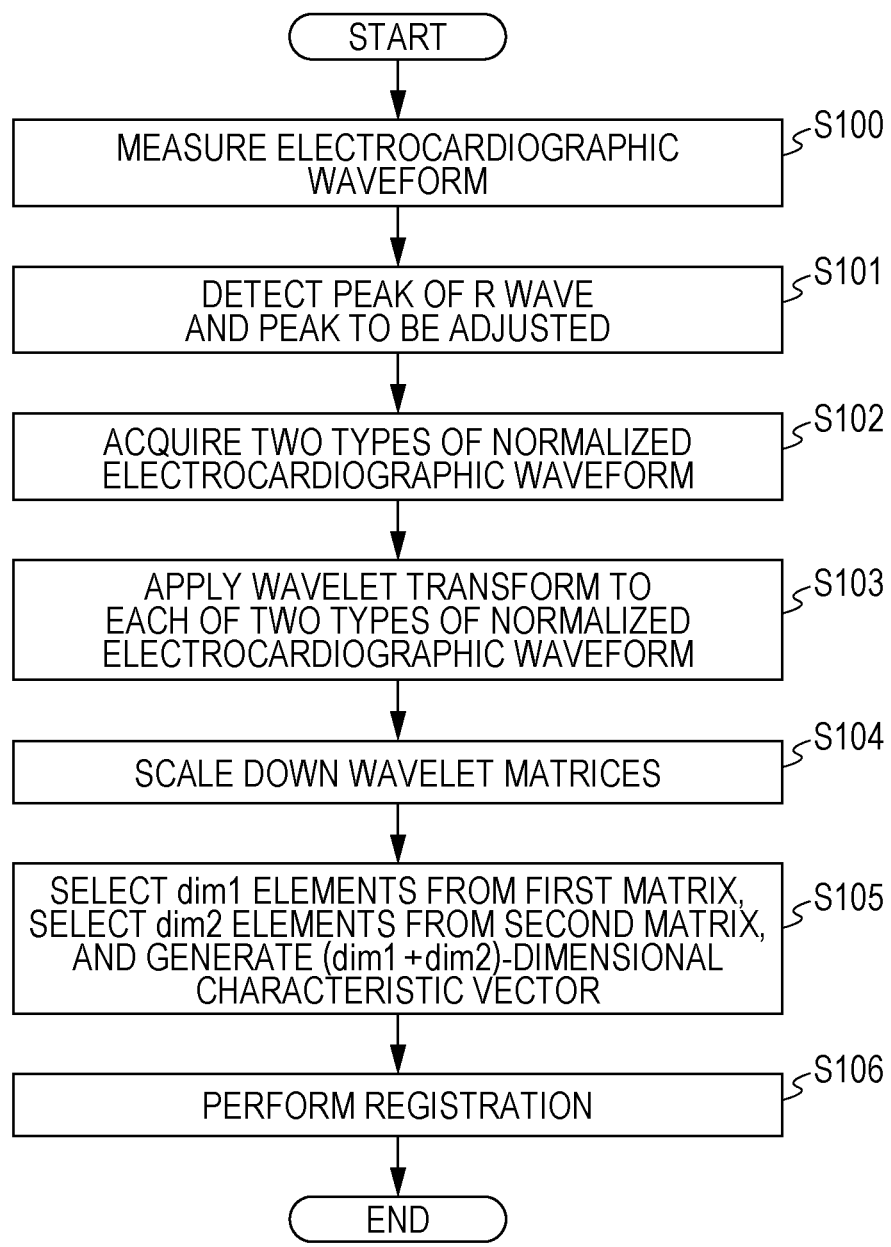
FIG. 53 is a flowchart of the processing operation performed by a personal authentication apparatus in a registration phase according to a modification of the third exemplary embodiment.

FIG. 53 is a flowchart of the processing operation performed by the personal authentication apparatus 20A in the registration phase according to the modification of the third exemplary embodiment.

The personal authentication apparatus 20A performs the processes in steps S100 to S105. The processes performed in steps S100 to S105 are the same as the processes performed by the personal authentication apparatus 20 of the above-described third exemplary embodiment in the authentication phase, that is, the processes performed in steps S90 to S95 illustrated in FIG. 52, respectively.

Subsequently, the registration unit 14*c* of the personal authentication apparatus 20A associates the characteristic vector containing (dim1+dim2) elements selected by the selection unit 17 with the user identification information received by the input unit 14*a* and stores the characteristic vector in the registration information (step S106). At that time, the characteristic vector is stored as the registered characteristic vector. Such a storing process is performed for each of a plurality of measurements for each of the users to be registered and, thus, the registration information illustrated in FIG. 26 is generated. In addition, through the process in step S106, the characteristic vector of a user to be registered can be registered.

As described above, unlike the personal authentication apparatus 20 according to the third exemplary embodiment, the personal authentication apparatus 20A according to the present modification further includes an input unit 14*a* and a registration unit 14*c*. The input unit 14*a* receives the input identification information regarding each of a plurality of users to be registered. The registration unit 14*c* associates the identification information regarding each of the users to be registered received by the input unit 14*a* with the registered characteristic vector indicating the characteristics of the first and second normalized electrocardiographic waveforms acquired by the acquiring unit 13 for the user to be registered. In this manner, the registration unit 14*c* generates the registration information.

Thus, like the modification of the second exemplary embodiment, according to the present modification, the registration information is generated by using the first and second normalized electrocardiographic waveforms acquired by the acquiring unit 13. Accordingly, correct registration information can be easily generated.

While the personal authentication apparatus according to at least one aspect has been described with reference to the exemplary embodiments and the modifications, the present disclosure is not limited to the exemplary embodiments. A variety of modifications of the present exemplary embodiment that a person who skilled in the art can conceive and an embodiment configured by combining the constituent elements of different exemplary embodiments may be encompassed within the scope of the present disclosure.

For example, while the above-described exemplary embodiments and the modifications have been described with reference to the personal authentication apparatuses without a recording medium, such as the regulation storage unit DB1, the personal authentication apparatuses may include a recording medium.

In addition, while the second and third exemplary embodiments and the modifications have been described with reference to, as illustrated in FIGS. 27 and 39, the normalized electrocardiographic waveform in which the peak of each of the P wave, Q wave, S wave, and T wave is aligned, the peak of each of all the P wave, Q wave, S wave, and T wave need not be aligned in the normalized electrocardiographic waveform. Like the first exemplary embodiment and the modification of the first exemplary embodiment, the peak of each of at least one of the P wave, Q wave, S wave, and T wave contained in the electrocardiographic waveform may be aligned (note that at that time, the peak of at least one of the P and Q waves needs to be selected).

In addition, while the second and third exemplary embodiments and the modifications have been described with reference to the registration information including a plurality of the registered characteristic vectors associated with the identification information regarding each of the users, the registration information may include only one registered characteristic vector for the identification information regarding each of the users. In such a case, the authentication unit 15a searches for the registered characteristic vector similar to the characteristic vector acquired by the selection unit 17 using the characteristic vector and the distance between the characteristic vector and each of the registered characteristic vectors contained in the registration information instead of using a discrimination analysis method. Thereafter, the authentication unit 15a outputs the identification information regarding a user associated with the registered characteristic vector.

In addition, while the above-described exemplary embodiments and the modifications have been described with reference to the peak to be adjusted selected on the basis of the regulation information, the peak of the wave selected as the peak to be adjusted may be changed.

In addition, the personal authentication apparatus according to the above-described exemplary embodiments and the modifications may be configured using hardware.

Hardware Configuration

Figure 54:
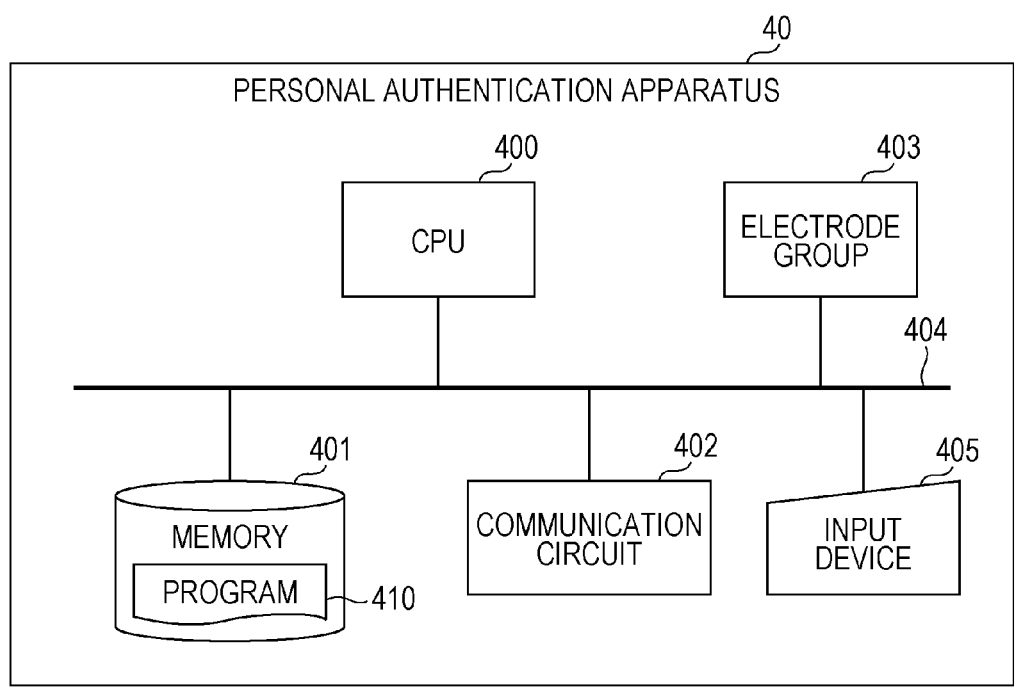
FIG. 54 illustrates the hardware configuration of the personal authentication apparatus according to the exemplary embodiments and the modifications.

FIG. 54 illustrates the hardware configuration of the personal authentication apparatuses according to the above-described exemplary embodiments and the modifications.

A personal authentication apparatus 40 is any one of the personal authentication apparatuses according to the above-described exemplary embodiments and the modifications. The personal authentication apparatus 40 includes a central processing unit (CPU) 400, a memory 401, a communication circuit 402, an electrode group 403, and an input device 405. The CPU 400, the memory 401, the communication circuit 402, the electrode group 403, and the input device 405 are connected to one another via a bus 404 and communicate data with one another. The input device 405 corresponds to the above-described input unit 14a. The input device 405 need not be included in the personal authentication apparatus 40.

The CPU 400 executes a computer program 410 stored in the memory 401. In this manner, the CPU 400 functions as at least one of the constituent elements, that is, the electrocardiograph measuring unit 11, the peak detection unit 12, the acquiring unit 13, the registration units 14b and 14c, the authentication units 15 and 15a, the wavelet transform unit 16, and the selection unit 17. The computer program 410 has the procedure written therein for causing the constituent elements to perform the processing procedures indicated by the above-described flowcharts (refer to FIGS. 13 to 17, FIG. 23, FIG. 28, FIG. 36, FIG. 52, and FIG. 53). The personal authentication apparatus 40 performs the above-described operations in accordance with the computer program 410.

The communication circuit 402 is a circuit that communicates with external apparatuses using a predetermined protocol wirelessly or wired.

At least one of the constituent elements, that is, the electrocardiograph measuring unit 11, the peak detection unit 12, the acquiring unit 13, the registration units 14b and 14c, the authentication units 15 and 15a, the wavelet transform unit 16, and the selection unit 17 may be configured as hardware, such as a digital signal processor (DSP) having a computer program in a semiconductor circuit. The computer program is recorded in a recording medium, such as a CD-ROM, and is distributed in the market in the form of a product. Alternatively, the computer program can be transmitted via an electrical communication network, such as the Internet. It should be noted that the above-described variety of aspects can be combined as long as no conflict arises.

The personal authentication apparatus according to an aspect of the present disclosure can authenticate a person with high accuracy. The personal authentication apparatus is applicable as a personal authentication apparatus used in the security field.

What is claimed is:

1. A personal authentication apparatus comprising a processor configured to:
   an electrocardiograph measuring circuit that measures a first electrocardiographic waveform of a first user using a plurality of electrodes adapted to be located on the first user;
   a peak detector that detects at least one of a peak of a P wave and a peak of a Q wave, a peak of an S wave, a peak of a T wave, a peak of a first R wave, and a peak of a second R wave in the first electrocardiographic waveform;
   an acquirer that acquires a first normalized electrocardiographic waveform by expanding or contracting the first electrocardiographic waveform in a time axis direction and an amplitude direction on a basis of the detected peaks; and
   an authenticator that refers to prestored registration information including identification information regarding a plurality of registered users, and for each of the plurality of registered users characteristic information indicating characteristics of an electrocardiographic waveform, the authenticator outputting authenticated identification information regarding an authenticated one of the plurality of users corresponding to characteristic information that matches characteristic information of the first normalized electrocardiographic waveform, wherein the acquirer, under a first process, is configured to expand or contract a time interval between the peak of the first R wave and the peak of the second R wave to a first predetermined time period, wherein the acquirer, under a second process, is configured to (i) expand or contract a time interval between the peak of the first R wave and a peak of the P wave to a second predetermined time period, (ii) expand or contract a time interval between the peak of the first R wave and a peak of the Q wave to a third predetermined time period, or (iii) expand or contract the time interval between the peak of the first R wave and the peak of the P wave to the second predetermined time period and expand or contract the time interval between the peak of the first R wave and the peak of the Q wave to the third predetermined time period, wherein matching characteristic information of the authenticated identification information comprises (i) a first time interval between a peak to be adjusted by the acquirer representing a peak of at least one wave among the P wave, the Q wave, the S wave, and the T wave and the peak of the first R wave, and (ii) a second time interval between the peak of the first R wave and the peak of the second R wave, wherein the personal authentication apparatus further comprises:

a wavelet transformer that applies a wavelet transform to the first normalized electrocardiographic waveform acquired by the acquirer, and generates a first matrix; and a selector that selects at least two elements from the generated first matrix and generates a first characteristic vector having the selected at least two elements, and wherein the authenticator refers to the prestored registration information including characteristic vectors as the characteristic information regarding each of the plurality of registered users, and outputs the identification information corresponding to the authenticated one of the plurality of registered users associated with a characteristic vector matching the generated first characteristic vector.

2. A personal authentication apparatus comprising a processor configured to:

an electrocardiograph measuring circuit that measures a first electrocardiographic waveform of a first user using a plurality of electrodes adapted to be located on the first user;

a peak detector that detects at least one of a peak of a P wave and a peak of a Q wave, a peak of an S wave, a peak of a T wave, a peak of a first R wave, and a peak of a second R wave in the first electrocardiographic waveform;

an acquirer that acquires a first normalized electrocardiographic waveform by expanding or contracting the first electrocardiographic waveform in a time axis direction and an amplitude direction on a basis of the detected peaks; and an authenticator that refers to prestored registration information including identification information regarding a plurality of registered users, and for each of the plurality of registered users characteristic information indicating characteristics of an electrocardiographic waveform, the authenticator outputting authenticated identification information regarding an authenticated one of the plurality of users corresponding to characteristic information that matches characteristic information of the first normalized electrocardiographic waveform, wherein the acquirer, under a first process, is configured to expand or contract a time interval between the peak of the first R wave and the peak of the second R wave to a first predetermined time period, wherein the acquirer, under a second process, is configured to (i) expand or contract a time interval between the peak of the first R wave and a peak of the P wave to a second predetermined time period, (ii) expand or contract a time interval between the peak of the first R wave and a peak of the Q wave to a third predetermined time period, or (iii) expand or contract the time interval between the peak of the first R wave and the peak of the P wave to the second predetermined time period and expand or contract the time interval between the peak of the first R wave and the peak of the Q wave to the third predetermined time period, wherein matching characteristic information of the authenticated identification information comprises (i) a first time interval between a peak to be adjusted by the acquirer representing a peak of at least one wave among the P wave, the Q wave, the S wave, and the T wave and the peak of the first R wave, and (ii) a second time interval between the peak of the first R wave and the peak of the second R wave, wherein the acquirer further acquires a second normalized electrocardiographic waveform by expanding or contracting a second electrocardiographic waveform in the time axis direction and the amplitude direction, wherein in the second normalized electrocardiographic waveform, among the time intervals between the peaks included in the second electrocardiographic waveform, only the time interval between the peak of the first R wave and the peak of the second R wave is expanded or contracted to the first predetermined time period, wherein the personal authentication apparatus further comprises:

a wavelet transformer that applies a wavelet transform to the first normalized electrocardiographic waveform to generate a first matrix, and applies the wavelet transform to the second normalized electrocardiographic waveform to generate a second matrix; and a selector that selects at least one element from each of the first matrix and the second matrix and generates a characteristic vector corresponding to the selected at least two elements, and wherein the authenticator refers to the prestored registration information including a characteristic vector as the characteristic information regarding each of the plurality of registered users, and outputs the identification information corresponding to an authenticated one of the plurality of registered users associated with a characteristic vector matching the generated characteristic vector.

3. A personal authentication method using a processor, comprising:

measuring a first electrocardiographic waveform of a first user using a plurality of electrodes adapted to be located on the first user;

detecting at least one of a peak of a P wave and a peak of a Q wave, a peak of a first R wave, and a peak of a second R wave in the first electrocardiographic waveform;

acquiring a first normalized electrocardiographic waveform by expanding or contracting the first electrocardiographic waveform in a time axis direction and an amplitude direction on a basis of the detected peaks; and referring to prestored registration information including identification information regarding a plurality of registered users, and for each of the plurality of registered users characteristic information indicating characteristics of an electrocardiographic waveform, and outputting authenticated identification information regarding an authenticated one of the plurality of users corresponding to characteristic information that matches characteristic information of the first normalized electrocardiographic waveform, wherein in acquiring the first normalized electrocardiographic waveform, a time interval between the peak of the first R wave and the peak of the second R wave is expanded or contracted to a first predetermined time period in the time axis direction, wherein in acquiring the first normalized electrocardiographic waveform, (i) a time interval between the peak of the first R wave and a peak of the P wave is expanded or contracted to a second predetermined time period different from the first predetermined time period, (ii) a time interval between the peak of the first R wave and a peak of the Q wave is expanded or contracted to a third predetermined time period different from the first predetermined time period and the second predetermined time period, or (iii) a time interval between the peak of the first R wave and the peak of the P wave is expanded or contracted to the second predetermined time period and a time interval between the peak of the first R wave and the peak of the Q wave is expanded or contracted to the third predetermined time period, wherein the personal authentication method further comprises:

applying a wavelet transform to the acquired first normalized electrocardiographic waveform and generating a first matrix; and selecting at least two elements from the generated first matrix and generating a first characteristic vector having the selected at least two elements, and wherein in outputting the authenticated identification information, the prestored registration information including characteristic vectors as the characteristic information regarding each of the plurality of registered users is referred to, and the identification information corresponding to the authenticated one of the plurality of registered users associated with a characteristic vector matching the generated first characteristic vector is output.

4. A personal authentication method using a processor, comprising:

measuring a first electrocardiographic waveform of a first user using a plurality of electrodes adapted to be located on the first user;

detecting at least one of a peak of a P wave and a peak of a Q wave, a peak of a first R wave, and a peak of a second R wave in the first electrocardiographic waveform;

acquiring a first normalized electrocardiographic waveform by expanding or contracting the first electrocardiographic waveform in a time axis direction and an amplitude direction on a basis of the detected peaks; and referring to prestored registration information including identification information regarding a plurality of registered users, and for each of the plurality of registered users characteristic information indicating characteristics of an electrocardiographic waveform, and outputting authenticated identification information regarding an authenticated one of the plurality of users corresponding to characteristic information that matches characteristic information of the first normalized electrocardiographic waveform, wherein in acquiring the first normalized electrocardiographic waveform, a time interval between the peak of the first R wave and the peak of the second R wave is expanded or contracted to a first predetermined time period in the time axis direction, wherein in acquiring the first normalized electrocardiographic waveform, (i) a time interval between the peak of the first R wave and a peak of the P wave is expanded or contracted to a second predetermined time period different from the first predetermined time period, (ii) a time interval between the peak of the first R wave and a peak of the Q wave is expanded or contracted to a third predetermined time period different from the first predetermined time period and the second predetermined time period, or (iii) a time interval between the peak of the first R wave and the peak of the P wave is expanded or contracted to the second predetermined time period and a time interval between the peak of the first R wave and the peak of the Q wave is expanded or contracted to the third predetermined time period, wherein a second normalized electrocardiographic waveform is further acquired by expanding or contracting a second electrocardiographic waveform in the time axis direction and the amplitude direction, wherein in acquiring the second normalized electrocardiographic waveform, among the time intervals between the peaks included in the second electrocardiographic waveform, only the time interval between the peak of the first R wave and the peak of the second R wave is expanded or contracted to the first predetermined time period in the time axis direction, wherein the personal authentication method further comprises:

applying a wavelet transform to the acquired first normalized electrocardiographic waveform to generate a first matrix, and applying the wavelet transform to the acquired second normalized electrocardiographic waveform to generate a second matrix; and selecting at least one element from each of the first matrix and the second matrix and generating a characteristic vector corresponding to the selected at least two elements, and wherein in outputting the authenticated identification information, the prestored registration information including a characteristic vector as the characteristic information regarding each of the plurality of registered users is referred to, and the identification information corresponding to an authenticated one of the plurality of registered users associated with a characteristic vector matching the generated characteristic vector is output.

* * * * *